US010995146B2

(12) United States Patent
Gromada et al.

(10) Patent No.: US 10,995,146 B2
(45) Date of Patent: May 4, 2021

(54) METHODS OF TREATING SEVERE INSULIN RESISTANCE BY INTERFERING WITH GLUCAGON RECEPTOR SIGNALING

(71) Applicant: Regeneron Pharmaceuticals, Inc., Tarrytown, NY (US)

(72) Inventors: Jesper Gromada, Scarsdale, NY (US); Haruka Okamoto, New York, NY (US); Stephen Jaspers, Brewster, NY (US); Joyce Harp, Montclair, NJ (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days.

(21) Appl. No.: 16/328,935

(22) PCT Filed: Aug. 29, 2017

(86) PCT No.: PCT/US2017/049137
§ 371 (c)(1),
(2) Date: Feb. 27, 2019

(87) PCT Pub. No.: WO2018/044903
PCT Pub. Date: Mar. 8, 2018

(65) Prior Publication Data
US 2019/0218301 A1 Jul. 18, 2019

Related U.S. Application Data

(60) Provisional application No. 62/411,032, filed on Oct. 21, 2016, provisional application No. 62/381,263, filed on Aug. 30, 2016.

(51) Int. Cl.
*C07K 16/28* (2006.01)
*A61P 3/10* (2006.01)
*A61K 39/395* (2006.01)
*A61K 45/06* (2006.01)
*C07K 16/26* (2006.01)
*A61K 38/16* (2006.01)
*A61K 39/00* (2006.01)

(52) U.S. Cl.
CPC .......... *C07K 16/2869* (2013.01); *A61K 38/16* (2013.01); *A61K 39/3955* (2013.01); *A61K 45/06* (2013.01); *A61P 3/10* (2018.01); *C07K 16/26* (2013.01); *C07K 16/28* (2013.01); *A61K 2039/505* (2013.01); *A61K 2039/507* (2013.01); *A61K 2039/54* (2013.01); *A61K 2039/545* (2013.01); *C07K 2317/21* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC .... C07K 16/26; C07K 16/2869; A61K 38/16; A61P 3/10
See application file for complete search history.

(56) References Cited

U.S. PATENT DOCUMENTS

| 4,206,199 A | 6/1980 | Fujino et al. |
| 4,221,777 A | 9/1980 | Nishino |
| 4,272,433 A | 6/1981 | Nishino |
| 4,407,965 A | 10/1983 | Yanaihara |
| 4,423,034 A | 12/1983 | Nakagawa et al. |
| 4,816,567 A | 3/1989 | Cabilly et al. |
| 4,946,778 A | 8/1990 | Ladner et al. |
| 5,712,105 A | 1/1998 | Yanaihara et al. |
| 5,770,445 A | 6/1998 | Kindsvogel et al. |
| 7,947,809 B2 | 5/2011 | Yan et al. |
| 8,545,847 B2 | 10/2013 | Okamoto et al. |
| 2004/0101920 A1 | 5/2004 | Radziejewski et al. |
| 2009/0041784 A1 | 2/2009 | Yan et al. |
| 2009/0252727 A1 | 10/2009 | Korytko, Jr. et al. |
| 2011/0223160 A1 | 9/2011 | Yan et al. |

(Continued)

FOREIGN PATENT DOCUMENTS

| EP | 0658200 B1 | 12/2004 |
| EP | 2074149 B1 | 6/2013 |

(Continued)

OTHER PUBLICATIONS

Allen (1999) The Art, Science and Technology of Pharmaceutical Compounding, 8pgs.
Al-Lazikani (1997) "Standard Conformations for the Canonical Structures of Immunoglobulins" J Mol. Biol. 273:927-948.
Burcelin et al., (1995) "Cloning and sequence analysis of the murine glucagon receptor-encoding gene", Gene 164 (2):305-310.
Chakravarty et al., (2005) Factors that control the tissue-specific transcription of the gene for phosphoenolpyruvate carboxykinase-C. Crit Rev Biochem Mol Biol 40(3): 129-154.
Cochran et al., (2004) "Efficacy of recombinant methionyl human leptin therapy for the extreme insulin resistance of the Rabson-Mendenhall syndrome", Journal of Clinical Endocrinology and Metabolism, 89:1548-1554.
De Laszlo et al., (1999) "Potent, orally absorbed glucagon receptor antagonists", Bioorg. Med. Chem. Lett. 9 (5):641-646.

(Continued)

*Primary Examiner* — Gyan Chandra
(74) *Attorney, Agent, or Firm* — FisherBroyles, LLP; Cara L. Crowley-Weber; Thomas Triolo

(57) ABSTRACT

Provided herein are methods of treating a patient with severe insulin resistance. The methods comprise administering to a patient in need thereof a therapeutic amount of a GCG/GCGR signaling pathway inhibitor, such that blood glucose or beta-hydroxybutyrate levels are lowered or that the severe insulin resistance is mediated, or a condition or disease characterized by severe insulin resistance is mediated, or at least one symptom or complication associated with the condition or disease is alleviated or reduced in severity. The GCG/GCGR signaling pathway inhibitor can be a small molecule inhibitor of the signaling pathway, an antisense inhibitor of the signaling pathway, a GCG neutralizing monoclonal antibody, a GCGR antagonist, a peptide inhibitor of the signaling pathway, a DARPin, a Spiegelmer, an aptamer, engineered Fn type-III domains, etc. The therapeutic methods are useful for treating a human suffering from severe insulin resistance.

11 Claims, 9 Drawing Sheets
Specification includes a Sequence Listing.

(56) References Cited

U.S. PATENT DOCUMENTS

| | | |
|---|---|---|
| 2011/0306624 A1 | 12/2011 | Lin et al. |
| 2016/0075778 A1 | 3/2016 | Okamoto et al. |
| 2019/0218301 A1 | 7/2019 | Gromada et al. |

FOREIGN PATENT DOCUMENTS

| | | |
|---|---|---|
| WO | 2005/065680 A1 | 7/2005 |
| WO | 2005/103081 A2 | 11/2005 |
| WO | 2005/121097 A2 | 12/2005 |
| WO | 2005/123688 A2 | 12/2005 |
| WO | 2006/014618 A2 | 2/2006 |
| WO | 2006/017055 A2 | 2/2006 |
| WO | 2006/086488 A2 | 8/2006 |
| WO | 2006/102067 A1 | 9/2006 |
| WO | 2006/104826 A2 | 10/2006 |
| WO | 2007/047676 A1 | 4/2007 |
| WO | 2007/124463 A1 | 11/2007 |
| WO | 2008/036341 A2 | 3/2008 |
| WO | 2008/042223 A1 | 4/2008 |
| WO | 2008/098244 A1 | 8/2008 |
| WO | 2009/140342 A1 | 11/2009 |
| WO | 2010/030722 A1 | 3/2010 |
| WO | 2010/071750 A1 | 6/2010 |
| WO | 2010/088061 A1 | 8/2010 |
| WO | 2010/098994 A1 | 9/2010 |
| WO | 2011/007722 A1 | 1/2011 |
| WO | 2012/071372 A2 | 5/2012 |
| WO | WO 2013/043817 | 3/2013 |
| WO | 2013/081993 A1 | 6/2013 |
| WO | 2014/181229 A2 | 11/2014 |
| WO | 2016/044337 A1 | 3/2016 |

OTHER PUBLICATIONS

Desbois-Mouthon et al., (1997) "Major circadian variations of glucose homeostasis in a patient with Rabson-Mendenhall syndrome and primary insulin resistance due to a mutation (Cys284→Tyr) in the insulin receptor alpha-subunit", Pediatr. Res., 42(1):72-77.
Gusarova et al., (2014) "ANGPTL8/betatrophin does not control pancreatic beta cell expansion", Cell, 159:691-696.
Hharlow & Lane (1988) Antibodies: a Laboratory Manual, Cold Spring Harbor Lab., Cold Spring Harbor, N.Y.
Kabat, (1991) "Sequences of Proteins of Immunological Interest," National Institutes of Health, Bethesda, Md.
Köhler and Milstein (1975) "Continuous cultures of fused cells secreting antibody of predefined specificity", Nature 256(5517):495-497.
Kufer et al., (2004) "A revival of bispecific antibodies", Trends Biotechnol. 22:238-244.
Langer (1990) "New Methods of Drug Delivery", Science 249:1527-1533.
Longo et al., (1999) "Progressive Decline in Insulin Levels in Rabson-Mendenhall Syndrome" Journal of Clinical Endocrinology & Metabolism, 84(8):2623-2629.
Lynedijian et al., (1995) "Glucokinase and Cytosolic Phosphenolpyruvate Carboxykinase (GTP) in the Human Liver" J Clin Invest. 95(5):1966-73.
Martin et al., (1989) "Modeling antibody hypervariable loops: A combined algorithm", Proc. Natl. Acad. Sci. USA 86:9268-9272.
McCafferty et al. (1990) "Phage antibodies: filamentous phage displaying antibody variable domains", Nature 348:552-554.
McNally et al., (2004) "Cloning and characterization of the glucagon receptor from cynomologous monkey", Peptides 25(7):1171-1178.
Melvin, et al. (2017) "Severe Insulin Resistance: Pathologies", Pratical Diabetes, 34(6):189-194a.
Moller and Flier (1991) "Insulin resistance—mechanisms, syndromes, and implications", New England Journal of Medicine, 325(13):938-948.
Muller et al., (1970) "Abnormal Alpha-Cell Function", N Eng J Med, 283: 109-115.
Okamoto et al., (2015) "Glucagon Receptor Blockade With a Human Antibody Normalizes Blood Glucose in Diabetic Mice and Monkeys", Endocrinology, 156(8): 2781-2794.
Okamoto et al., (2017) "Glucagon Receptor Inhibition Normalizes Blood Glucose in Severe Insulin-Resistant Mice", Proceedings National Academy of Sciences PNAS, 114(10):2753-2758.
Pittner and Fain, (1991) "Activiation of membrane protein kinase C by glucagon and Ca2+-mobilizing hormones in cultured rat heaptocytes", Biochem. J., 277:371-378.
Powell et al., (1998) "Compendium of Excipients for Parenteral Formulations" PDA J Pharm Sci Technol 52:238-311.
Rucktäschel et al., (2000) "Regulation by glucagon (cAMP) and insulin of the promoter of the human phosphoenolpyruvate carboxykinase gene (cytosolic) in cultured rat heatocytes and in human hepatoblastoma cells" 352 Pt 1:211-7.
Savage, et al. (2014) "Insulin Resistance Syndrome", Diapedia, retrieved from URL:https://doi.org/10.14496/dia.410408512).
Schäffer et al., (2008) "A novel high-affinity peptide antagonist to the insulin receptor", Biochem. Biophys. Res. Commun., 376(2):380-383.
Semple et al., (2011), "Genetic Syndromes of Severe Insulin Resistance", Endocrine Reviews, 32(4):498-514.
Tritos and Mantzoros (1998) "Clinical review 97: Syndromes of severe insulin resistance", Journal of Clinical Endocrinology and Metabolism, 83:3025-3030.
Tutt et al., (1991) "Trispecific F(ab')3 Derivatives That Use Cooperative Signaling via the TCR/CD3 Complex and CD2 to Activate and Redirect Resting Cytotoxic T Cells", J. Immunol. 147:60-69.
Unison et al., (1989) "Biological Activities of des-His1 [Glu9]Glucagon Amide, a Glucagon Antagonist1", Peptides, 10:1171-1177.
Vestergaard et al., (1997) "Short- and long-term metabolic effects of recombinant human IGF-I treatment in patients with severe insulin resistance and diabetes mellitus", European Journal of Endocrinology, 136(5):475-482.
Wakelam et al., (1986) "Activation of two-signal-transduction systems in hepatocytes by glucagon", Nature, 323:68-71.
West et al., (1975) "Familial insulin-resistant diabetes, multiple somatic anomalies, and pineal hyperplasia", Arch. Dis. Child., 50(9):703-708.
Wu and Wu et al., (1987) "Receptor-meidated in Vitro Gene Transformation by a Soluble DNA Carrier System", J. Biol. Chem. 262:4429-4432.
Yi et al., (2013) "Betatrophin: a hormone that controls pancreatic β cell proliferation", Cell, 153:747-758.
International Search Report and Written Opinion, PCT/US2017/049137, dated Nov. 7, 2017, 14 pages.

METHODS OF TREATING SEVERE INSULIN RESISTANCE BY INTERFERING WITH GLUCAGON RECEPTOR SIGNALING

CROSS-REFERENCE TO RELATED APPLICATIONS

This application is a National Stage Application of PCT/US2017/049137, filed Aug. 29, 2017, which claims the benefit under 35 USC § 119(e) of U.S. Provisional Application No. 62/411,032, filed Oct. 21, 2016, and to U.S. Provisional Application No. 62/381,263, filed Aug. 30, 2016, each of which are incorporated herein by reference. To the extent appropriate, a claim of priority is made to each of the above-disclosed applications.

TECHNICAL FIELD

The invention relates to methods of using a glucagon (GCG) inhibitor or a glucagon receptor (GCGR) antagonist to treat or to slow the progression of severe insulin resistance, and/or reducing the therapeutic insulin dose in a patient in need thereof.

SEQUENCE LISTING

An official copy of the sequence listing is submitted concurrently with the specification electronically via EFS-Web as an ASCII formatted sequence listing with a file name of 10282WO01_SEQ_LIST_ST25, a creation date of Aug. 25, 2017, and a size of about 116 kilobytes. The sequence listing contained in this ASCII formatted document is part of the specification and is herein incorporated by reference in its entirety.

BACKGROUND

Glucagon is a 29 residue polypeptide hormone, which in cooperation with insulin, mediates homeostatic regulation of the amount of glucose in the blood. Glucagon primarily acts by stimulating certain cells, for example, liver cells, to release glucose when blood glucose levels fall to maintain normal blood glucose levels. The action of glucagon is opposite to that of insulin, which stimulates cells to take up and store glucose whenever blood glucose levels rise. Glucagon is produced in the alpha cells of the pancreas, whereas insulin is secreted from the neighboring beta cells.

It is an imbalance of glucagon and insulin that may play an important role in several diseases, such as diabetes mellitus and diabetic ketoacidosis. In particular, studies have shown that higher basal glucagon levels and lack of suppression of postprandial glucagon secretion contribute to diabetic conditions in humans (Muller et al. (1970), N Eng J Med, 283: 109-115).

It is believed that glucagon's effects on elevating blood glucose levels are mediated in part by the activation of certain cellular pathways following the binding of glucagon (GCG) to its receptor (designated GCGR). GCGR is a member of the secretin subfamily (family B) of G-protein-coupled receptors and is predominantly expressed in the liver. The binding of glucagon to its receptor triggers a G-protein signal transduction cascade, activating intracellular cyclic AMP and leading to an increase in glucose output through de novo synthesis (gluconeogenesis) and glycogen breakdown (glycogenolysis) (Wakelam et al., (1986) Nature, 323:68-71; Unson et al., (1989) Peptides, 10:1171-1177; and Pittner and Fain, (1991) Biochem. J., 277:371-378).

The action of glucagon can be suppressed by providing an antagonist, such as a small molecule inhibitor, a GCG antibody, or a GCGR antibody, as described herein. Anti-GCG antibodies are mentioned, e.g., in U.S. Pat. Nos. 4,206,199; 4,221,777; 4,423,034; 4,272,433; 4,407,965; 5,712,105; and in PCT publications WO2007/124463 and WO2013/081993. Anti-GCGR antibodies are described in U.S. Pat. Nos. 5,770,445, 7,947,809, and 8,545,847; European patent application EP2074149A2; EP patent EP0658200B1; US patent publications 2009/0041784; 2009/0252727; and 2011/0223160; and PCT publication WO2008/036341. Small molecule inhibitors of GCG or GCGR are mentioned, e.g. in WO 07/47676; WO 06/86488; WO 05/123688; WO 05/121097; WO 06/14618; WO 08/42223; WO 08/98244; WO 2010/98948; US 20110306624; WO 2010/98994; WO 2010/88061; WO 2010/71750; WO 2010/30722; WO 06/104826; WO 05/65680; WO 06/102067; WO 06/17055; WO 2011/07722; or WO 09/140342.

Severe insulin resistance syndromes are rare metabolic disorders in which patients do not respond well to insulin. Current treatments available for severe insulin resistance syndromes include regular feedings and very high doses of insulin in attempt to provide adequate glycemic control. Administration of IGF-I, while effective in the short term, failed to provide long-term glycemic control in patients with severe insulin resistance. Vestergaard et al., (1997) European Journal of Endocrinology, 136:475-482. Administration of recombinant leptin has shown some success in patients with Rabson-Mendenhall syndrome (RMS) by reducing blood glucose levels over several months. Cochran et al., (2004) Journal of Clinical Endocrinology and Metabolism, 89:1548-1554.

Given the absence of effective therapies to treat, or to slow the progression of severe insulin resistance disease, i.e., to extend the life and/or improve the quality of life of a patient having severe insulin resistance, there is a need to identify and explore the use of other agents for treating these diseases, such as the GCG/GCGR signaling pathway inhibitors and antagonists as described herein.

BRIEF SUMMARY

Provided herein are methods for treating a patient with a condition or disease characterized by severe insulin resistance by administering a GCG inhibitor or a GCGR antagonist, e.g. a pharmaceutical composition comprising a GCG inhibitor or GCGR antagonist. A GCG inhibitor or GCGR antagonist is a compound capable of blocking or inhibiting the glucagon receptor signaling pathway. The antagonist may take the form of a small molecule inhibitor, peptide inhibitor, CRISPR technology (Clustered regularly interspaced short palindromic repeats; CRISPR technology can generate GCGR knock-down or deletion of regulatory sequences affecting GCGR activity), an antisense inhibitor, DARPin, and a GCG or GCGR neutralizing monoclonal antibody. The GCG inhibitor or GCGR antagonist can be administered alone, in a pharmaceutical composition, or in conjunction with one or more therapeutic agents useful in treating a condition or disease associated with severe insulin resistance, or in treating one or more symptoms associated with the condition or disease, or in lowering blood glucose and/or ketones in a patient having a condition or disease associated with severe insulin resistance.

In some embodiments, methods are provided for lowering blood glucose levels and/or beta-hydroxybutyrate levels, or for decreasing ketonemia and/or ketoacidosis, or for treating a condition or disease associated with, or characterized in part by high blood glucose and/or ketonemia and/or ketoacidosis, or at least one symptom or complication associated with the condition or disease. In some aspects, the method comprises administering to a patient having severe insulin resistance a therapeutically effective amount of a composition comprising an inhibitor of GCG/GCGR signaling, such that blood glucose or beta-hydroxybutyrate levels are lowered or that the condition or disease is mediated, or at least one symptom or complication associated with the condition or disease is alleviated or reduced in severity. In some embodiments, the inhibitor of GCGR signaling is a GCGR antagonist, such as an anti-GCGR antibody. In some embodiments, the anti-GCGR antibody has a HCVR/LCVR sequence pair of SEQ ID NOs: 86/88. In some embodiments, the inhibitor of GCGR signaling is a GCG inhibitor, such as an anti-GCG antibody. In some embodiments, the anti-GCG antibody has a HCVR/LCVR sequence pair of SEQ ID NOs: 182/190. In some embodiments, the anti-GCG antibody has a HCVR/LCVR sequence pair of SEQ ID NOs: 166/174.

In some aspects, methods are provided for treating a patient with severe insulin resistance, wherein the patient exhibits elevated levels of blood glucose. The method comprises administering to the patient a therapeutically effective amount of a composition comprising a GCG inhibitor or a GCGR antagonist.

In some aspects, methods are provided for treating a patient with severe insulin resistance, wherein the patient does not exhibit elevated levels of blood glucose. The method comprises administering to the patient a therapeutically effective amount of a composition comprising a GCG inhibitor or a GCGR antagonist.

In some embodiments, methods are provided for reducing the amount and/or dosage of insulin necessary to treat a patient with severe insulin resistance, wherein the patient exhibits severe insulin resistance and/or elevated levels of blood glucose. In some aspects, the method comprises administering to the patient a therapeutically effective amount of a composition comprising a GCG inhibitor or a GCGR antagonist. In some aspects, the GCG inhibitor or GCGR antagonist is administered concomitantly with insulin. The amount and/or dosage of insulin may be reduced by about 30% to about 95%, or by about 90%, when administered concomitantly with an isolated human monoclonal antibody that binds specifically to the GCGR.

In some aspects, the GCGR antagonist can be an anti-GCGR antibody. The anti-GCGR antibody can inhibit or antagonize the GCGR. The anti-GCGR antibody can inhibit or block the GCGR signaling pathway. In some aspects, the GCG inhibitor can be an anti-GCG antibody. The anti-GCG antibody can inhibit binding of GCG to the GCGR.

In certain embodiments, the antibody or antigen-binding fragment specifically binds hGCGR, and comprises the heavy and light chain CDR domains contained within heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148.

In certain embodiments, the antibody or antigen-binding fragment comprises the heavy and light chain CDR domains contained within the HCVR/LCVR amino acid sequence pair of SEQ ID NOs: 86/88.

In certain embodiments, the antibody or antigen-binding fragment comprises a HCVR/LCVR amino acid sequence pair of SEQ ID NOs: 86/88.

In one embodiment, the human antibody or antigen-binding fragment of a human antibody that binds hGCGR, comprises a heavy chain variable region (HCVR) having an amino acid sequence selected from the group consisting of SEQ ID NO: 2, 18, 34, 50, 66, 70, 86, 90, 106, 110, 126, 130 and 146, or a substantially similar sequence thereof having at least 90%, at least 95%, at least 98% or at least 99% sequence identity.

In one embodiment, the human antibody or antigen-binding fragment of a human antibody that binds hGCGR comprises a light chain variable region (LCVR) having an amino acid sequence selected from the group consisting of SEQ ID NO: 10, 26, 42, 58, 68, 78, 88, 98, 108, 118, 128, 138 and 148, or a substantially similar sequence thereof having at least 90%, at least 95%, at least 98% or at least 99% sequence identity.

In certain embodiments, the human antibody or fragment thereof that binds hGCGR comprises a HCVR/LCVR amino acid sequence pair selected from the group consisting of SEQ ID NO: 2/10, 18/26, 34/42, 50/58, 66/68, 70/78, 86/88, 90/98, 106/108, 110/118, 126/128, 130/138, and 146/148. In certain embodiments, the HCVR/LCVR amino acid sequence pair is selected from the group consisting of SEQ ID NO: 34/42, 70/78, 86/88, 110/118 and 126/128.

In certain embodiments, the isolated human antibody or an antigen-binding fragment thereof that binds specifically to hGCGR comprises a HCVR comprising the three heavy chain CDRs (HCDR1, HCDR2 and HCDR3) contained within the HCVR sequence selected from the group consisting of SEQ ID NO: 2, 18, 34, 50, 66, 70, 86, 90, 106, 110, 126, 130 and 146; and/or a LCVR comprising the three light chain CDRs (LCDR1, LCDR2 and LCDR3) contained within the LCVR sequences selected from the group consisting of SEQ ID NO: 10, 26, 42, 58, 68, 78, 88, 98, 108, 118, 128, 138 and 148.

In certain embodiments, the methods provided herein contemplate the use of an isolated human antibody or antigen-binding fragment thereof that binds hGCGR comprising a HCDR3 domain having an amino acid sequence selected from the group consisting of SEQ ID NO: 8, 24, 40, 56, 76, 96, 116 and 136, or a substantially similar sequence thereof having at least 90%, at least 95%, at least 98% or at least 99% sequence identity; and/or a LCDR3 domain having an amino acid sequence selected from the group consisting of SEQ ID NO: 16, 32, 48, 64, 84, 104, 124 and 144, or a substantially similar sequence thereof having at least 90%, at least 95%, at least 98% or at least 99% sequence identity.

In one embodiment, the methods provided herein contemplate use of an antibody or fragment thereof that further comprises a HCDR1 domain having an amino acid sequence selected from the group consisting of SEQ ID NO: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 82, 102, 122 and 142, or a substantially similar sequence thereof having at least 90%, at least 95%, at least 98% or at least 99% sequence identity.

In one embodiment, the antibody or antigen-binding fragment of an antibody comprises:
(a) a HCDR3 domain having an amino acid sequence selected from the group consisting of SEQ ID NO: 8, 24, 40, 56, 76, 96, 116 and 136; and
(b) a LCDR3 domain having an amino acid sequence selected from the group consisting of SEQ ID NO: 16, 32, 48, 64, 84, 104, 124 and 144.

In a related embodiment, the antibody or antigen-binding fragment of the antibody further comprises:
(c) a HCDR1 domain having an amino acid sequence selected from the group consisting of SEQ ID NO: 4, 20, 36, 52, 72, 92, 112 and 132;
(d) a HCDR2 domain having an amino acid sequence selected from the group consisting of SEQ ID NO: 6, 22, 38, 54, 74, 94, 114 and 134;
(e) a LCDR1 domain having an amino acid sequence selected from the group consisting of SEQ ID NO: 12, 28, 44, 60, 80, 100, 120 and 140; and
(f) a LCDR2 domain having an amino acid sequence selected from the group consisting of SEQ ID NO: 14, 30, 46, 62, 82, 102, 122 and 142.

In one embodiment, the antibody or antigen-binding fragment thereof comprises a HCVR comprising a HCDR1 domain having an amino acid sequence selected from one of SEQ ID NO: 4, 20, 36, 52, 72, 92, 112 and 132; a HCDR2 domain having an amino acid sequence selected from one of SEQ ID NO: 6, 22, 38, 54, 74, 94, 114 and 134; a HCDR3 domain having an amino acid sequence selected from one of SEQ ID NOs: 8, 24, 40, 56, 76, 96, 116 and 136; and a LCVR comprising a LCDR1 domain having an amino acid sequence selected from one of SEQ ID NO: 12, 28, 44, 60, 80, 100, 120 and 140; a LCDR2 domain having an amino acid sequence selected from one of SEQ ID NO: 14, 30, 46, 62, 82, 102, 122 and 142; and a LCDR3 domain having an amino acid sequence selected from one of SEQ ID NO: 16, 32, 48, 64, 84, 104, 124 and 144.

In certain embodiments, the human antibody or antigen-binding fragment of a human antibody that binds to human GCGR comprises a HCDR3/LCDR3 amino acid sequence pair selected from the group consisting of SEQ ID NO: 8/16, 24/32, 40/48, 56/64, 76/84, 86/88, 96/104, 116/124 and 136/144. Non-limiting examples of anti-GCGR antibodies having these HCDR3/LCDR3 pairs are the antibodies designated H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P, respectively.

In one embodiment, the isolated antibody or antigen-binding fragment thereof useful according to the methods provided herein, that specifically binds to GCG and neutralizes at least one activity associated with GCG, comprises:
(a) three heavy chain complementarity determining regions (HCDR1, HCDR2 and HCDR3) contained within a heavy chain variable region (HCVR) amino acid sequence selected from the group consisting of SEQ ID NOs: 150, 166, 182, 198, 214, 230, 246, 262, 278 and 294; and (b) three light chain CDRs (LCDR1, LCDR2 and LCDR3) contained within a light chain variable region (LCVR) amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises an HCVR having an amino acid sequence selected from the group consisting of SEQ ID NOs: 150, 166, 182, 198, 214, 230, 246, 262, 278 and 294 and a LCVR having an amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises a HCVR/LCVR amino acid sequence pair selected from the group consisting of SEQ ID NOs: 150/158; 166/174; 182/190; 198/206; 214/222; 230/238; 246/254; 262/270; 278/286 and 294/302.

In some embodiments, the HCVR/LCVR amino acid sequence pair comprises SEQ ID NOs: 166/174.

In some embodiments, the HCVR/LCVR amino acid sequence pair comprises SEQ ID NOs: 182/190.

In one embodiment, the isolated antibody or antigen-binding fragment thereof useful according to the methods provided herein, comprises:
(a) a HCDR1 domain having an amino acid sequence selected from the group consisting of SEQ ID NOs: 152, 168, 184, 200, 216, 232, 248, 264, 280, and 296;
(b) a HCDR2 domain having an amino acid sequence selected from the group consisting of SEQ ID NOs: 154, 170, 186, 202, 218, 234, 250, 266, 282, and 298;
(c) a HCDR3 domain having an amino acid sequence selected from the group consisting of SEQ ID NOs: 156, 172, 188, 204, 220, 236, 252, 268, 284, and 300;
(d) a LCDR1 domain having an amino acid sequence selected from the group consisting of SEQ ID NOs: 160, 176, 192, 208, 224, 240, 256, 272, 288, and 304;
(e) a LCDR2 domain having an amino acid sequence selected from the group consisting of SEQ ID NOs: 162, 178, 194, 210, 226, 242, 258, 274, 290, and 306; and
(f) a LCDR3 domain having an amino acid sequence selected from the group consisting of SEQ ID NOs: 164, 180, 196, 212, 228, 244, 260, 276, 292, and 308.

In one embodiment, the isolated antibody or antigen-binding fragment thereof useful according to the methods provided herein, comprises:
(a) a HCDR1 domain comprising the amino acid sequence of SEQ ID NO: 168;
(b) a HCDR2 domain comprising the amino acid sequence of SEQ ID NO: 170;
(c) a HCDR3 domain comprising the amino acid sequence of SEQ ID NO: 172;
(d) a LCDR1 domain comprising the amino acid sequence of SEQ ID NO: 176;
(e) a LCDR2 domain comprising the amino acid sequence of SEQ ID NO: 178; and
(f) a LCDR3 domain comprising the amino acid sequence of SEQ ID NO: 180.

In one embodiment, the isolated antibody or antigen-binding fragment thereof useful according to the methods provided herein, comprises:
(a) a HCDR1 domain comprising the amino acid sequence of SEQ ID NO: 184;
(b) a HCDR2 domain comprising the amino acid sequence of SEQ ID NO: 186;
(c) a HCDR3 domain comprising the amino acid sequence of SEQ ID NO: 188;
(d) a LCDR1 domain comprising the amino acid sequence of SEQ ID NO: 192;
(e) a LCDR2 domain comprising the amino acid sequence of SEQ ID NO: 194; and
(f) a LCDR3 domain comprising the amino acid sequence of SEQ ID NO: 196.

Also useful according to the methods provided herein are antibodies or antigen-binding fragments thereof that specifically bind GCG, comprising a heavy chain CDR1 (HCDR1) comprising an amino acid sequence selected from any of the HCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR2 (HCDR2) comprising an amino acid sequence selected from any of the HCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR3 (HCDR3) comprising an amino acid sequence selected from any of the HCDR3 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR1 (LCDR1) comprising an amino acid sequence selected from any of the LCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR2 (LCDR2) comprising an amino acid sequence selected from any of the LCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR3 (LCDR3) comprising an amino acid sequence selected from any of the LCDR3 amino acid sequences listed herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising an HCDR3 and an LCDR3 amino acid sequence pair (HCDR3/LCDR3) comprising any of the HCDR3 amino acid provided herein paired with any of the LCDR3 amino acid sequences provided herein. According to certain embodiments, the antibodies, or antigen-binding fragments thereof, comprise an HCDR3/LCDR3 amino acid sequence pair contained within any of the exemplary anti-GCG antibodies provided herein. In certain embodiments, the HCDR3/LCDR3 amino acid sequence pair comprises SEQ ID NOs: 172/180.

Also useful according to the methods provided herein are antibodies or antigen-binding fragments thereof that specifically bind GCG, comprising a set of six CDRs (i.e., HCDR1-HCDR2-HCDR3-LCDR1-LCDR2-LCDR3) contained within any of the exemplary anti-GCG antibodies provided herein. In certain embodiments, the HCDR1/HCDR2/HCDR3/LCDR1/LCDR2/LCDR3 amino acid sequence set comprises SEQ ID NOs: 168/170/172/176/178/180. In certain embodiments, the HCDR1/HCDR2/HCDR3/LCDR1/LCDR2/LCDR3 amino acid sequence set comprises SEQ ID NOs: 184/186/188/192/194/196.

In a related embodiment, the antibodies, or antigen-binding fragments thereof that specifically bind GCG, comprise a set of six CDRs (i.e., HCDR1/HCDR2/HCDR3/LCDR1/LCDR2/LCDR3) contained within an HCVR/LCVR amino acid sequence pair as defined by any of the exemplary anti-GCG antibodies provided herein. For example, the antibodies or antigen-binding fragments thereof that specifically bind GCG, comprise the HCDR1/HCDR2/HCDR3/LCDR1/LCDR2/LCDR3 amino acid sequences set contained within an HCVR/LCVR amino acid sequence pair selected from the group consisting of: 166/174; 182/190; 198/206; 214/222; 230/238; 246/254; 262/270; 278/286 and 294/302.

Non-limiting examples of antibodies that specifically bind GCG and comprise the CDR sequences provided above, include HIH059P, H4H10223P, H4H10231P, H4H10232P, H4H10236P, H4H10237P, H4H10238P, H4H10250P, H4H10256P, and H4H10270P.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, (1991) "Sequences of Proteins of Immunological Interest," National Institutes of Health, Bethesda, Md.; Al-Lazikani et al., (1997) J. Mol. Biol. 273:927-948; and Martin et al., (1989) Proc. Natl. Acad. Sci. USA 86:9268-9272. Public databases are also available for identifying CDR sequences within an antibody.

In some embodiments, a patient having severe insulin resistance may suffer from one of the conditions or diseases selected from the following: Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, and a condition or disease associated with the presence of one or more gene variants reported to cause severe insulin resistance. In some embodiments, insulin degrading protease activity is detected in the patient sera. In some embodiments, neutralizing anti-insulin antibodies or anti-insulin receptor antibodies are detected in the patient sera. In some patients, severe insulin resistance arises in the context of autoimmune destruction of adipocytes leading to lipodystrophy.

In some aspects, the gene variant associated with severe insulin resistance is selected from the following: INSR, PSMD6, ADRA2A, AGPAT2 (associated with lipodystrophy and insulin resistance), AKT2, APPL1, BBS1 (associated with Bardet-Beidl Syndrome 1), BSCL2, CIDEC, GRB10, IRS2, KLF14, LEP, LEPR, LMNA (associated with lipodystrophy), MC4R, PCNT, PIK2CA, POLD1 (associated with lipodystrophy), PPARG, PTPRD, PTRF (associated with lipodystrophy), RASGRP1, TBC1D4, and TCF7L2.

In some aspects, the composition comprising the glucagon/GCGR antagonist is administered to a patient in combination with at least one additional therapeutic agent. The additional therapeutic agent can be any agent that alleviates or reduces the symptoms and signs associated with severe insulin resistance. In some embodiments, at least one additional therapeutic agent is selected from the following: insulin, a biguanide, hIGF1, leptin, metraleptin, pioglitazone, vildagliptin, acarbose, alpha-glycosidase inhibitors, L-arginine, dipeptidyl-peptidase-4 inhibitors, insulin secretagogues, amylin receptor agonists, insulin sensitizers, FGF21, SGLT2 inhibitors, SGLT1 inhibitors, GLP-1 receptor agonists, GLP-1 receptor activators, a second GCG inhibitor, and a second GCGR antagonist. In some aspects, the insulin secretagogue is selected from sulfonylureas, ATP-sensitive K channel antagonists, and meglitinides. In some aspects, the insulin sensitizer is selected from thiazolidinedione and rosiglitazone. In some aspects, the additional therapeutic agent can be an agent that increases energy expenditure and/or brown fat activity, such as, for example, β3 adrenergic agonists (such as miglitol), NPR1 agonists, NPR3 antagonists, triiodothyronine, thiazolidinediones, VEGF, Irisin, meteorin-like, natriuretic peptides, orexin, norepinephrine, T4, bile acids, FGF-21, menthol, slit2-C BMP7, BMP8β, and FnIII domain-like/Tn3 scaffolds (binding molecules based on the third fibronectin type III domain of human tenascin C).

Other objects and advantages will become apparent from a review of the ensuing detailed description.

BRIEF DESCRIPTION OF THE FIGURES

In FIG. 1A, mice treated with an insulin receptor antagonist, 5961, and an antibody to the GCGR, H4H1327P, (open triangles) exhibited a rise in blood glucose levels relative to blood glucose levels in mice treated with the insulin receptor antagonist and an isotype control antibody (closed squares). In FIG. 1B, treatment of mice with 5961 demonstrated an increase in insulin levels over time (closed squares), even in the presence of H4H1327P (open triangles). In FIG. 1C, mice treated with H4H1327P, in the absence (open circles) or presence of 5961 (open triangles), exhibited higher levels of glucagon than the isotype control treated (closed circles) or 5961 treated (closed squares) mice. In FIG. 1D, mice treated with 5961 and H4H1327P (open triangles) maintained beta-hydroxybutyrate levels like those of the isotype control treated (closed circles) and antibody alone control (open circles). Mice treated with the insulin receptor antagonist in the absence of the GCGR antibody exhibited higher levels of beta-hydroxybutyrate (closed squares) relative to other treatment groups. Body weights among the four treatment groups were unchanged. See FIG. 1E.

In FIG. 2B, treatment with 5961 caused insulin levels to rise (closed squares), and subsequent treatment with the GCGR antibody, H4H1327P, did not lower the insulin levels (open triangles). As shown in FIG. 2C, glucagon levels were higher in mice treated with H4H1327P (open circles), and still higher in mice treated with both the antibody and 5961 (open triangles). FIG. 2D shows plasma beta-hydroxybutyrate levels were elevated in response to treatment with 5961 (closed squares), but within days of treatment with H4H1327P, the levels dropped to those of the untreated control and antibody alone control (open triangles). FIG. 2E shows amino acids levels were higher in mice treated with H4H1327P (open circles), and still higher in mice treated with both the antibody and 5961 (open triangles). No changes in body weight were observed. See FIG. 2F.

DESCRIPTION

Figure 1A:
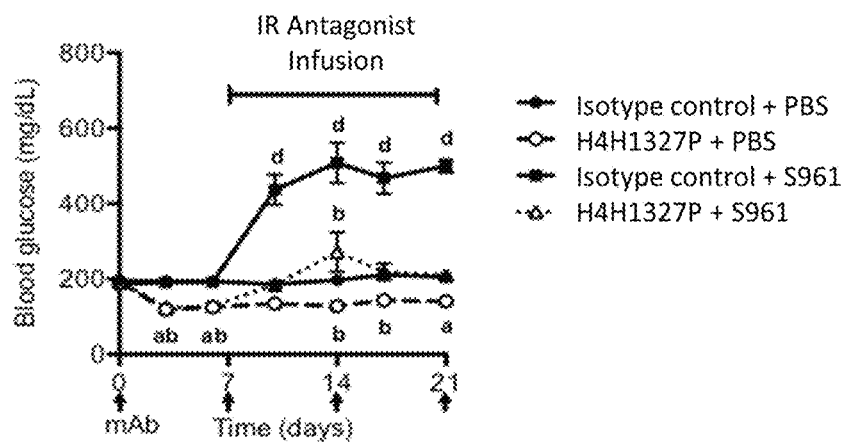
FIGS. 1A-1E show blood glucose levels, insulin levels, glucagon levels, and B-hydroxybutyrate levels, as well as body weights, in a mouse model of severe insulin resistance.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

GENERAL DESCRIPTION

Severe insulin resistance occurs in association with a variety of physiological and pathophysiological states. Clinical findings include hyperinsulinemia, acanthosis nigricans, ovarian hyperandrogenism, polycystic ovaries, and eventual hyperglycemia and, in rare instances, patients can develop ketoacidosis. Although there is no consensus definition for severe insulin resistance to distinguish it from the more common insulin resistance, syndromic insulin resistance has been classified as either primary insulin-signaling defects (insulin receptoropathies or partial disruption of the insulin signaling pathway) or insulin resistance secondary to adipose tissue abnormalities (severe obesity or lipodystrophy). See Semple et al., (2011), Genetic Syndromes of Severe Insulin Resistance, Endocrine Reviews, 32(4):498-514.

Evidence of severe insulin resistance is seen in patients who require exogenous insulin at doses of more than 100 to 200 units per day, or in patients with chronically elevated circulating levels of endogenous insulin. Moller and Flier, (1991) New England Journal of Medicine, 325:938-948. Fasting insulin levels above 50-70 μU/mL or peak (post-oral glucose tolerance testing) insulin levels above 350 μU/mL suggest severe insulin resistance. Insulin sensitivity index values below $2\times10^4$ μU/mL·min typically occur in the presence of severe insulin resistance. Patients with severe insulin resistance also exhibit a glucose disposal rate below 2 mg/kg·min. See Tritos and Mantzoros, (1998) Journal of Clinical Endocrinology and Metabolism, 83:3025-3030.

Insulin interacts with insulin receptors on the plasma membrane of target cells. The insulin receptor is a transmembrane tyrosine kinase receptor, and functions to regulate glucose homeostasis. The insulin receptor consists of two α subunits containing the site for insulin binding, and two β subunits containing the tyrosine kinase domain; the subunits are connected by disulfide bridges to form a 350 kDa β-α-α-β tetramer. Two isoforms of the receptor exist, an isoform with exon 11 (IR-B) and an isoform without exon 11 (IR-A), and the levels of the isoforms are expressed differently in various tissues. The IR-B isoform exhibits higher more efficient signaling activity the IR-A isoform, and the IR-B isoform is predominantly expressed in the liver, adipose tissue, and muscle tissue. The IR-A isoform is expressed in CNS cells and hematopoietic cells, and has slightly higher insulin binding affinity.

The tyrosine kinase activity of the activated insulin receptor is responsible for transmembrane signaling of glucose transport and regulation of glucose homeostasis.

Severe insulin resistance is typically associated with insulin receptor mutations, resulting in diminished expression on the cell surface or in the signaling capacity of the receptor. Other mutations include defects in receptor binding affinity or mutations in proteins involved in the insulin signal transduction pathway, e.g. the conserved regions of the tyrosine kinase domain of the insulin receptor.

Patients having severe insulin resistance may suffer from a condition or disease selected from the following: Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, or Bardet-Biedl syndrome.

Genetic and acquired states of severe insulin resistance are rare disorders in which the body's tissues and organs do not respond properly to insulin. Clinical findings associated with severe insulin resistance include growth retardation, organomegaly, impaired development of skeletal and adipose tissue, soft tissue overgrowth, diabetes, hepatic steatosis, acanthosis nigricans, ovarian hyperandrogenism, and hirsutism. Laboratory findings include hyperinsulinemia, reduced insulin clearance, hyperglycemia, dyslipidemia, and elevated androgens. Each of the various syndromes associated with severe insulin resistance have unique features, in addition to some or all of the general clinical and laboratory features.

Donohue syndrome (DS, also called Leprechaunism) and Rabson-Mendenhall syndrome (RMS) are rare autosomal recessive conditions in which both alleles for the insulin receptor are abnormal, and patients fail to respond to endogenous and exogenous insulin. Individuals with DS and RMS are underdeveloped before birth, then fail to thrive as infants. Patients present with extremely high levels of circulating insulin, up to 1000 times the normal level. The primary metabolic consequence of DS is fasting hypoglycemia, and secondarily, post-prandial hyperglycemia. Individuals diagnosed with DS usually die before one year of age and do not develop diabetic ketoacidosis. Individuals with RMS also experience fasting hypoglycemia and typically survive infancy, but over time, develop severe and intractable diabetic ketoacidosis and a decline in insulin levels.

Ketonemia occurs when ketone bodies are formed by the breakdown of fatty acids and the deamination of amino acids and accumulate in the blood. If this continues untreated, the patients can then continue on to diabetic ketoacidosis. Beta-hydroxybutyrate and acetoacetic acid are two of the more common ketones, and elevated levels can be used to gauge the severity of ketonemia and an indicator of ketoacidosis.

Type A insulin resistance syndrome is another rare disorder characterized by severe insulin resistance, and symptoms typically present in adolescence for females, or adulthood for males. Females present with primary amenorrhea or oligomenorrhea, ovarian cysts, hirsutism, and acanthosis nigricans, but are typically not overweight. Affected males present when they develop diabetes mellitus. As with DS and RMS, insulin receptor gene mutations are responsible for Type A insulin resistance syndrome.

Lipodystrophy refers to a group of disorders characterized by abnormal adipose distribution, utilization, and metabolism, due to defects in the insulin receptor itself or downstream components of the insulin signaling cascade. Patients with lipodystrophy present with a generalized or partial absence of adipose tissue, insulin resistance (with or without diabetes), significant dyslipidaemia, and fatty liver. Some lipodystrophy syndromes, like Berardinelli-Seip syndrome, are inherited, while others, including Lawrence syndrome, are acquired, sometimes after an infectious prodrome. Additional lipodystrophy syndromes include Kobberling-Dunnigan syndrome, lipodystrophy with other dysmorphic features, and cephalothoracic lipodystrophy.

Type B insulin resistance syndrome is different from DS, RMS, and Type A insulin resistance syndrome in that the former is associated with the presence of serum autoantibodies against the insulin receptor, and may occur in the context of an autoimmune disease. Symptoms are similar to other insulin resistance syndromes, and include non-ketotic and severely insulin-resistant diabetes, acanthosis nigricans, and hirsutism, in addition to occasional paradoxal hypoglycemia.

HAIR-AN (hyperandrogenism, insulin resistance, and acanthosis nigricans) syndrome presents in young women, typically obese, with insulin resistance taking different forms; some individuals have high concentrations of insulin but normal levels of glucose, while others present with diabetic symptoms. Unlike the rarity of other syndromes of severe insulin resistance, HAIR-AN syndrome is estimated to affect around 5% of adolescent girls worldwide. The syndrome is associated with mutations of the tyrosine kinase domain of the insulin receptor gene.

Pseudoacromegaly presents with severe insulin resistance in association with acromegaloidism, and is possibly caused by a defect in the insulin signaling pathway or from high insulin levels signaling through the IGF-1 receptor.

Other severe insulin resistance syndromes include Alstrom syndrome, myotonic dystrophy, and Werner's syndrome, to name a few.

In some patients, the condition or disease is associated with the presence of a gene variant reported to cause severe insulin resistance. Exemplary gene variants include INSR, PSMD6, ADRA2A, AGPAT2 (associated with lipodystrophy and insulin resistance), AKT2, APPL1, BBS1 (associated with Bardet-Beidl Syndrome 1), BSCL2, CIDEC, GRB10, IRS2, KLF14, LEP, LEPR, LMNA (associated with lipodystrophy), MC4R, PCNT, PIK2CA, POLD1 (associated with lipodystrophy), PPARG, PTPRD, PTRF (associated with lipodystrophy), RASGRP1, TBC1D4, and TCF7L2.

In some patients, insulin degrading protease activity is detected in the patient sera. In some patients, neutralizing anti-insulin antibodies or anti-insulin receptor antibodies are detected in the patient sera. In some patients, severe insulin resistance arises in the context of autoimmune destruction of adipocytes leading to lipodystrophy.

Patients with severe insulin resistance eventually develop hyperglycemia and, in some syndromes, ketoacidosis. For example, in patients with RMS, insulin levels start out very high early in life, even during periods of paradoxical fasting hypoglycemia. As the disease progresses, insulin levels while still elevated, drop. In addition, partially oxidized fatty acid levels increase, indicating that insulin is unable to suppress the release of fatty acids from adipocytes, ultimately resulting in constant ketoacidosis. Likewise, constant hyperglycemia results as insulin levels are no longer capable of suppressing hepatic glucose production and release. However, continuous infusion of extremely high concentrations of insulin (9.5 U/kg hr) can reverse increased fatty acid oxidation and block ketonuria. Longo et al., (1991) Journal of Clinical Endocrinology & Metabolism, 84:2623-2629. In addition, hypertriglyceridemia and low high-density lipoprotein cholesterol levels are associated with severe insulin resistance.

Patients with severe insulin resistance syndromes have normal or even slightly elevated plasma glucagon levels despite hyperglycemia. West et al., (1975) Arch. Dis. Child., 50(9):703-708; Desbois-Mouthon et al., (1997) Pediatr. Res., 42(1):72-77. The hyperglycemia results from enhanced hepatic glucose output due to lack of insulin suppression and abnormally high glucagon signaling.

To date, there have been no studies examining the effects of antagonizing the GCG/GCGR signaling pathway on severe insulin resistance conditions or diseases. The studies described in the Examples use an antagonist of GCGR, as an exemplary inhibitor of the GCG/GCGR signaling pathway, in a mouse model of severe insulin resistance to demonstrate the effects on blood glucose levels and ketonemia, as measured by plasma beta-hydroxybutyrate levels, over several weeks of treatment.

Definitions

The "glucagon receptor", also referred to herein as "GCGR", belongs to the G protein-coupled receptor class 2 family and consists of a long amino terminal extracellular domain, seven transmembrane segments, and an intracellular C-terminal domain. Glucagon receptors are notably expressed on the surface of hepatocytes where they bind to glucagon and transduce the signal provided thereby into the cell. Accordingly, the term "glucagon receptor" also refers to one or more receptors that interact specifically with glucagon to result in a biological signal. DNA sequences encoding glucagon receptors of rat and human origin have been isolated and disclosed in the art (EP0658200B1). The murine and cynomolgus monkey homologues have also been isolated and sequenced (Burcelin, et al., (1995) Gene 164:305-310); McNally et al., (2004) Peptides 25:1171-1178). As used herein, "glucagon receptor" and "GCGR" are used interchangeably. The expression "GCGR", "hGCGR" or fragments thereof, as used herein, refers to the human GCGR protein or fragment thereof, unless specified as being from a non-human species, e.g. "mouse GCGR", "rat GCGR", or "monkey GCGR".

The phrase "GCGR antagonist" refers to an inhibitor, antagonist, or inverse agonist of the GCGR signaling pathway. A "GCG inhibitor" may prevent the binding of glucagon to the receptor. A GCGR inhibitor may also prevent the binding of glucagon to the receptor. However, both effectively block or attenuate activation of the receptor, or may interfere with the signaling cascade downstream of the GCGR activation.

A GCGR antagonist is able to bind to the glucagon receptor and thereby antagonize the activity of GCG mediated by the GCGR. Inhibiting the activity of GCG by antagonizing the binding and activity of GCG at the GCGR reduces the rate of gluconeogenesis and glycogenolysis, and the concentration of glucose in plasma. Methods by which to determine the binding of a supposed antagonist with the glucagon receptor are known in the art and means by which to determine the interference with glucagon activity at the glucagon receptor are publicly available; see, e.g., S. E. de Laszlo et al., (1999) Bioorg. Med. Chem. Lett. 9:641-646. Contemplated as useful herein are GCGR antagonists or GCG inhibitors having as a functional component thereof a small molecule compound, or in other words a low molecular weight organic compound. A small molecule is typically less than 800 Daltons. Additionally, CRISPR technology can be used to knock-down GCG or GCGR expression.

The terms "inhibitor" or "antagonist" include a substance that retards or prevents a chemical or physiological reaction or response. Common inhibitors or antagonists include but are not limited to antisense molecules, antibodies, small molecule inhibitors, peptide inhibitors, DARPins, Spiegelmers, aptamers, engineered Fn type-III domains, and their derivatives.

An example of a GCG inhibitor or a GCGR signaling pathway antagonist includes, but is not limited to, an antibody (human or humanized), or an antigen binding portion thereof, to GCG or GCGR, that blocks binding or inhibits the activity of the GCGR signaling pathway. Exemplary GCGR antagonists that may be used in the methods described herein include isolated human monoclonal antibody or antigen-binding fragment thereof comprising: (a) a HCVR having an amino acid sequence selected from the group consisting of SEQ ID NO: 2, 18, 34, 50, 66, 70, 86, 90, 106, 110, 126, 130 and 146; and/or (b) a LCVR having an amino acid sequence selected from the group consisting of SEQ ID NO: 10, 26, 42, 58, 68, 78, 88, 98, 108, 118, 128, 138 and 148. Exemplary GCG inhibitors that may be used in the methods described herein include isolated human monoclonal antibody or antigen-binding fragment thereof comprising: (a) a HCVR having an amino acid sequence selected from the group consisting of SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302.

A "therapeutically effective dose" is a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the phrase "substantially identical" is meant a protein sequence having at least 95% identity to an HCVR having an amino acid sequence selected from the group consisting of SEQ ID NO: 2, 18, 34, 50, 66, 70, 86, 90, 106, 110, 126, 130 and 146; and/or (b) a LCVR having an amino acid sequence selected from the group consisting of SEQ ID NO: 10, 26, 42, 58, 68, 78, 88, 98, 108, 118, 128, 138 and 148, and capable of binding GCGR and inhibiting the biological activity of GCGR. The phrase "substantially identical" is also meant a protein sequence having at least 95% identify to an HCVR having an amino acid sequence selected from the group consisting of the amino acid sequences SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302, and capable of binding GCG and inhibiting the biological activity of GCG.

The terms "identity" or "homology" are construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The term "treating" (or "treat" or "treatment") refers to processes involving a slowing, interrupting, inhibiting, arresting, controlling, stopping, reducing, ameliorating, or reversing the progression, duration, or severity of an existing symptom, disorder, condition, or disease, but does not necessarily involve a total elimination of all disease-related symptoms, conditions, or disorders through use of a GCG inhibitor or GCGR antagonist as described herein. Furthermore, "treating", "treatment" or "treat" refers to an approach for obtaining beneficial or desired results including clinical results, which include, but are not limited to, one or more of the following: inhibiting, delaying or preventing the progression of severe insulin resistance; inhibiting, delaying or preventing the progression of a disease associated with severe insulin resistance, or characterized by elevated plasma insulin levels, elevated blood glucose levels, and/or ketonemia or ketoacidosis (as measured by elevated beta-hydroxybutyrate levels), such as in Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, or a condition or disease associated with the presence of a gene variant reported to cause severe insulin resistance; or inhibiting, preventing, or ameliorating at least one symptom associated with a disease associated with severe insulin resistance; or lowering blood glucose levels and/or beta-hydroxybutyrate levels (as an indicator of ketoacidosis), such that the condition or disease associated with high blood glucose levels and ketonemia is mediated, or at least one symptom or complication associated with the condition or disease is alleviated or reduced in severity. "Treatment" or "treating", as used herein, also refers to increasing the quality of life of those suffering from the disease, decreasing the dose of other medications required to treat the disease and/or prolonging survival of patients. For example, "treatment" or "treating" can include reducing the amount and/or dosage of insulin necessary to treat a patient with severe insulin resistance.

The phrase "insulin resistance" is a state in which a greater than normal amount of insulin is required to elicit a quantitatively normal response. The phrase "severe insulin resistance" generally refers to a clinical entity that typically presents with near-normal or elevated blood glucose levels despite marked elevations in endogenous insulin secretion and/or plasma levels of insulin. Evidence of severe insulin resistance is seen in patients who require exogenous insulin at doses of more than 100 to 200 units per day, or in patients with chronically elevated circulating levels of endogenous insulin. Moller and Flier, (1991) New England Journal of Medicine, 325:938-948. Fasting insulin levels above 50-70 µU/mL or peak (post-oral glucose tolerance testing) insulin levels above 350 µU/mL suggest severe insulin resistance. Insulin sensitivity index values below $2 \times 10^4$ µU/mL·min typically occur in the presence of severe insulin resistance. Patients with severe insulin resistance also exhibit a glucose disposal rate below 2 mg/kg·min. See Tritos and Mantzoros, (1998) Journal of Clinical Endocrinology and Metabolism, 83:3025-3030.

GCG/GCGR Signaling Pathway Inhibitors

Provided herein are GCG inhibitors and GCGR antagonists for the treatment of conditions or diseases characterized by severe insulin resistance. In some embodiments, the antagonist is an inhibitor of glucagon. In some embodiments, the antagonist is an inhibitor of GCGR. In some embodiments, the GCGR antagonist is MK-0893, PF-06291874, LGD-6972, or LY2409021.

In some embodiments, the antagonist comprises an antibody capable of binding GCG or GCGR, or a fragment thereof. In some embodiments, the signaling pathway is inhibited by the interruption of GCG or GCGR expression, by, for example, using CRISPR technology or antisense.

In some embodiments, the GCG inhibitor or GCGR antagonist is an antisense molecule, antibody, small molecule inhibitor, peptide inhibitor, DARPin, Spiegelmer, aptamer, engineered Fn type-III domains, or a derivative thereof.

Anti-GCGR Antibodies, Anti-GCG Antibodies, and Antibody Fragments

In some embodiments, the GCGR antagonist is an antibody or antibody fragment as disclosed in U.S. Pat. No. 8,545,847, incorporated by reference herein in its entirety. Antibodies disclosed therein are provided in Table 1.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H1345N | 2 | 4 | 6 | 8 | 10 | 12 | 14 | 16 |
| H4H1617N | 18 | 20 | 22 | 24 | 26 | 28 | 30 | 32 |
| H4H1765N | 34 | 36 | 38 | 40 | 42 | 44 | 46 | 48 |
| H4H1321B | 50 | 52 | 54 | 56 | 58 | 60 | 62 | 64 |
| H4H1321P | 66 | 52 | 54 | 56 | 68 | 60 | 62 | 64 |
| H4H1327B | 70 | 72 | 74 | 76 | 78 | 80 | 82 | 84 |
| H4H1327P | 86 | 72 | 74 | 76 | 88 | 80 | 82 | 84 |
| H4H1328B | 90 | 92 | 94 | 96 | 98 | 100 | 102 | 104 |
| H4H1328P | 106 | 92 | 94 | 96 | 108 | 100 | 102 | 104 |
| H4H1331B | 110 | 112 | 114 | 116 | 118 | 120 | 122 | 124 |
| H4H1331P | 126 | 112 | 114 | 116 | 128 | 120 | 122 | 124 |
| H4H1339B | 130 | 132 | 134 | 136 | 138 | 140 | 142 | 144 |
| H4H1339P | 146 | 132 | 134 | 136 | 148 | 140 | 142 | 144 |

Additional GCGR antibodies or antibody fragments contemplated as useful herein include those disclosed in U.S. Pat. Nos. 5,770,445 and 7,947,809; European patent application EP2074149A2; EP patent EP0658200B1; U.S. patent publications 2009/0041784; 2009/0252727; and 2011/0223160; and PCT publication WO2008/036341. The patents and publications are incorporated by reference herein in their entirety.

In some embodiments, the GCG inhibitor is an antibody or antibody fragment thereof as disclosed in U.S. 2016/0075778, incorporated by reference herein in its entirety. Antibodies disclosed therein are provided in Table 2.

TABLE 2

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H059P | 150 | 152 | 154 | 156 | 158 | 160 | 162 | 164 |
| H4H10223P | 166 | 168 | 170 | 172 | 174 | 176 | 178 | 180 |
| H4H10231P | 182 | 184 | 186 | 188 | 190 | 192 | 194 | 196 |
| H4H10232P | 198 | 200 | 202 | 204 | 206 | 208 | 210 | 212 |
| H4H10236P | 214 | 216 | 218 | 220 | 222 | 224 | 226 | 228 |
| H4H10237P | 230 | 232 | 234 | 236 | 238 | 240 | 242 | 244 |
| H4H10238P | 246 | 248 | 250 | 252 | 254 | 256 | 258 | 260 |
| H4H10250P | 262 | 264 | 266 | 268 | 270 | 272 | 274 | 276 |
| H4H10256P | 278 | 280 | 282 | 284 | 286 | 288 | 290 | 292 |
| H4H10270P | 294 | 296 | 298 | 300 | 302 | 304 | 306 | 308 |

Additional GCG antibodies or antibody fragments contemplated as useful herein include those disclosed in U.S. Pat. Nos. 4,206,199; 4,221,777; 4,423,034; 4,272,433; 4,407,965; 5,712,105; and PCT publications WO2007/124463 and WO2013/081993.

Antibody fragments include any fragment having the required target specificity, e.g. antibody fragments either produced by the modification of whole antibodies (e.g. enzymatic digestion), or those synthesized de novo using recombinant DNA methodologies (scFv, single domain antibodies, DVD (dual variable domain immunoglobulins), or dAbs (single variable domain antibodies)) or those identified using human phage or yeast display libraries (see, for example, McCafferty et al. (1990) Nature 348:552-554). Alternatively, antibodies can be isolated from mice producing human, human-mouse, human-rat, and human-rabbit chimeric antibodies using standard immunization and antibody isolation methods, including but not limited to making hybridomas, or using B cell screening technologies, such as SLAM Immunoglobulin binding domains also include, but are not limited to, the variable regions of the heavy ($V_H$) or the light ($V_L$) chains of immunoglobulins. Or by immunizing people and isolating antigen positive B cells and cloning the cDNAs encoding the heavy and light chain and coexpressing them in a cell, such as CHO.

The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. IgG1, IgG2, IgG3, IgG4). Typically, the antigen-binding region of an antibody will be the most critical in determining specificity and affinity of binding.

An exemplary immunoglobulin (antibody) structural unit comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology.

Methods for preparing antibodies useful according to the methods herein are known to the art. See, for example, Kohler & Milstein (1975) Nature 256:495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Monoclonal antibodies can be humanized using standard cloning of the CDR regions into a human scaffold. Gene libraries encoding human heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the methods disclosed herein. Also, transgenic mice, or other organisms such as other mammals, may be used to express human, human-mouse chimeric, human-rat chimeric, human-rabbit chimeric, or humanized antibodies. Alternatively, phage display or yeast display technology can be used to identify human antibodies and heteromeric Fab fragments that specifically bind to selected antigens.

Immunoconjugates

The disclosure encompasses treatment of severe insulin resistance with a human anti-GCGR monoclonal antibody conjugated to a therapeutic moiety ("immunoconjugate"), such as an agent that is capable of reducing blood glucose levels or addressing another symptom of severe insulin resistance. The type of therapeutic moiety that may be conjugated to the anti-GCGR antibody will take into account the condition to be treated and the desired therapeutic effect to be achieved. For example, in an effort to lower blood glucose, and/or to maintain normal blood glucose levels, an agent such as biguanide (e.g. metformin), a sulfonylurea (e.g. glyburide, glipizide), a PPAR gamma agonist (e.g. pioglitazone, rosiglitazone); an alpha glucosidase inhibitor (e.g. acarbose, voglibose), an inhibitor of advanced glycation end-product formation (e g aminoguanidine), or a second GCGR inhibitor or GCG inhibitor may be conjugated to the GCGR antibody. Alternatively, if the desired therapeutic effect is to treat ketonemia or any other symptoms or conditions associated with severe insulin resistance, it may be advantageous to conjugate an appropriate agent to the anti-GCGR antibody. Examples of suitable agents for forming immunoconjugates are known in the art, see for example, WO 05/103081.

Multi-Specific Antibodies

The antibodies useful according to the methods provided herein may be mono-specific, bi-specific, or multi-specific. Multi-specific antibodies may be specific for different epitopes of one target polypeptide or may contain antigen-binding domains specific for more than one target polypeptide. See, e.g., Tutt et al., (1991) J. Immunol. 147:60-69; Kufer et al., (2004) Trends Biotechnol. 22:238-244. The anti-GCGR antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, bi-specific antibodies are contemplated where one arm of an immunoglobulin is specific for human GCGR or a fragment thereof, and the other arm of the immunoglobulin is specific for a second therapeutic target or is conjugated to a therapeutic moiety. In certain embodiments, one arm of an immunoglobulin is specific for an epitope on the N-terminal domain of hGCGR or a fragment thereof, and the other arm of the immunoglobulin is specific for an epitope on one of the EC loops of hGCGR, or a fragment thereof. In certain embodiments, one arm of an immunoglobulin is specific for one EC loop, or a fragment thereof, and the second arm is specific for a second EC loop, or a fragment thereof. In certain embodiments, one arm of an immunoglobulin is specific for one epitope on one EC loop of hGCGR and the other arm is specific for a second epitope on the same EC loop of hGCGR.

An exemplary bi-specific antibody format that can be used according to the methods described herein involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Antibody Screening and Selection

Screening and selection of preferred antibodies, useful according to the methods provided herein, can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of antibody-drug conjugates. Secondary screening may be conducted with any suitable method known to the art. One preferred method, termed "Biosensor Modification-Assisted Profiling" ("BiaMAP") is described in U.S. Publication 2004/0101920, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody: antigen interactions. Antibodies capable of blocking either a ligand or a receptor may be identified by a cell based assay, such as a luciferase assay utilizing a luciferase gene under the control of an NFκB driven promoter or cAMP response driven promoter. Stimulation of the GCGR by glucagon leads to a signal through NFκB/cAMP/CREB thus increasing luciferase levels in the cell. Blocking antibodies are identified as those antibodies that blocked glucagon induction of luciferase activity.

Treatment Population

The therapeutic methods provided herein are useful for treating individuals with severe insulin resistance or a condition or disease associated with severe insulin resistance. Exemplary conditions or diseases include Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, and a condition or disease associated with the presence of a gene variant reported to cause severe insulin resistance. In some embodiments, insulin degrading protease activity is detected in the patient sera. In some embodiments, neutralizing anti-insulin antibodies are detected in the patient sera. In some patients, severe insulin resistance arises in the context of autoimmune destruction of adipocytes leading to lipodystrophy.

Therapeutic Administration and Formulations

Useful according to the methods provided herein are therapeutic compositions comprising a glucagon/GCGR antagonist, such as, for example, an anti-GCGR antibody. The administration of therapeutic compositions in accordance with the methods described herein will be administered via a suitable route including, but not limited to, intravenously, subcutaneously, intramuscularly, intrathecally, intracerebrally, intraventricularly, intranasally, or orally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody is used for lowering blood glucose levels and/or decreasing ketonemia (as measured by, for example, beta-hydroxybutyrate levels) associated with severe insulin resistance in various conditions and diseases, such as Type A insulin resistance syndrome, RMS, or DS, in a patient, it is advantageous to intravenously administer the antibody normally at a dose of about 0.01 to about 30 mg/kg body weight, more preferably about 0.02 to about 7, about 0.03 to about 5, or about 0.05 to about 3 mg/kg body weight. Depending on the severity of the condition and response to treatment, the frequency and the duration of the treatment can be adjusted. In certain embodiments, the antibody or antigen-binding fragment thereof can be administered as an initial dose of at least about 0.1 mg to about 800 mg, about 1 to about 500 mg, about 5 to about 300 mg, or about 10 to about 200 mg, to about 100 mg, or to about 50 mg.

In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition comprising the antibody, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, depot formulations, aerosol, intradermal, transdermal, intramuscular, intraperitoneal, intravenous, subcutaneous, intranasal, epidural, intrathecal, intraventricular, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition useful herein can be delivered subcutaneously or intravenously with a standard needle and syringe. In addition, with respect to subcutaneous delivery, a pen delivery device readily has applications in delivering a pharmaceutical composition useful in the methods described herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition useful according to the methods described herein. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Inn.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition useful according to the methods described herein include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 750 mg per dosage form in a unit dose; especially in the form of injection, it is preferred that the aforesaid antibody is contained in about 5 to about 100 mg and in about 10 to about 250 mg for the other dosage forms.

Combination Therapies

In numerous embodiments, the GCG inhibitors or GCGR antagonists useful herein may be administered in combination with one or more additional compounds or therapies. Combination therapy may be simultaneous or sequential.

In some embodiments, the GCG inhibitor or GCGR antagonist is administered with at least one additional therapeutic agent selected from the following: insulin, a biguanide, hIGF1, leptin, pioglitazone, vildagliptin, acarbose, alpha-glycosidase inhibitors, L-arginine, dipeptidyl-peptidase-4 inhibitors, insulin secretagogues, amylin receptor agonists, insulin sensitizers, SGLT2 inhibitors, SGLT1 inhibitors, GLP-1 analogues, GLP-1 receptor activators, a second GCG inhibitor, and a second GCGR antagonist. In some embodiments, the GCG inhibitor or GCGR antagonist is administered with at least one additional therapeutic agent selected from the following: vanadate or vanadium salts, phenytoin, benzafibrate. In some embodiments, the GCG inhibitor or GCGR antagonist is administered with a dietary supplement such as ω-3 fatty acid rich fish oil.

In some embodiments, the insulin sensitizer is a thiazolidinedione, such as troglitazone. In some embodiments, the insulin sensitizer is rosiglitazone.

In some embodiments, the insulin secretagogue is a sulfonylurea, ATP-sensitive K channel antagonists, or a meglitinide.

The additional therapeutically active component(s) may be administered prior to, concurrent with, or after the administration of the GCG inhibitor or the GCGR antagonist. For purposes of the present disclosure, such administration regimens are considered the administration of a GCG inhibitor or a GCGR antagonist "in combination with" a second therapeutically active component.

Administration Regimens

According to certain embodiments described herein, multiple doses of the glucagon/GCGR antagonist may be administered to a subject over a defined time course. The methods comprise sequentially administering to a subject multiple doses of a glucagon/GCGR antagonist. As used herein, "sequentially administering" means that each dose of the antagonist is administered to the subject at a different point in time, e.g., on different days separated by a predetermined interval (e.g., hours, days, weeks or months). The methods described herein comprise sequentially administering to the patient a single initial dose of the glucagon/GCGR antagonist, followed by one or more secondary doses of the glucagon/GCGR antagonist, and optionally followed by one or more tertiary doses of the glucagon/GCGR antagonist.

The terms "initial dose," "secondary doses," and "tertiary doses," refer to the temporal sequence of administration of an glucagon/GCGR antagonist useful herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the glucagon/GCGR antagonist, but generally may differ from one another in terms of frequency of administration. In certain embodiments, however, the amount of the glucagon/GCGR antagonists contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Pharmaceutical Compositions

The methods disclosed herein contemplate the use of pharmaceutical compositions comprising at least a therapeutically effective amount of an active agent useful in treating severe insulin resistance, such as a glucagon/GCGR antagonist, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In one embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents useful according to the methods described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent which will be effective in the treatment of severe insulin resistance can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20 micrograms to 2 grams of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

Also provided herein is an article of manufacturing comprising packaging material and a pharmaceutical agent contained within the packaging material, wherein the pharmaceutical agent comprises at least one GCG/GCGR antagonist useful according to the methods disclosed herein, and wherein the packaging material comprises a label or package insert which indicates that the GCG/GCGR antagonist can be used for treating a condition or disease characterized by severe insulin resistance.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided such that those of ordinary skill in the art have a complete disclosure and description of how to implement the methods disclosed herein. Efforts have been made to ensure accuracy with respect to numbers used (e.g., amounts, temperature, etc.) but some experimental errors and deviations should be accounted for. Unless indicated otherwise, parts are by weight, molecular weight is average molecular weight, temperature is in degrees Centigrade, and pressure is at or near atmospheric.

Example 1: Evaluation of a GCGR Antagonist in Preventing Hyperglycemia in a Mouse Model of Extreme Insulin Resistance Administration of S961, an insulin receptor antagonist, by osmotic minipumps in mice causes severe insulin resistance and hyperglycemia (Gusarova V et al., (2014) Cell, 159: 691-696; Yi P et al., (2013) Cell, 153:747-758; Schaffer L., (2008) Biochem. Biophys. Res. Commun., 376:380-383). This model of severe insulin resistance was used to determine the effect of an anti-GCGR antibody in preventing hyperglycemia, as well as the effects on blood glucose levels and plasma beta-hydroxybutyrate levels (as a measure of ketonemia), resulting from severe insulin resistance.

Materials:
  hIgG4 isotype control
  H4H1327P, anti-hGCGR hIgG4
  S961, insulin receptor antagonist (custom synthesized by Celtek Peptides using published sequence (Schaffer L., (2008) Biochem. Biophys. Res. Commun., 376:380-383))

Animals and Injections:
  Twenty-nine mice were divided into four groups of six to eight mice. The first group was injected subcutaneously with 10 mg/kg of hIgG4 isotype control on Day 0, 6, and 14 and infused subcutaneously with PBS by osmotic minipumps (Alzet 2002) from Day 7. The second group was injected subcutaneously with 10 mg/kg of H4H1327P on Day 0, 6, and 14 and infused subcutaneously with PBS by osmotic minipumps (Alzet 2002) from Day 7. The third group was injected subcutaneously with 10 mg/kg of hIgG4 isotype control on Day 0, 6, and 14 and infused subcutaneously with 5961 at 20 nmol/week by osmotic minipumps (Alzet 2002) from Day 7. The fourth group was injected subcutaneously with 10 mg/kg of H4H1327P on Day 0, 6, and 14 and infused subcutaneously with 5961 at 20 nmol/week by osmotic minipumps (Alzet 2002) from Day 7. Mice were bled on Days 0, 3, 6, 10, 14, 17, and 21 for blood glucose measurements. Mean±SEM of blood glucose levels at each time point was calculated for each group and shown in Table 3. Plasma was collected at baseline and Days 6, 14, and 21 to determine insulin and beta-hydroxybutyrate levels. Mean±SEM of plasma beta-hydroxybutyrate and insulin levels at each time point was calculated for each group and shown in Tables 4 and 5.

TABLE 3

Blood glucose levels

| | Time (days) | Isotype control + PBS | H4H1327P + PBS | Isotype control + S961 | H4H1327P + S961 |
|---|---|---|---|---|---|
| Blood Glucose (mg/dL) | 0 | 196 ± 6 | 191 ± 4 | 186 ± 5 | 196 ± 3 |
| | 3 | 195 ± 7 | 119 ± 3 | 191 ± 6 | 124 ± 6 |
| | 6 | 194 ± 9 | 126 ± 4 | 192 ± 5 | 129 ± 12 |
| | 10 | 186 ± 4 | 135 ± 2 | 437 ± 40 | 185 ± 7 |
| | 14 | 197 ± 5 | 128 ± 4 | 508 ± 53 | 272 ± 53 |
| | 17 | 211 ± 6 | 144 ± 3 | 467 ± 41 | 219 ± 22 |
| | 21 | 206 ± 5 | 141 ± 5 | 499 ± 18 | 209 ± 6 |

TABLE 4

Plasma beta-hydroxybutyrate levels

| | Time (days) | Isotype control + PBS | H4H1327P + PBS | Isotype control + S961 | H4H1327P + S961 |
|---|---|---|---|---|---|
| Beta-hydroxybutyrate (mg/dL) | 0 | 0.20 ± 0.02 | 0.20 ± 0.02 | 0.21 ± 0.02 | 0.24 ± 0.02 |
| | 6 | 0.26 ± 0.01 | 0.24 ± 0.01 | 0.26 ± 0.01 | 0.27 ± 0.01 |
| | 14 | 0.22 ± 0.02 | 0.23 ± 0.02 | 0.34 ± 0.04 | 0.26 ± 0.03 |
| | 21 | 0.23 ± 0.01 | 0.23 ± 0.02 | 0.34 ± 0.04 | 0.25 ± 0.03 |

TABLE 5

Plasma insulin levels

| | Time (days) | Isotype control + PBS | H4H1327P + PBS | Isotype control + S961 | H4H1327P + S961 |
|---|---|---|---|---|---|
| Insulin (ng/mL) | 0 | 0.80 ± 0.14 | 1.90 ± 0.69 | 1.15 ± 0.68 | 1.62 ± 0.67 |
| | 6 | 0.24 ± 0.04 | 0.24 ± 0.06 | 0.21 ± 0.10 | 0.24 ± 0.04 |
| | 14 | 0.37 ± 0.09 | 0.36 ± 0.05 | 22.83 ± 4.32 | 18.51 ± 2.30 |
| | 21 | 0.40 ± 0.13 | 0.46 ± 0.15 | 23.97 ± 4.36 | 25.11 ± 5.15 |

Results:

Statistical analysis was performed with Prism software (version 6). To assess the significance to the control group (Group 1), two-way ANOVA with Bonferroni multiple comparison test was used. a: $p<0.05$, b: $p<0.01$, c: $p<0.001$, d: $p<0.0001$.

H4H1327P-treated and PBS-infused animals (Group 2) showed reductions in blood glucose compared to isotype control-administered and PBS-infused animals (Group 1) post H4H1327P administration (between days 3 and 21), confirming glucose lowering efficacy of H4H1327P. Isotype control-administered and S961-infused animals (Group 3) showed increases in blood glucose compared to isotype control-administered and PBS-infused animals (Group 1) post infusion of 5961 (between days 10 and 21), confirming hyperglycemic effect of 5961. In H4H1327P-treated and S961-infused animals (Group 4), blood glucose levels were comparable to those of Group 1 mice between 10 and 21 days post S961 infusion. See FIG. 1A.

Figure 1B:
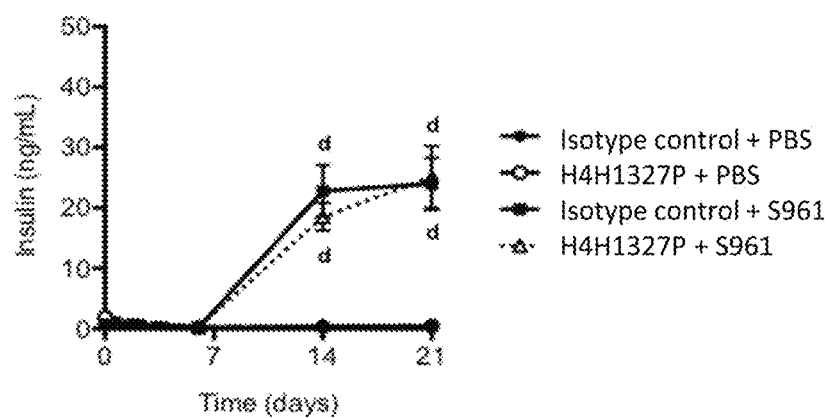

Plasma insulin levels were elevated in isotype control-administered and S961-infused animals (Group 3) compared to isotype control-administered and PBS-infused animals (Group 1) on Days 14 and 21, confirming the action of 5961 to inhibit insulin receptor during the duration of the study. The insulin levels were equally increased in H4H1327P-treated and S961-infused animals (Group 4) in comparison to isotype control-administered and S961-infused animals (Group 3). See FIG. 1B.

Figure 1C:
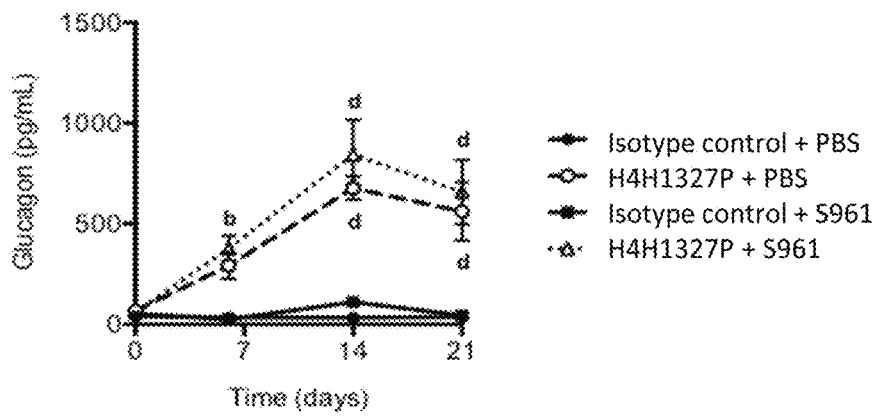

Consistent with previous studies (Okamoto et al., (2015) Endocrinology, 156(8): 2781-2794), H4H1327P demonstrated increased plasma glucagon levels, an effect that was independent of 5961 administration (See FIG. 1C).

Figure 1D:
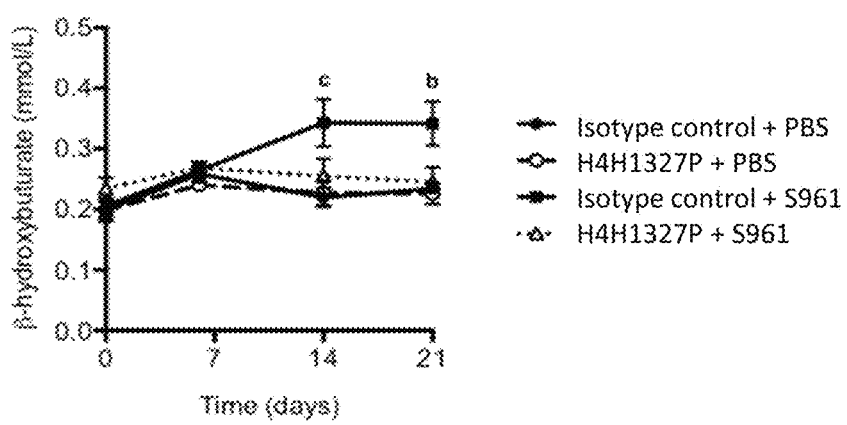
Figure 1E:
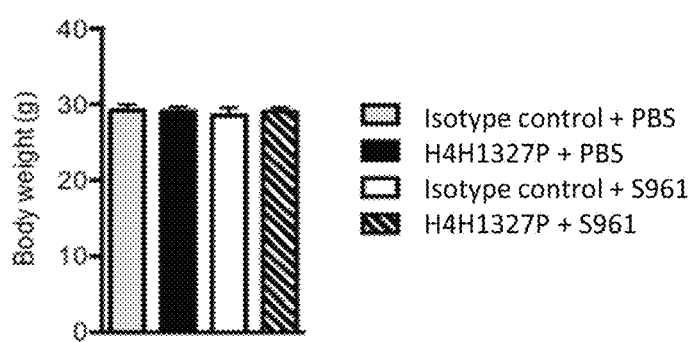

The levels of plasma beta-hydroxybutyrate were elevated in isotype control-administered and S961-infused animals (Group 3) compared to isotype control-administered and PBS-infused animals (Group 1) on Day 14 and 21, whereas they were not changed in H4H1327P-treated and S961-infused animals (Group 4). See FIG. 1D. In addition, no differences in body weight were observed between the treatment groups (See FIG. 1E).

These data indicate that H4H1327P prevents insulin receptor antagonist-induced hyperglycemia and ketonemia and lowers blood glucose even in the presence of severe hyperinsulinemia.

Example 2: Evaluation of a GCGR Antagonist in Reversing Hyperglycemia in a Mouse Model of Extreme Insulin Resistance The effect of an anti-GCGR antibody in reversing established hyperglycemia induced by severe insulin resistance was determined using the same animal model and the same materials mentioned in Example 1, except that the insulin receptor antagonist was administered 4 days prior to injection of the anti-GCGR antibody. The effects on blood glucose and plasma beta-hydroxybutyrate levels were also determined.

Animals and Injections:

Thirty-two mice were divided into four groups of eight mice. The first group was infused subcutaneously with PBS by osmotic minipumps (Alzet 2002) from Day 0 and injected subcutaneously with 10 mg/kg of hIgG4 isotype control on Day 4, 11 and 18. The second group was infused subcutaneously with PBS from Day 0 and injected subcutaneously with 10 mg/kg of H4H1327P on Day 4, 11 and 18. The third group was infused subcutaneously with S961 at 20 nmol/week from Day 0 and injected subcutaneously with 10 mg/kg of hIgG4 isotype control on Day 4, 11 and 18. The fourth group was infused subcutaneously with S961 at 20 nmol/week from Day 0 and injected subcutaneously with 10 mg/kg of H4H1327P on Day 4, 11 and 18. Mice were bled on Days 0, 4, 7, 11, 14, 18 and 21 for blood glucose measurements. Mean±SEM of blood glucose levels at each time point was calculated for each group and shown in Table 6. Plasma was collected at baseline and Days 4, 11, and 21 to determine insulin and beta-hydroxybutyrate levels. Mean±SEM of plasma beta-hydroxybutyrate and insulin levels at each time point was calculated for each group and shown in Tables 7 and 8.

TABLE 6

Blood glucose levels (mg/dL)

| Time (days) | PBS + isotype control | PBS + H4H1327P | S961 + isotype control | S961 + H4H1327P |
|---|---|---|---|---|
| 0 | 186 ± 4 | 189 ± 4 | 192 ± 4 | 183 ± 4 |
| 4 | 196 ± 3 | 197 ± 3 | 491 ± 29 | 490 ± 21 |
| 7 | 216 ± 5 | 142 ± 6 | 523 ± 34 | 203 ± 6 |
| 11 | 206 ± 6 | 137 ± 4 | 533 ± 14 | 201 ± 6 |
| 14 | 210 ± 7 | 145 ± 5 | 595 ± 6 | 211 ± 9 |
| 18 | 202 ± 7 | 140 ± 4 | 550 ± 16 | 203 ± 5 |
| 21 | 168 ± 6 | 123 ± 4 | 526 ± 12 | 172 ± 5 |

TABLE 7

Plasma beta-hydroxybutyrate levels (mmol/L)

| Time (days) | PBS + isotype control | PBS + H4H1327P | S961 + isotype control | S961 + H4H1327P |
|---|---|---|---|---|
| 0 | 0.20 ± 0.01 | 0.22 ± 0.01 | 0.21 ± 0.02 | 0.18 ± 0.02 |
| 4 | 0.27 ± 0.01 | 0.25 ± 0.02 | 0.41 ± 0.02 | 0.37 ± 0.04 |
| 11 | 0.26 ± 0.02 | 0.24 ± 0.01 | 0.39 ± 0.03 | 0.26 ± 0.02 |
| 21 | 0.26 ± 0.01 | 0.25 ± 0.01 | 0.45 ± 0.06 | 0.26 ± 0.02 |

TABLE 8

Plasma insulin levels (ng/mL)

| Time (days) | PBS + isotype control | PBS + H4H1327P | S961 + isotype control | S961 + H4H1327P |
|---|---|---|---|---|
| 0 | 1.05 ± 0.31 | 0.77 ± 0.25 | 0.52 ± 0.08 | 0.42 ± 0.09 |
| 4 | 0.62 ± 0.32 | 0.50 ± 0.11 | 19.23 ± 3.18 | 21.68 ± 2.02 |
| 11 | 0.39 ± 0.09 | 0.35 ± 0.05 | 25.97 ± 3.48 | 64.25 ± 18.17 |
| 21 | 1.67 ± 0.47 | 0.37 ± 0.04 | 51.43 ± 15.03 | 64.78 ± 14.91 |

Results:

Statistical analysis was performed with Prism software (version 6). To assess the significance to the control group (Group1), two-way ANOVA with Bonferroni multiple comparison test was used. a: $p<0.05$, b: $p<0.01$, c: $p<0.001$, d: $p<0.0001$.

Figure 2A:
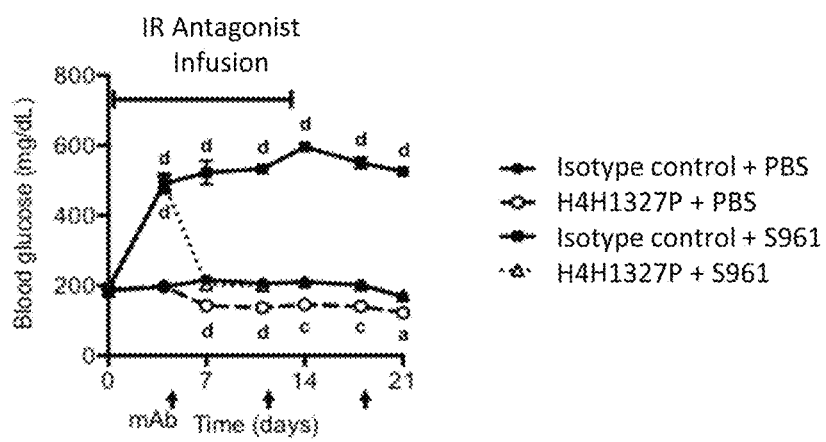
FIGS. 2A-2F show blood glucose levels, insulin levels, glucagon levels, B-hydroxybutyrate levels, and amino acid levels, as well as body weights, in a mouse model of severe insulin resistance. The insulin receptor antagonist (S961) treatment preceded the antibody treatment, H4H1327P, causing increased blood glucose levels, and the ability of the antibody to decrease blood glucose levels was demonstrated within days of initiating antibody treatment (open triangles). See FIG. 2A.

S961-infused and isotype control-administered animals (Group 3) showed increases in blood glucose compared to PBS-infused and isotype control-administered animals (Group 1) post 5961 infusion (between days 4 and 21), confirming hyperglycemic effect of 5961. S961-infused and H4H1327P-treated animals (Group 4) showed blood glucose levels that were nearly identical to those of PBS-infused and isotype control-administered and animals (Group 1) post H4H1327P administration. PBS-infused and H4H1327P-treated animals (Group 2) maintained reduced levels of blood glucose compared to isotype control-administered and PBS-infused animals (Group 1) post H4H1327P administration (between days 4 and 21), confirming glucose lowering efficacy of H4H1327P. See FIG. 2A.

Figure 2B:
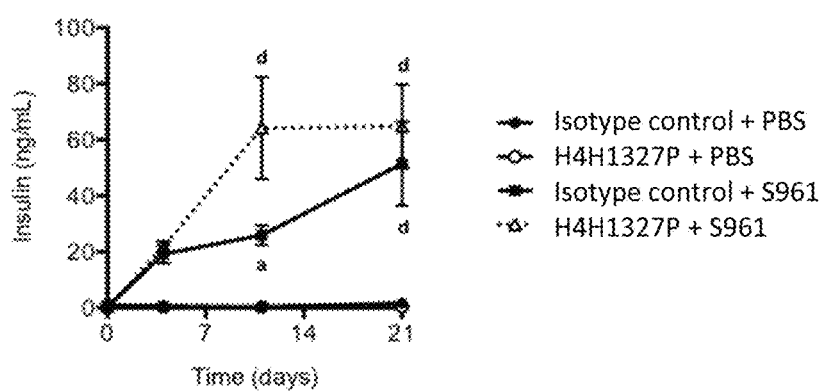
Figure 2C:
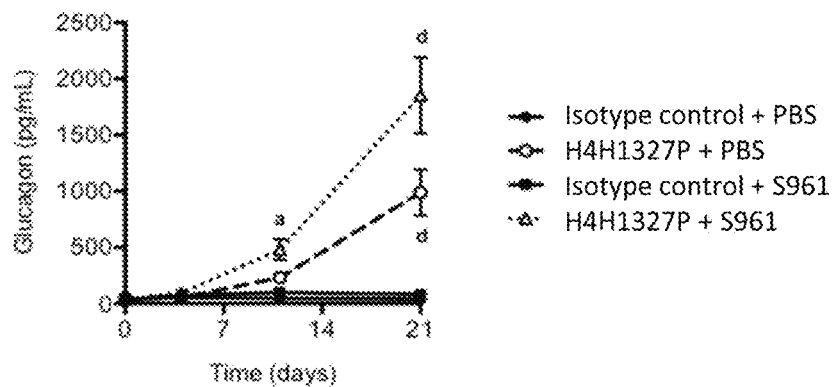

Plasma insulin levels were elevated in S961-infused and isotype control-administered animals (Group 3) compared to PBS-infused and isotype control-administered animals (Group 1) on Days 4, 11 and 21, confirming the action of 5961 to inhibit insulin receptor during the duration of the study. See FIG. 2B. The hyperinsulinemia (Table 8 and FIG. 2B) and hyperglucagonemia (see FIG. 2C) was more pronounced in mice that received both receptor antagonists.

Figure 2D:
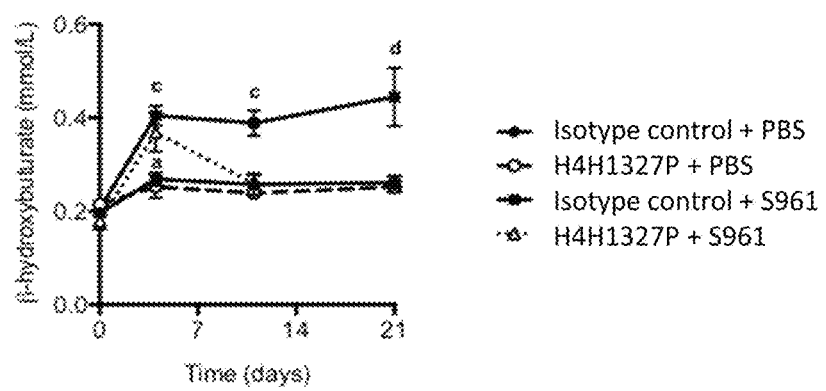

The levels of plasma beta-hydroxybutyrate were elevated in S961-infused and isotype control-administered animals (Group 3) compared to PBS-infused and isotype control-administered animals (Group 1) on Days 11 and 21, whereas they were not changed in S961-infused and H4H1327P-treated animals (Group 4) at these same time points relative to Group 1 animals. See FIG. 2D.

Figure 2E:
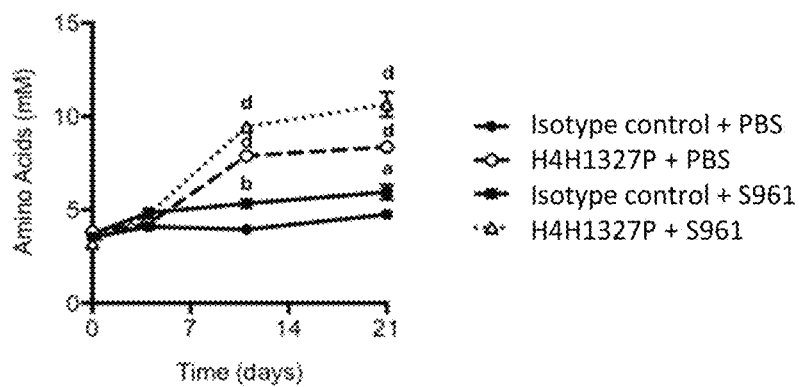
Figure 2F:
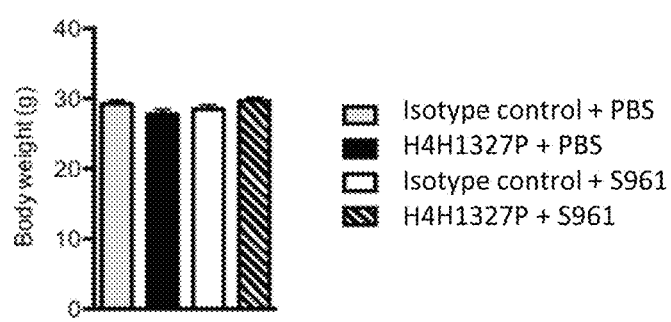

Consistent with previous findings (Okamoto et al., 2015), H4H1327P increased circulating amino acid levels, as did 5961 but to a lesser extent than did the antibody (see FIG. 2E). Inhibition of both insulin and glucagon receptors caused an additive increase in plasma amino acid levels (see FIG. 2E). No changes in body weight were observed (see FIG. 2F).

These data indicate that H4H1327P reverses insulin receptor antagonist-induced hyperglycemia and ketonemia and lowers blood glucose even in the presence of severe hyperinsulinemia.

Example 3: Evaluation of a GCGR Antagonist in Reversing Insulin Receptor Antagonist-Induced Liver Pepck Expression Liver samples obtained from mice treated according to each of the four groups from Example 1 were lysed with ice-cold RIPA buffer (50 mM Tris, 150 mM NaCl, 1 mM of EDTA, 50 mM NaF, 10 mM β-glycerophosphate, 5 mM sodium pyrophosphate dibasic and 1% NP-40) in the presence of protease and phosphatase inhibitor cocktails (Thermo-Fisher), 1 mM DTT and 2 mM $Na_3VO_4$. Total sample lysates were mixed with 6× SDS loading buffer (Alfa-Aesar) and boiled for 5 min. Protein samples (10-100 μg) were loaded and separated on 4-20% gradient SDS-PAGE gels (Bio-Rad) and transferred to polyvinylidene difluoride membranes. The membranes were blocked for 1 h with 5% bovine serum albumin in 1× TBS supplemented with 0.1% Tween20 (Bio-Rad) and incubated with antibody against phosphoenolpyruvate carboxykinase (PEPCK) (1:250; Abcam). Bound antibodies were detected using horseradish peroxidase-conjugated anti-rabbit or anti-mouse secondary antibodies (1:10,000; Jackson ImmunoResearch) and enhanced chemiluminescence reagent (Thermo-Fisher). Band intensities were quantified in Image J software.

Figure 3A:
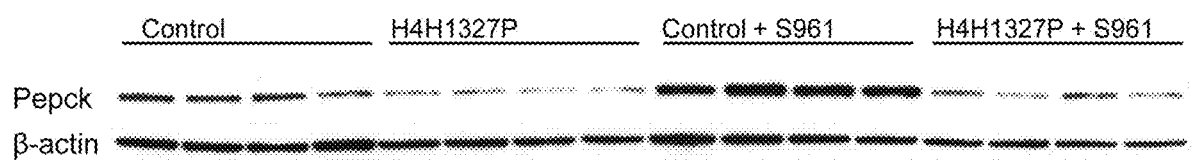
FIGS. 3A and 3B provide the results of Western blot analysis on mice liver samples obtained from mice treated with one or both of 5961 and H4H1327P. Treatment with H4H1327P reduced phosphoenolpyruvate carboxykinase (Pepck) in mice livers by 70% relative to the isotype treated control group, and treatment with 5961 caused a 2.3 fold increase in Pepck levels. Treatment with H4H1327P reversed the increased levels caused by S961 to 30% below baseline. See FIGS. 3A and 3B.
Figure 3B:
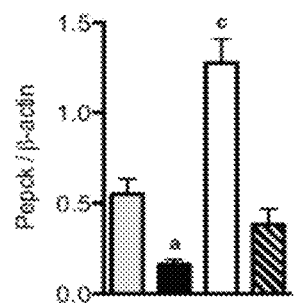

Western blot analysis revealed that levels of the rate limiting gluconeogenic enzyme phosphoenolpyruvate carboxykinase (Pepck) were reduced by 70% in livers of mice treated with H4H1327P (see FIGS. 3A and B). On the contrary, Pepck levels increased 2.3-fold in livers of mice infused with 5961, an effect that was reversed to 30% below baseline by H4H1327P. Thus, the relative levels of glucagon and insulin signaling regulate Pepck expression, as demonstrated previously (Lynedjian et al., (1995); Rucktaschel et al., (2000); Chakravarty et al., (2005)). These data show that GCGR blockade with H4H1327P prevents severe insulin resistance-induced hyperglycemia in mice by suppressing hepatic glucose output.

Example 4: Evaluation of GCGR and Insulin Receptor Antagonism in α- and β-Cell Masses The pancreas obtained from mice treated according to each of the four groups from Example 2 were fixed in 10% neutral buffered formalin solution for 48 h, embedded in paraffin, and sectioned onto slides. Pancreatic tissue and cells were permeabilized and hybridized with combinations of mRNA probes for mouse Gcg and Ins2 according to the manufacturer's instructions (Advanced Cell Diagnostics). A chromagenic kit was used to amplify mRNA signal (Advanced Cell Diagnostics). Areas of glucagon and insulin positive cells were measured using Halo digital imaging analysis software (Indica Labs). The percent of glucagon and insulin positive areas in proportion to the whole pancreas area were calculated. α- and β-cell mass was calculated by multiplying the α- and β-cell area for each animal against their corresponding pancreas weight. Islet number was measured by counting the number of insulin positive islets on a section with the use of Halo digital imaging analysis software and normalized by the entire pancreas area of the section.

Figure 4A:
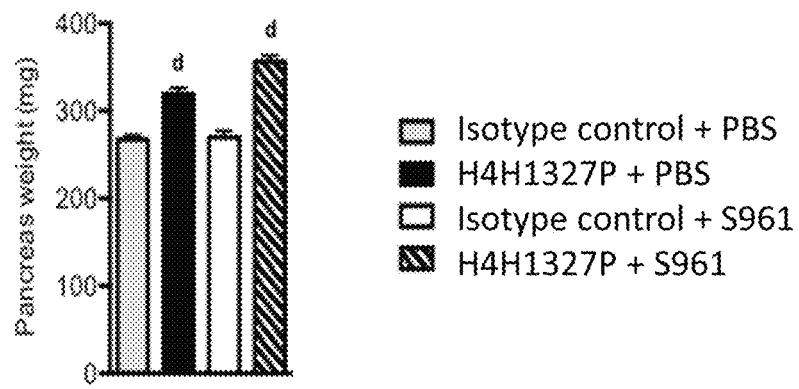
FIGS. 4A-4D show the effects of the four treatments on pancreatic tissue: pancreas weight, FIG. 4A; pancreas α-cell mass, FIG. 4B; pancreas β-cell mass, FIG. 4C; and islet numbers relative to total pancreas area, FIG. 4D. β-cell mass doubled in the presence of S961 and H4H1327P when compared to 5961 alone and increased 5.8-fold over control mice. See FIG. 4C.
Figure 4B:
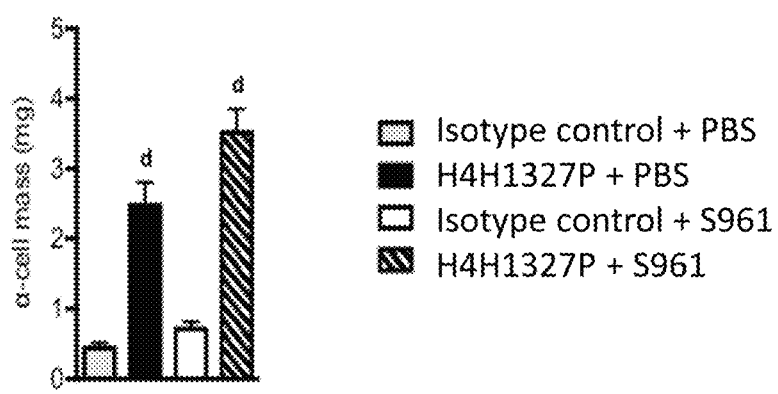
Figure 4C:
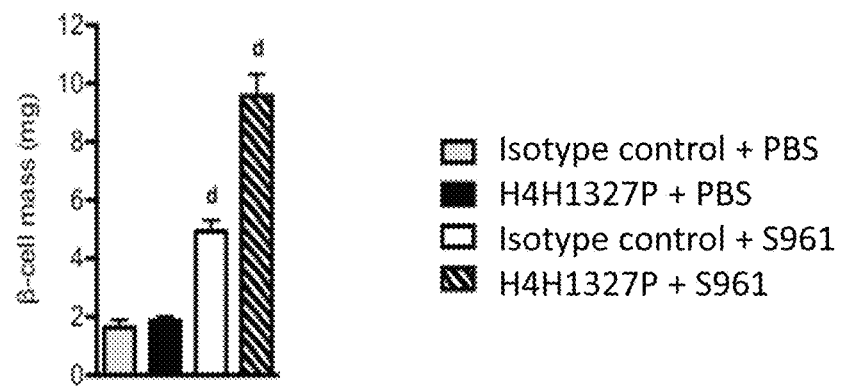
Figure 4D:
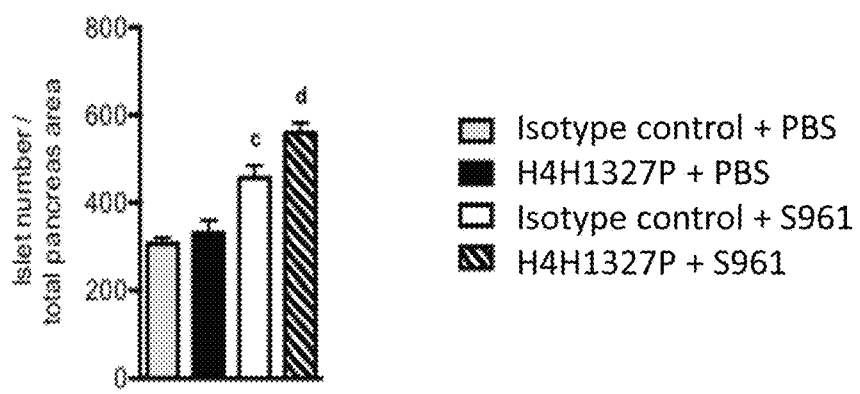

H4H1327P increased pancreas weight by 19%, an effect that was larger (33%) in the presence of both H4H1327P and 5961 (see FIG. 4A). RNA in situ hybridization (RNA ISH) using probes to Gcg and Ins2 was used for morphometric analysis of pancreatic sections. H4H1327P increased α-cell mass 5.7-fold (see FIG. 4B), and 5961 administration increased β-cell mass 3-fold (see FIG. 4C). H4H1327P alone did not affect β-cell mass, but unexpectedly, β-cell mass doubled in the simultaneous presence of 5961 and H4H1327P when compared to 5961 alone and increased 5.8-fold over control mice (see FIG. 4C). It is important to note that the further expansion of the β-cell mass took place in settings of normal blood glucose levels (Table 3). α-cell mass was slightly increased by 5961 treatment (1.6-fold) and in the simultaneous presence of H4H1327P (1.4-fold over H4H1327P alone) (see FIG. 4B). S961 increased islet number per total pancreas area by 49%, whereas the combined treatment with 5961 and H4H1327P increased islet number per area by 82% (see FIG. 4D). In summary, compensatory increases in α- and β-cell masses were produced when glucagon and insulin signaling were inhibited. The novel finding is that β-cell mass doubled in insulin resistant mice when glucagon signaling was blocked and that this effect took place at normal blood glucose levels.

What is claimed is:

1. A method for lowering blood glucose levels and/or levels of ketone bodies in a patient with severe insulin resistance comprising administering, to the patient, a therapeutically effective amount of a composition comprising an inhibitor antibody or antigen-binding fragment thereof that binds specifically to glucagon receptor comprising
   (a) a heavy chain variable region comprising three heavy chain complementarity determining regions (HCDR1, HCDR2 and HCDR3) that are contained within a heavy chain variable region comprising the amino acid sequence set forth in SEQ ID NO: 86; and
   (b) a light chain variable region comprising three light chain complementarity determining regions (LCDR1, LCDR2 and LCDR3) that are contained within a light chain variable region comprising the amino acid sequence set forth in SEQ ID NO: 88.

2. The method of claim 1, wherein the
   HCDR1 comprises the amino acid sequence set forth in SEQ ID NO: 72;
   HCDR2 comprises the amino acid sequence set forth in SEQ ID NO: 74;
   HCDR3 comprises the amino acid sequence set forth in SEQ ID NO: 76;
   LCDR1 comprises the amino acid sequence set forth in SEQ ID NO: 80;
   LCDR2 comprises the amino acid sequence set forth in SEQ ID NO: 82; and
   LCDR3 comprises the amino acid sequence set forth in SEQ ID NO: 84.

3. The method of claim 2, wherein heavy chain variable region comprises the amino acid sequence set forth in SEQ ID NO: 86 and the light chain variable region comprises the amino acid sequence set forth in SEQ ID NO: 88.

4. The method of claim 3, wherein the antibody or antigen-binding fragment is an antibody which is a tetramer comprising two light chains and two heavy chains.

5. The method of claim 4, wherein the antibody light chain variable region is linked to a kappa light chain constant domain and the antibody heavy chain variable region is linked to an IgG heavy chain constant domain.

6. The method of claim 4, wherein the antibody light chain variable region is linked to a kappa light chain constant domain and the antibody heavy chain variable region is linked to an IgG4 heavy chain constant domain.

7. The method of claim 1, wherein the patient requires exogenous insulin at doses of more than 100 to 200 units per day.

8. The method of claim 1, wherein the patient has a fasting insulin level of above 50-70 μU/mL.

9. The method of claim 1, wherein the patient has peak (post-oral glucose tolerance testing) insulin levels above 350 μU/mL.

10. The method of claim 1, wherein the patient has insulin sensitivity index values below $2 \times 10^4$ μU/mL·min.

11. The method of claim 1, wherein the patient has a glucose disposal rate below 2 mg/kg·min.

* * * * *

SEQUENCE LISTING

<160> NUMBER OF SEQ ID NOS: 308

<210> SEQ ID NO 1
<211> LENGTH: 375
<212> TYPE: DNA
<213> ORGANISM: Artificial Sequence
<220> FEATURE:
<223> OTHER INFORMATION: Synthetic

<400> SEQUENCE: 1

```
caggtccagt tggtacagtc tggggctgac gtgaagaagc ctggggcctc agtgaaggtc      60
tcctgcaagg tttccggaca tatcctcact gatttatcca tgcactgggt gcgacagcct     120
cctggaaaag gacttgagtg gatggcaggt tttgatcctg aagaaggtaa aataatctac     180
gcacagaagt tccagggcag agtcaccatg accgaggaca catctacaga cacagcctac     240
atggagctga gcagcctgag atctggggac acggccgttt attactgtgc aacaagcgat     300
attttgactg ggtattatag agactactac ggtttggacg tctggggcca agggaccacg     360
ctcaccgtct cctca                                                      375
```

<210> SEQ ID NO 2
<211> LENGTH: 125
<212> TYPE: PRT
<213> ORGANISM: Artificial Sequence
<220> FEATURE:

<223> OTHER INFORMATION: Synthetic

<400> SEQUENCE: 2

Gln Val Gln Leu Val Gln Ser Gly Ala Asp Val Lys Lys Pro Gly Ala
1               5                   10                  15

Ser Val Lys Val Ser Cys Lys Val Ser Gly His Ile Leu Thr Asp Leu
            20                  25                  30

Ser Met His Trp Val Arg Gln Pro Pro Gly Lys Gly Leu Glu Trp Met
        35                  40                  45

Ala Gly Phe Asp Pro Glu Glu Gly Lys Ile Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Gly Asp Thr Ala Val Tyr Tyr Cys
                85                  90                  95

Ala Thr Ser Asp Ile Leu Thr Gly Tyr Tyr Arg Asp Tyr Tyr Gly Leu
            100                 105                 110

Asp Val Trp Gly Gln Gly Thr Thr Leu Thr Val Ser Ser
        115                 120                 125

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggacatatcc tcactgattt atcc                                        24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly His Ile Leu Thr Asp Leu Ser
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgatcctg aagaaggtaa aata                                        24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asp Pro Glu Glu Gly Lys Ile
1               5

<210> SEQ ID NO 7
<211> LENGTH: 54
<212> TYPE: DNA
<213> ORGANISM: Artificial Sequence
<220> FEATURE:
<223> OTHER INFORMATION: Synthetic

<400> SEQUENCE: 7
gcaacaagcg atattttgac tgggtattat agagactact acggtttgga cgtc    54

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Ala Thr Ser Asp Ile Leu Thr Gly Tyr Tyr Arg Asp Tyr Tyr Gly Leu
1               5                   10                  15

Asp Val

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9
gatattgtga tgactcagtc tccactcttc ctgcccgtca cccctggaga gccggcctcc     60
atctcctgca ggtctagtca gagcctcctg catagtaaag gatacaacta tttggattgg    120
tacctgcaga agccagggca gtctccacaa ctcctgatct atttgggttc taatcgggcc    180
tccggggtcc ctgacaggtt cagtggcagt ggatcaggca cagatttac actgaaaatc    240 agcagagtgg aggctgaaga tgttggggtt tattactgca tgcaaactct acaaactcct    300
cggacgttcg gccaagggac caaggtggaa atcaaa                              336

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
cagagcctcc tgcatagtaa aggatacaac tat                                33

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Gln Ser Leu Leu His Ser Lys Gly Tyr Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ttgggttct                                                            9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Leu Gly Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atgcaaactc tacaaactcc tcggacg                                       27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Met Gln Thr Leu Gln Thr Pro Arg Thr
1               5

<210> SEQ ID NO 17
<211> LENGTH: 375
<212> TYPE: DNA

<213> ORGANISM: Artificial Sequence
<220> FEATURE:
<223> OTHER INFORMATION: Synthetic

<400> SEQUENCE: 17

```
caggtccagt tggtacagtc tggggctgac gtgaagaagc ctggggcctc agtgaaggtc      60
tcctgcaagg tttccggaca tatcctcact gatttatcca tgcactgggt gcgacaggct     120
cctggaaaag gcttgagtg gatgggaggt tttgatcctg aagaaggtga ataatctac       180
gcacagaagt tccagggcag agtcaccatg accgaggaca catctacaga cacagcctac     240
atggagctga gcagcctgag atctggggac acggccgttt attactgtgc aacaagcgat     300
attttgactg gttattatag agactactac ggtttggacg tctggggcca agggaccacg     360
ctcaccgtct cctca                                                      375
```

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Gln Ser Gly Ala Asp Val Lys Lys Pro Gly Ala
1               5                   10                  15

Ser Val Lys Val Ser Cys Lys Val Ser Gly His Ile Leu Thr Asp Leu
                20                  25                  30

Ser Met His Trp Val Arg Gln Ala Pro Gly Lys Gly Leu Glu Trp Met
            35                  40                  45

Gly Gly Phe Asp Pro Glu Glu Gly Glu Ile Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Gly Asp Thr Ala Val Tyr Tyr Cys
                85                  90                  95

Ala Thr Ser Asp Ile Leu Thr Gly Tyr Tyr Arg Asp Tyr Tyr Gly Leu
            100                 105                 110

Asp Val Trp Gly Gln Gly Thr Thr Leu Thr Val Ser Ser
        115                 120                 125
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggacatatcc tcactgattt atcc                                             24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly His Ile Leu Thr Asp Leu Ser
1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
tttgatcctg aagaaggtga aata                                    24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Phe Asp Pro Glu Glu Gly Glu Ile
1               5

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
gcaacaagcg atattttgac tggttattat agagactact acggtttgga cgtc    54

<210> SEQ ID NO 24
<211> LENGTH: 18
<212> TYPE: PRT
<213> ORGANISM: Artificial Sequence
<220> FEATURE:
<223> OTHER INFORMATION: Synthetic

<400> SEQUENCE: 24

Ala Thr Ser Asp Ile Leu Thr Gly Tyr Tyr Arg Asp Tyr Tyr Gly Leu
1               5                   10                  15

Asp Val

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25
gatattgtga tgactcagtc tccactcttc ctgcccgtca cccctggaga gccggcctcc    60
atctcctgca ggtctagtca gagcctcctg catagtaaag gatacaacta tttggattgg   120
tacctgcaga agccagggca gtctccacaa ctcctgatct atttgggttc taatcgggcc   180
tccggggtcc ctgacaggtt cagtggcagt ggatcaggca cagatttac actgaaaatc   240 agcagagtgg aggctgaaga tgttggggtt tattactgca tgcaaactct acaaactcct   300
cggacgttcg gccaagggac caaggtgaa atcaaa                              336

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Arg Thr Phe Gly Gln Gly Thr Lys Val Glu Ile Lys
            100                 105                 110

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
cagagcctcc tgcatagtaa aggatacaac tat                          33

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Gln Ser Leu Leu His Ser Lys Gly Tyr Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ttgggttct                                                      9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Leu Gly Ser
1

<210> SEQ ID NO 31
<211> LENGTH: 27

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
atgcaaactc tacaaactcc tcggacg                                        27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Met Gln Thr Leu Gln Thr Pro Arg Thr
1               5

<210> SEQ ID NO 33
<211> LENGTH: 372
<212> TYPE: DNA
<213> ORGANISM: Artificial Sequence
<220> FEATURE:
<223> OTHER INFORMATION: Synthetic

<400> SEQUENCE: 33
gaggagcaac tggtggagtc tgggggagac ttggtacagc ctggagggtc cctaagactc      60
tcctgtgcag cctctggatt cactctcagt agttatgaaa tgaactgggt ccgccaggct     120
ccagggaagg ggctggagtg ggtttcatac attagtagag tggtagtct gatacactac      180 acagactctg tgaagggccg attcaccatc tccagagaca acgccaagaa ttcactgtat     240
ctgcaaatga acagcctgag agccgaggac acggctgttt attactgtgt gagagaccca    300
gcagctcgtt atcattatta ttatcacggt atggacgtct ggggccaagg gaccacggtc     360
accgtctcct ca                                                        372

<210> SEQ ID NO 34
<211> LENGTH: 124
<212> TYPE: PRT
<213> ORGANISM: Artificial Sequence
<220> FEATURE:
<223> OTHER INFORMATION: Synthetic

<400> SEQUENCE: 34

Glu Glu Gln Leu Val Glu Ser Gly Gly Asp Leu Val Gln Pro Gly Gly
1               5                   10                  15

Ser Leu Arg Leu Ser Cys Ala Ala Ser Gly Phe Thr Leu Ser Ser Tyr
            20                  25                  30

Glu Met Asn Trp Val Arg Gln Ala Pro Gly Lys Gly Leu Glu Trp Val
        35                  40                  45

Ser Tyr Ile Ser Arg Gly Gly Ser Leu Ile His Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Pro Ala Ala Arg Tyr His Tyr Tyr Tyr His Gly Met Asp
            100                 105                 110

Val Trp Gly Gln Gly Thr Thr Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcactc tcagtagtta tgaa                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Leu Ser Ser Tyr Glu
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagtagag gtggtagtct gata                                          24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Arg Gly Gly Ser Leu Ile
1               5

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gtgagagacc cagcagctcg ttatcattat tattatcacg gtatggacgt c            51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Arg Asp Pro Ala Ala Arg Tyr His Tyr Tyr Tyr His Gly Met Asp
1               5                   10                  15

Val

<210> SEQ ID NO 41
<211> LENGTH: 336
<212> TYPE: DNA
<213> ORGANISM: Artificial Sequence
<220> FEATURE:
<223> OTHER INFORMATION: Synthetic

<400> SEQUENCE: 41

```
gatattgtga tgactcagtc tccactctcc ctgcccgtca cccctggaga gccggcctcc      60
atctcctgca ggtctagtca gagcctcctg cacaataatg gatataacta tttggattgg     120
tatctgcaga agccagggca gtctccacag ctcctgatct atttgggttc tagtcgggcc     180
tccgggtcc ctgacaggtt cagtggcagt ggatcaggca cagatttat actgaaaatc       240
agcagagtgg aggctgaaga tgttggggtt tattactgca tgcaagctct acaaactccg     300
tggacgttcg gccagggac caaggtggaa atcaaa                                336
```

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Arg Gly Thr Lys Val Glu Ile Lys
            100                 105                 110
```

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43

```
cagagcctcc tgcacaataa tggatataac tat                                   33
```

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

```
Gln Ser Leu Leu His Asn Asn Gly Tyr Asn Tyr
1               5                   10
```

<210> SEQ ID NO 45

<211> LENGTH: 9
<212> TYPE: DNA
<213> ORGANISM: Artificial Sequence
<220> FEATURE:
<223> OTHER INFORMATION: Synthetic

<400> SEQUENCE: 45 ttgggttct                                                              9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Leu Gly Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgcaagctc tacaaactcc gtggacg                                         27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Met Gln Ala Leu Gln Thr Pro Trp Thr
1               5

<210> SEQ ID NO 49
<211> LENGTH: 384
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc gtggtccagc ctggggaggtc cctgagactc     60 tcctgtgcag cctctggatt caccttcagt agttatgaca tgcactgggt ccgccaggct    120
ccaggcaagg ggctggagtg ggtggcagtt atatcatctg atggacgtga taaatactat    180
gtagactccg tgaagggccg attcaccatc tccagagaca actccaagaa cacgctttat    240
ctgcaaatga acagcctgag agctgaggac acggctgttt attactgtgc gaaagagatg    300
gtgtattacg atattttgac tggttatcat aactactacg gtatggacgt ctggggccaa    360
gggaccacgg tcaccgtctc ctca                                           384

<210> SEQ ID NO 50
<211> LENGTH: 128
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Ile Ser Ser Asp Gly Arg Asp Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser Ser
        115                 120                 125

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagtta tgac                                          24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Asp
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atatcatctg atggacgtga taaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Asp Gly Arg Asp Lys
1               5

<210> SEQ ID NO 55

<210> SEQ ID NO 55
<211> LENGTH: 63
<212> TYPE: DNA
<213> ORGANISM: Artificial Sequence
<220> FEATURE:
<223> OTHER INFORMATION: Synthetic

<400> SEQUENCE: 55

```
gcgaaagaga tggtgtatta cgatattttg actggttatc ataactacta cggtatggac    60
gtc                                                                  63
```

<210> SEQ ID NO 56
<211> LENGTH: 21
<212> TYPE: PRT
<213> ORGANISM: Artificial Sequence
<220> FEATURE:
<223> OTHER INFORMATION: Synthetic

<400> SEQUENCE: 56

Ala Lys Glu Met Val Tyr Tyr Asp Ile Leu Thr Gly Tyr His Asn Tyr
1               5                   10                  15

Tyr Gly Met Asp Val
            20

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57

```
gacatcgtga tgacccagtc tccatcctca ctgtctgcat ctgtaggaga cagagtcacc    60
atcacttgtc gggcgagtca gggcattaac aattatttag cctggtttca gcagaaacca   120
gggaaagccc ctaagtccct gatccatact gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatactt accctctcac tttcggcgga   300
gggaccaaag tggagatcaa acga                                          324
```

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys Arg

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatta acaattat                                                   18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Asn Asn Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 actgcatcc                                                              9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Thr Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atacttaccc tctcact                                          27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Thr Tyr Pro Leu Thr
1               5

<210> SEQ ID NO 65

<211> LENGTH: 381
<212> TYPE: DNA
<213> ORGANISM: Artificial Sequence
<220> FEATURE:
<223> OTHER INFORMATION: Synthetic

<400> SEQUENCE: 65

```
caggtgcagc tggtggagtc tgggggaggc gtggtccagc ctggggaggtc cctgagactc      60
tcctgtgcag cctctggatt caccttcagt agttatgaca tgcactgggt ccgccaggct     120
ccaggcaagg ggctggagtg ggtggcagtt atatcatctg atggacgtga taaatactat     180
gtagactccg tgaagggccg attcaccatc tccagagaca actccaagaa cacgctttat     240
ctgcaaatga acagcctgag agctgaggac acggctgttt attactgtgc gaaagagatg     300
gtgtattacg atattttgac tggttatcat aactactacg gtatggacgt ctggggccaa     360
gggaccacgg tcaccgtctc c                                                381
```

<210> SEQ ID NO 66
<211> LENGTH: 127
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Ser Asp Gly Arg Asp Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Met Val Tyr Tyr Asp Ile Leu Thr Gly Tyr His Asn Tyr
            100                 105                 110

Tyr Gly Met Asp Val Trp Gly Gln Gly Thr Thr Val Thr Val Ser
        115                 120                 125

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67

```
gacatccaga tgacccagtc tccatcctca ctgtctgcat ctgtaggaga cagagtcacc      60
atcacttgtc gggcgagtca gggcattaac aattatttag cctggtttca gcagaaacca     120
gggaaagccc ctaagtccct gatccatact gcatccagtt tgcaaagtgg ggtcccatca     180
agttcagcg gcagtggatc tgggacagat ttcactctca ccatcagcag cctgcagcct     240
gaagattttg caacttatta ctgccaacag tataatactt accctctcac tttcggcgga     300
gggaccaagg tggagatcaa a                                                321
```

```
<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

His Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Leu
                85                  90                  95

Thr Phe Gly Gly Gly Thr Lys Val Glu Ile Lys
            100                 105

```
<210> SEQ ID NO 69
<211> LENGTH: 384
<212> TYPE: DNA
<213> ORGANISM: Artificial Sequence
<220> FEATURE:
<223> OTHER INFORMATION: Synthetic

<400> SEQUENCE: 69
```
caggtgcagc tggtgcagtc tgggggaggc ttggtccagc ctggggggtc cctgagactc      60
tcctgtgcag cctccggatt cacctttagt aactatttga tgaactgggt ccgccaggct     120
ccagggaagg ggctggagtg gctggccaac atacaggaag atggaattga gaaatactat     180
gtggactctg tgaagggccg attcaccatc tccagagaca acgccaagaa ctcactgtat     240
ctgcaaatga acagcctgag agccgaggac acggctgtgt attactgtgc gagagagccc     300
tcccattacg atatttttga ctggttatgac tactattacg gtatggacgt ctggggccaa     360
gggaccacgg tcaccgtctc ctca                                             384

```
<210> SEQ ID NO 70
<211> LENGTH: 128
<212> TYPE: PRT
<213> ORGANISM: Artificial Sequence
<220> FEATURE:
<223> OTHER INFORMATION: Synthetic

<400> SEQUENCE: 70
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

-continued

```
Leu Gln Met Asn Ser Leu Arg Ala Glu Asp Thr Ala Val Tyr Tyr Cys
             85                  90                  95

Ala Arg Glu Pro Ser His Tyr Asp Ile Leu Thr Gly Tyr Asp Tyr Tyr
        100                 105                 110

Tyr Gly Met Asp Val Trp Gly Gln Gly Thr Thr Val Thr Val Ser Ser
    115                 120                 125
```

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
ggattcacct ttagtaacta tttg    24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

```
Gly Phe Thr Phe Ser Asn Tyr Leu
1               5
```

<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
atacaggaag atggaattga gaaa    24

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

```
Ile Gln Glu Asp Gly Ile Glu Lys
1               5
```

<210> SEQ ID NO 75
<211> LENGTH: 63
<212> TYPE: DNA
<213> ORGANISM: Artificial Sequence
<220> FEATURE:
<223> OTHER INFORMATION: Synthetic

<400> SEQUENCE: 75
gcgagagagc cctcccatta cgatattttg actggttatg actactatta cggtatggac    60
gtc    63

<210> SEQ ID NO 76
<211> LENGTH: 21
<212> TYPE: PRT
<213> ORGANISM: Artificial Sequence
<220> FEATURE:

<223> OTHER INFORMATION: Synthetic

<400> SEQUENCE: 76

Ala Arg Glu Pro Ser His Tyr Asp Ile Leu Thr Gly Tyr Asp Tyr Tyr
1               5                   10                  15
Tyr Gly Met Asp Val
            20

<210> SEQ ID NO 77
<211> LENGTH: 324
<212> TYPE: DNA
<213> ORGANISM: Artificial Sequence
<220> FEATURE:
<223> OTHER INFORMATION: Synthetic

<400> SEQUENCE: 77
gacatccagt tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcattctca cagtcagcag cctgcagcct     240
gaagactttg caacttatta ctgtctacag tataatagta acccattcac tttcggccct     300
gggaccaagg tggagatcaa acga                                            324

<210> SEQ ID NO 78
<211> LENGTH: 108
<212> TYPE: PRT
<213> ORGANISM: Artificial Sequence
<220> FEATURE:
<223> OTHER INFORMATION: Synthetic

<400> SEQUENCE: 78

Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Ile Leu Thr Val Ser Ser Leu Gln Pro
65                  70                  75                  80
Glu Asp Phe Ala Thr Tyr Tyr Cys Leu Gln Tyr Asn Ser Asn Pro Phe
                85                  90                  95
Thr Phe Gly Pro Gly Thr Lys Val Glu Ile Lys Arg
            100                 105

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79
cagggcatta gaaatgat                                                    18

<210> SEQ ID NO 80
<211> LENGTH: 6
<212> TYPE: PRT

<210> SEQ ID NO 80
<211> LENGTH: 5 (implied)
<213> ORGANISM: Artificial Sequence
<220> FEATURE:
<223> OTHER INFORMATION: Synthetic

<400> SEQUENCE: 80

Gln Gly Ile Arg Asn Asp
1               5

<210> SEQ ID NO 81
<211> LENGTH: 9
<212> TYPE: DNA
<213> ORGANISM: Artificial Sequence
<220> FEATURE:
<223> OTHER INFORMATION: Synthetic

<400> SEQUENCE: 81 gctgcatcc                                                                9

<210> SEQ ID NO 82
<211> LENGTH: 3
<212> TYPE: PRT
<213> ORGANISM: Artificial Sequence
<220> FEATURE:
<223> OTHER INFORMATION: Synthetic

<400> SEQUENCE: 82

Ala Ala Ser
1

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
ctacagtata atagtaaccc attcact                                            27

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Leu Gln Tyr Asn Ser Asn Pro Phe Thr
1               5

<210> SEQ ID NO 85
<211> LENGTH: 381
<212> TYPE: DNA
<213> ORGANISM: Artificial Sequence
<220> FEATURE:
<223> OTHER INFORMATION: Synthetic

<400> SEQUENCE: 85
gaggtgcagc tggtggagtc tgggggaggc ttggtccagc ctggggggtc cctgagactc        60
tcctgtgcag cctccggatt cacctttagt aactatttga tgaactgggt ccgccaggct       120
ccagggaagg ggctggagtg gctggccaac atacaggaag atggaattga gaaatactat       180
gtggactctg tgaagggccg attcaccatc tccagagaca cgccaagaa ctcactgtat        240 ctgcaaatga acagcctgag agccgaggac acggctgtgt attactgtgc gagagagccc       300

```
tcccattacg atatttgac tggttatgac tactattacg gtatggacgt ctggggccaa    360
gggaccacgg tcaccgtctc c                                             381
```

<210> SEQ ID NO 86
<211> LENGTH: 127
<212> TYPE: PRT
<213> ORGANISM: Artificial Sequence
<220> FEATURE:
<223> OTHER INFORMATION: Synthetic

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Leu
        35                  40                  45

Ala Asn Ile Gln Glu Asp Gly Ile Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ser His Tyr Asp Ile Leu Thr Gly Tyr Asp Tyr Tyr
            100                 105                 110

Tyr Gly Met Asp Val Trp Gly Gln Gly Thr Thr Val Thr Val Ser
        115                 120                 125
```

<210> SEQ ID NO 87
<211> LENGTH: 321
<212> TYPE: DNA
<213> ORGANISM: Artificial Sequence
<220> FEATURE:
<223> OTHER INFORMATION: Synthetic

<400> SEQUENCE: 87

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta acccattcac tttcggccct   300
gggaccaaag tggatatcaa a                                             321
```

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Glu Phe Ile Leu Thr Val Ser Ser Leu Gln Pro
65                  70                  75                  80

Glu Asp Phe Ala Thr Tyr Tyr Cys Leu Gln Tyr Asn Ser Asn Pro Phe
                85                  90                  95

Thr Phe Gly Pro Gly Thr Lys Val Asp Ile Lys
                100                 105

<210> SEQ ID NO 89
<211> LENGTH: 381
<212> TYPE: DNA
<213> ORGANISM: Artificial Sequence
<220> FEATURE:
<223> OTHER INFORMATION: Synthetic

<400> SEQUENCE: 89
gaggtgcagc tggtgcagtc tgggggagcc ttggtacagc ctggggggtc cctgagactc     60
tcctgtacag cctctggttt caccttcagt aactacgaca tgcactgggt ccgccaaact    120
acaggaaaag gtctggagtg gatctcagct attgatactg ctggtgacac atactatcca    180
ggctccgtga agggccgatt caccgtctcc agagaaaatg ccaagaactc ctttatctt    240 caaatgaaca gcctgagagc cggggacacg gctgtgtatt actgtgcaag ggaggggaag    300
tattacgata ttttgactgg tgactaccac tactacggta tggacgtctg gggccaaggg    360
accacggtca ccgtctcctc a                                              381

<210> SEQ ID NO 90
<211> LENGTH: 127
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Gln Ser Gly Gly Ala Leu Val Gln Pro Gly Gly
1               5                   10                  15

Ser Leu Arg Leu Ser Cys Thr Ala Ser Gly Phe Thr Phe Ser Asn Tyr
            20                  25                  30

Asp Met His Trp Val Arg Gln Thr Thr Gly Lys Gly Leu Glu Trp Ile
        35                  40                  45

Ser Ala Ile Asp Thr Ala Gly Asp Thr Tyr Tyr Pro Gly Ser Val Lys
    50                  55                  60

Gly Arg Phe Thr Val Ser Arg Glu Asn Ala Lys Asn Ser Phe Tyr Leu
65                  70                  75                  80

Gln Met Asn Ser Leu Arg Ala Gly Asp Thr Ala Val Tyr Tyr Cys Ala
                85                  90                  95

Arg Glu Gly Lys Tyr Tyr Asp Ile Leu Thr Gly Asp Tyr His Tyr Tyr
            100                 105                 110

Gly Met Asp Val Trp Gly Gln Gly Thr Thr Val Thr Val Ser Ser
        115                 120                 125

<210> SEQ ID NO 91
<211> LENGTH: 24
<212> TYPE: DNA
<213> ORGANISM: Artificial Sequence
<220> FEATURE:
<223> OTHER INFORMATION: Synthetic

<400> SEQUENCE: 91

```
ggtttcacct tcagtaacta cgac                                          24
```

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

Gly Phe Thr Phe Ser Asn Tyr Asp
1               5

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93

```
attgatactg ctggtgacac a                                             21
```

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

Ile Asp Thr Ala Gly Asp Thr
1               5

<210> SEQ ID NO 95
<211> LENGTH: 63
<212> TYPE: DNA
<213> ORGANISM: Artificial Sequence
<220> FEATURE:
<223> OTHER INFORMATION: Synthetic

<400> SEQUENCE: 95

```
gcaagggagg ggaagtatta cgatattttg actggtgact accactacta cggtatggac    60
gtc                                                                 63
```

<210> SEQ ID NO 96
<211> LENGTH: 21
<212> TYPE: PRT
<213> ORGANISM: Artificial Sequence
<220> FEATURE:
<223> OTHER INFORMATION: Synthetic

<400> SEQUENCE: 96

Ala Arg Glu Gly Lys Tyr Tyr Asp Ile Leu Thr Gly Asp Tyr His Tyr
1               5                   10                  15

Tyr Gly Met Asp Val
            20

<210> SEQ ID NO 97
<211> LENGTH: 324
<212> TYPE: DNA
<213> ORGANISM: Artificial Sequence
<220> FEATURE:
<223> OTHER INFORMATION: Synthetic

<400> SEQUENCE: 97

| | | | | | |
|---|---|---|---|---|---|
| gccatccgga | tgacccagtc | tccatcctcc | ctgtctgcat | ctgtaggaga | cagagtcacc | 60 |
| atcacttgtc | gggcaagtca | gggcattaga | aatgatttag | gctggtatca | gcagaaacca | 120 |
| gggaaagccc | ctaagcgact | gatctatgct | acatccagtt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtctacag | cataatagtt | acccgctcac | tttcggcgga | 300 |
| gggaccaagg | tggaaatcaa | acga | | | | 324 |

<210> SEQ ID NO 98
<211> LENGTH: 108
<212> TYPE: PRT
<213> ORGANISM: Artificial Sequence
<220> FEATURE:
<223> OTHER INFORMATION: Synthetic

<400> SEQUENCE: 98

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg
            100                 105

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
cagggcatta gaaatgat                                                   18

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

Gln Gly Ile Arg Asn Asp
1               5

<210> SEQ ID NO 101
<211> LENGTH: 9
<212> TYPE: DNA
<213> ORGANISM: Artificial Sequence
<220> FEATURE:
<223> OTHER INFORMATION: Synthetic

<400> SEQUENCE: 101 gctacatcc                                                                    9

<210> SEQ ID NO 102
<211> LENGTH: 3
<212> TYPE: PRT
<213> ORGANISM: Artificial Sequence
<220> FEATURE:
<223> OTHER INFORMATION: Synthetic

<400> SEQUENCE: 102

Ala Thr Ser
1

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
ctacagcata atagttaccc gctcact                                                27

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104

Leu Gln His Asn Ser Tyr Pro Leu Thr
1               5

<210> SEQ ID NO 105
<211> LENGTH: 378
<212> TYPE: DNA
<213> ORGANISM: Artificial Sequence
<220> FEATURE:
<223> OTHER INFORMATION: Synthetic

<400> SEQUENCE: 105
gaggtgcagc tggtggagtc tgggggagcc ttggtacagc ctgggggtc cctgagactc            60 tcctgtacag cctctggttt caccttcagt aactacgaca tgcactgggt ccgccaaact          120
acaggaaaag gtctggagtg gatctcagct attgatactg ctggtgacac atactatcca          180
ggctccgtga agggccgatt caccgtctcc agagaaaatg ccaagaactc cttttatctt          240
caaatgaaca gcctgagagc cggggacacg gctgtgtatt actgtgcaag ggaggggaag          300
tattacgata ttttgactgg tgactaccac tactacggta tggacgtctg gggccaaggg          360
accacggtca ccgtctcc                                                       378

<210> SEQ ID NO 106
<211> LENGTH: 126
<212> TYPE: PRT
<213> ORGANISM: Artificial Sequence
<220> FEATURE:
<223> OTHER INFORMATION: Synthetic

<400> SEQUENCE: 106

Glu Val Gln Leu Val Glu Ser Gly Gly Ala Leu Val Gln Pro Gly Gly
1               5                   10                  15

Ser Leu Arg Leu Ser Cys Thr Ala Ser Gly Phe Thr Phe Ser Asn Tyr

```
                  20                  25                  30
Asp Met His Trp Val Arg Gln Thr Thr Gly Lys Gly Leu Glu Trp Ile
             35                  40                  45
Ser Ala Ile Asp Thr Ala Gly Asp Thr Tyr Tyr Pro Gly Ser Val Lys
         50                  55                  60
Gly Arg Phe Thr Val Ser Arg Glu Asn Ala Lys Asn Ser Phe Tyr Leu
 65                  70                  75                  80
Gln Met Asn Ser Leu Arg Ala Gly Asp Thr Ala Val Tyr Tyr Cys Ala
                 85                  90                  95
Arg Glu Gly Lys Tyr Tyr Asp Ile Leu Thr Gly Asp Tyr His Tyr Tyr
            100                 105                 110
Gly Met Asp Val Trp Gly Gln Gly Thr Thr Val Thr Val Ser
            115                 120                 125

<210> SEQ ID NO 107
<211> LENGTH: 321
<212> TYPE: DNA
<213> ORGANISM: Artificial Sequence
<220> FEATURE:
<223> OTHER INFORMATION: Synthetic

<400> SEQUENCE: 107
gacatccaga tgacccagtc tccatcctcc ctgtctgcat ctgtaggaga cagagtcacc      60
atcacttgtc gggcaagtca gggcattaga aatgatttag ctggtatca gcagaaacca     120 gggaaagccc ctaagcgact gatctatgct acatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagc tggagatcaa a                                              321

<210> SEQ ID NO 108
<211> LENGTH: 107
<212> TYPE: PRT
<213> ORGANISM: Artificial Sequence
<220> FEATURE:
<223> OTHER INFORMATION: Synthetic

<400> SEQUENCE: 108

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
         35                  40                  45
Tyr Ala Thr Ser Ser Leu Gln Ser Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro Leu
                 85                  90                  95
Thr Phe Gly Gly Gly Thr Lys Leu Glu Ile Lys
            100                 105

<210> SEQ ID NO 109
<211> LENGTH: 372
<212> TYPE: DNA
<213> ORGANISM: Artificial Sequence
<220> FEATURE:
```

-continued

<223> OTHER INFORMATION: Synthetic

<400> SEQUENCE: 109

```
caggtgcagc tggtgcagtc tgggggaggc gtggtccagc ctgggaggtc cctgagactc      60
tcctgtgcag cgtctgggtt cacctttagt aactttggca tgcactgggt ccgccaggct     120
ccaggcaagg ggctggagtg ggtggcagtt atatggtttg atgaaattga taaatactat    180
gcagactccg tgaagggccg attcaccatc tccagagaca attccaagaa cacgctgtat    240
ccgcaaatga acagcctgag agccgaagac acggctgtgt attactgtgc gcgagaagat    300
tacgatattt tgactggtta ctattacgct atggacgtct ggggccaagg gaccacggtc    360
accgtctcct ca                                                        372
```

<210> SEQ ID NO 110
<211> LENGTH: 124
<212> TYPE: PRT
<213> ORGANISM: Artificial Sequence
<220> FEATURE:
<223> OTHER INFORMATION: Synthetic

<400> SEQUENCE: 110

```
Gln Val Gln Leu Val Gln Ser Gly Gly Gly Val Val Gln Pro Gly Arg
1               5                   10                  15
Ser Leu Arg Leu Ser Cys Ala Ala Ser Gly Phe Thr Phe Ser Asn Phe
            20                  25                  30
Gly Met His Trp Val Arg Gln Ala Pro Gly Lys Gly Leu Glu Trp Val
        35                  40                  45
Ala Val Ile Trp Phe Asp Glu Ile Asp Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Pro Gln Met Asn Ser Leu Arg Ala Glu Asp Thr Ala Val Tyr Tyr Cys
                85                  90                  95
Ala Arg Glu Asp Tyr Asp Ile Leu Thr Gly Tyr Tyr Tyr Ala Met Asp
            100                 105                 110
Val Trp Gly Gln Gly Thr Thr Val Thr Val Ser Ser
        115                 120
```

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111

```
gggttcacct ttagtaactt tggc                                            24
```

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

```
Gly Phe Thr Phe Ser Asn Phe Gly
1               5
```

<210> SEQ ID NO 113

<211> LENGTH: 24
<212> TYPE: DNA
<213> ORGANISM: Artificial Sequence
<220> FEATURE:
<223> OTHER INFORMATION: Synthetic

<400> SEQUENCE: 113
atatggtttg atgaaattga taaa                                          24

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Ile Trp Phe Asp Glu Ile Asp Lys
1               5

<210> SEQ ID NO 115
<211> LENGTH: 51
<212> TYPE: DNA
<213> ORGANISM: Artificial Sequence
<220> FEATURE:
<223> OTHER INFORMATION: Synthetic

<400> SEQUENCE: 115
gcgcgagaag attacgatat tttgactggt tactattacg ctatggacgt c            51

<210> SEQ ID NO 116
<211> LENGTH: 17
<212> TYPE: PRT
<213> ORGANISM: Artificial Sequence
<220> FEATURE:
<223> OTHER INFORMATION: Synthetic

<400> SEQUENCE: 116

Ala Arg Glu Asp Tyr Asp Ile Leu Thr Gly Tyr Tyr Tyr Ala Met Asp
1               5                   10                  15
Val

<210> SEQ ID NO 117
<211> LENGTH: 321
<212> TYPE: DNA
<213> ORGANISM: Artificial Sequence
<220> FEATURE:
<223> OTHER INFORMATION: Synthetic

<400> SEQUENCE: 117
gacatccaga tgacccagtc tccatcctcc ctgtctgcat ctgtaggaga cagagtcacc   60
atcacttgcc gggcaagtca gggcattaga aatgatttag gctggtatca gcagaaacca  120
gggaaagccc ctaagcgcct aatctatgct gcatcccgtt tgcaaagtgg ggtcccatcg  180
aggttcagcg gcagtggatc tgggacagaa ttcactctca caatcagcag cctgcagcct  240
gaagattttg aacttatta ctgtctacag cataatagtc accccacctt cggccaaggg  300
accaaggtgg agatcaaacg a                                            321

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Gly Thr Tyr Tyr Cys Leu Gln His Asn Ser His Pro Thr
                85                  90                  95

Phe Gly Gln Gly Thr Lys Val Glu Ile Lys Arg
            100                 105

<210> SEQ ID NO 119
<211> LENGTH: 18
<212> TYPE: DNA
<213> ORGANISM: Artificial Sequence
<220> FEATURE:
<223> OTHER INFORMATION: Synthetic

<400> SEQUENCE: 119
cagggcatta gaaatgat                                                18

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Gln Gly Ile Arg Asn Asp
1               5

<210> SEQ ID NO 121
<211> LENGTH: 9
<212> TYPE: DNA
<213> ORGANISM: Artificial Sequence
<220> FEATURE:
<223> OTHER INFORMATION: Synthetic

<400> SEQUENCE: 121 gctgcatcc                                                           9

<210> SEQ ID NO 122
<211> LENGTH: 3
<212> TYPE: PRT
<213> ORGANISM: Artificial Sequence
<220> FEATURE:
<223> OTHER INFORMATION: Synthetic

<400> SEQUENCE: 122

Ala Ala Ser
1

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ctacagcata atagtcaccc cacc                                              24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Leu Gln His Asn Ser His Pro Thr
1               5

<210> SEQ ID NO 125
<211> LENGTH: 369
<212> TYPE: DNA
<213> ORGANISM: Artificial Sequence
<220> FEATURE:
<223> OTHER INFORMATION: Synthetic

<400> SEQUENCE: 125
caggtgcagc tggtggagtc tgggggaggc gtggtccagc ctggggaggtc cctgagactc      60 tcctgtgcag cgtctgggtt cacctttagt aactttggca tgcactgggt ccgccaggct     120
ccaggcaagg ggctggagtg ggtggcagtt atatggtttg atgaaattga taaatactat     180
gcagactccg tgaagggccg attcaccatc tccagagaca attccaagaa cacgctgtat     240
ccgcaaatga acagcctgag agccgaagac acggctgtgt attactgtgc gcgagaagat     300
tacgatattt tgactggtta ctattacgct atggacgtct ggggccaagg gaccacggtc     360
accgtctcc                                                            369

<210> SEQ ID NO 126
<211> LENGTH: 123
<212> TYPE: PRT
<213> ORGANISM: Artificial Sequence
<220> FEATURE:
<223> OTHER INFORMATION: Synthetic

<400> SEQUENCE: 126

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Trp Phe Asp Glu Ile Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Pro Gln Met Asn Ser Leu Arg Ala Glu Asp Thr Ala Val Tyr Tyr Cys
                85                  90                  95

Ala Arg Glu Asp Tyr Asp Ile Leu Thr Gly Tyr Tyr Tyr Ala Met Asp
            100                 105                 110

Val Trp Gly Gln Gly Thr Thr Val Thr Val Ser
        115                 120

<210> SEQ ID NO 127
<211> LENGTH: 318
<212> TYPE: DNA
<213> ORGANISM: Artificial Sequence
<220> FEATURE:
<223> OTHER INFORMATION: Synthetic

<400> SEQUENCE: 127

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagcgcct aatctatgct gcatcccgtt tgcaaagtgg ggtcccatcg    180
aggttcagcg gcagtggatc tgggacagaa ttcactctca caatcagcag cctgcagcct    240
gaagattttg gaacttatta ctgtctacag cataatagtc accccacctt cggccaaggg    300
accaaggtgg agatcaaa                                                  318
```

<210> SEQ ID NO 128
<211> LENGTH: 106
<212> TYPE: PRT
<213> ORGANISM: Artificial Sequence
<220> FEATURE:
<223> OTHER INFORMATION: Synthetic

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Lys Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Gly Thr Tyr Tyr Cys Leu Gln His Asn Ser His Pro Thr
                85                  90                  95

Phe Gly Gln Gly Thr Lys Val Glu Ile Lys
            100                 105

<210> SEQ ID NO 129
<211> LENGTH: 381
<212> TYPE: DNA
<213> ORGANISM: Artificial Sequence
<220> FEATURE:
<223> OTHER INFORMATION: Synthetic

<400> SEQUENCE: 129

```
gaggtgcagc tggtggagtc ggggggaggc atggtacagc ctgggggtc cctgagactc       60
tcctgtgcag cctctggatt cacctccagt aactacgaca tgcactgggt ccgccaagct     120
acaggaaaag gtctggagtg gtctcaagt attgatactg ctggggacac ttactatcca      180
gactccgtga agggccgctt tatcatctcc agagaaaatg ccaaaaactc cctgtatctt     240
caaatgaata gcctgagagc cggggacacg gctgtgtatt actgtacaag ggagccccga    300
aattacgaaa ttttgactgg tcactaccac taccacggta tggacatctg ggccaaggg     360
accacggtca ccgtctcctc a                                               381
```

<210> SEQ ID NO 130
<211> LENGTH: 127

```
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Ser Ser Asn Tyr
            20                  25                  30

Asp Met His Trp Val Arg Gln Ala Thr Gly Lys Gly Leu Glu Trp Val
        35                  40                  45

Ser Ser Ile Asp Thr Ala Gly Asp Thr Tyr Tyr Pro Asp Ser Val Lys
    50                  55                  60

Gly Arg Phe Ile Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Glu Pro Arg Asn Tyr Glu Ile Leu Thr Gly His Tyr His Tyr His
            100                 105                 110

Gly Met Asp Ile Trp Gly Gln Gly Thr Thr Val Thr Val Ser Ser
        115                 120                 125

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ccagtaacta cgac                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Ser Ser Asn Tyr Asp
1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
attgatactg ctgggacac t                                              21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Asp Thr Ala Gly Asp Thr
```

<210> SEQ ID NO 135
<211> LENGTH: 63
<212> TYPE: DNA
<213> ORGANISM: Artificial Sequence
<220> FEATURE:
<223> OTHER INFORMATION: Synthetic

<400> SEQUENCE: 135
acaagggagc cccgaaatta cgaaattttg actggtcact accactacca cggtatggac    60
atc                                                                  63

<210> SEQ ID NO 136
<211> LENGTH: 21
<212> TYPE: PRT
<213> ORGANISM: Artificial Sequence
<220> FEATURE:
<223> OTHER INFORMATION: Synthetic

<400> SEQUENCE: 136

Thr Arg Glu Pro Arg Asn Tyr Glu Ile Leu Thr Gly His Tyr His Tyr
1               5                   10                  15

His Gly Met Asp Ile
            20

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137
gacatccaga tgacccagtc gccatcctcc ctgtctgcat ctgtaggaga cagagtcacc    60
atcacttgcc gggcaagtca ggccattaga aatgatttag ctggtatca gcagaaacca   120 gggaaagccc ctaaactcct gatctatact gcattcagtt tacagagtgg ggtcccatca   180
aggttcagcg gcagtaaatc tggcacagac ttcactctca ccatcagcag cctgcagcct   240
gaagattttg cgacttatta ctgtctgcag gattacacta tcctcggac gttcggccaa   300 gggaccaagg tggagatcaa acga                                           324

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Leu Ser Ala Ser Val Gly
1               5                   10                  15

Asp Arg Val Thr Ile Thr Cys Arg Ala Ser Gln Ala Ile Arg Asn Asp
                20                  25                  30

Leu Gly Trp Tyr Gln Gln Lys Pro Gly Lys Ala Pro Lys Leu Leu Ile
            35                  40                  45

Tyr Thr Ala Phe Ser Leu Gln Ser Gly Val Pro Ser Arg Phe Ser Gly
        50                  55                  60

Ser Lys Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Thr Asn Pro Arg
            85                  90                  95

Thr Phe Gly Gln Gly Thr Lys Val Glu Ile Lys Arg
        100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggccatta gaaatgat                                                 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Ala Ile Arg Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 actgcattc                                                            9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Thr Ala Phe
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctgcaggatt acactaatcc tcggacg                                       27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln Asp Tyr Thr Asn Pro Arg Thr

<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145

```
gaggtgcagc tggtggagtc ggggggaggc atggtacagc ctggggggtc cctgagactc    60
tcctgtgcag cctctggatt cacctccagt aactacgaca tgcactgggt ccgccaagct   120
acaggaaaag gtctggagtg gtctcaagt attgatactg ctggggacac ttactatcca   180
gactccgtga agggccgctt tatcatctcc agagaaaatg ccaaaaactc cctgtatctt   240
caaatgaata gcctgagagc cggggacacg gctgtgtatt actgtacaag ggagccccga   300
aattacgaaa ttttgactgg tcactaccac taccacggta tggacatctg gggccaaggg   360
accacggtca ccgtctcc                                                  378
```

<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146

```
Glu Val Gln Leu Val Glu Ser Gly Gly Gly Met Val Gln Pro Gly Gly
1               5                   10                  15
Ser Leu Arg Leu Ser Cys Ala Ala Ser Gly Phe Thr Ser Ser Asn Tyr
            20                  25                  30
Asp Met His Trp Val Arg Gln Ala Thr Gly Lys Gly Leu Glu Trp Val
        35                  40                  45
Ser Ser Ile Asp Thr Ala Gly Asp Thr Tyr Tyr Pro Asp Ser Val Lys
    50                  55                  60
Gly Arg Phe Ile Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Thr
                85                  90                  95
Arg Glu Pro Arg Asn Tyr Glu Ile Leu Thr Gly His Tyr His Tyr His
            100                 105                 110
Gly Met Asp Ile Trp Gly Gln Gly Thr Thr Val Thr Val Ser
        115                 120                 125
```

<210> SEQ ID NO 147
<211> LENGTH: 321
<212> TYPE: DNA
<213> ORGANISM: Artificial Sequence
<220> FEATURE:
<223> OTHER INFORMATION: Synthetic

<400> SEQUENCE: 147

```
gccatccaga tgacccagtc gccatcctcc ctgtctgcat ctgtaggaga cagagtcacc    60
atcacttgcc gggcaagtca ggccattaga aatgatttag ctggtatca gcagaaacca   120
gggaaagccc ctaaactcct gatctatact gcattcagtt tacagagtgg ggtcccatca   180
aggttcagcg gcagtaaatc tggcacagac ttcactctca ccatcagcag cctgcagcct   240
gaagattttg cgacttatta ctgtctgcag gattacacta atcctcggac gttcggccaa   300
```
gggaccaagg tggaaatcaa a                                          321

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Leu Leu Ile
        35                  40                  45

Tyr Thr Ala Phe Ser Leu Gln Ser Gly Val Pro Ser Arg Phe Ser Gly
    50                  55                  60

Ser Lys Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Thr Asn Pro Arg
                85                  90                  95

Thr Phe Gly Gln Gly Thr Lys Val Glu Ile Lys
            100                 105

<210> SEQ ID NO 149
<211> LENGTH: 357
<212> TYPE: DNA
<213> ORGANISM: Artificial Sequence
<220> FEATURE:
<223> OTHER INFORMATION: synthetic

<400> SEQUENCE: 149
caggtgcagc tggtggagtc tgggggaggc gtggtccagc ctggggaggtc cctgagactc    60 tcctgtgcag cctctggatt cgccttcagt aactatggca tgcactgggt ccgccaggct   120
ccaggcaagg ggctggaatg ggtgacattt atatcatatg atggaagtaa taaatactat   180
gcagactccg tgaagggccg attcaccatc tccagagaca attccaagaa cacgctgtat   240
ctgcaagtga acagcctgag agctgaggac acggctgtgt attactgtgc gaaagaagca   300
gtattagctg ccctctttga ctactggggc cagggaaccc tggtcaccgt ctcctca      357

<210> SEQ ID NO 150
<211> LENGTH: 119
<212> TYPE: PRT
<213> ORGANISM: Artificial Sequence
<220> FEATURE:
<223> OTHER INFORMATION: synthetic

<400> SEQUENCE: 150

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Asn Tyr
            20                  25                  30

Gly Met His Trp Val Arg Gln Ala Pro Gly Lys Gly Leu Glu Trp Val
        35                  40                  45

Thr Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Val Asn Ser Leu Arg Ala Glu Asp Thr Ala Val Tyr Tyr Cys
                        85                  90                  95
Ala Lys Glu Ala Val Leu Ala Ala Leu Phe Asp Tyr Trp Gly Gln Gly
            100                 105                 110
Thr Leu Val Thr Val Ser Ser
        115
```

```
<210> SEQ ID NO 151
<211> LENGTH: 24
<212> TYPE: DNA
<213> ORGANISM: Artificial Sequence
<220> FEATURE:
<223> OTHER INFORMATION: synthetic

<400> SEQUENCE: 151
ggattcgcct tcagtaacta tggc                                          24

<210> SEQ ID NO 152
<211> LENGTH: 8
<212> TYPE: PRT
<213> ORGANISM: Artificial Sequence
<220> FEATURE:
<223> OTHER INFORMATION: synthetic

<400> SEQUENCE: 152

Gly Phe Ala Phe Ser Asn Tyr Gly
1               5

<210> SEQ ID NO 153
<211> LENGTH: 24
<212> TYPE: DNA
<213> ORGANISM: Artificial Sequence
<220> FEATURE:
<223> OTHER INFORMATION: synthetic

<400> SEQUENCE: 153
atatcatatg atggaagtaa taaa                                          24

<210> SEQ ID NO 154
<211> LENGTH: 8
<212> TYPE: PRT
<213> ORGANISM: Artificial Sequence
<220> FEATURE:
<223> OTHER INFORMATION: synthetic

<400> SEQUENCE: 154

Ile Ser Tyr Asp Gly Ser Asn Lys
1               5

<210> SEQ ID NO 155
<211> LENGTH: 36
<212> TYPE: DNA
<213> ORGANISM: Artificial Sequence
<220> FEATURE:
<223> OTHER INFORMATION: synthetic

<400> SEQUENCE: 155
gcgaaagaag cagtattagc tgccctcttt gactac                             36

<210> SEQ ID NO 156
<211> LENGTH: 12
<212> TYPE: PRT
<213> ORGANISM: Artificial Sequence
<220> FEATURE:
```

<223> OTHER INFORMATION: synthetic

<400> SEQUENCE: 156

Ala Lys Glu Ala Val Leu Ala Ala Leu Phe Asp Tyr
1               5                   10

<210> SEQ ID NO 157
<211> LENGTH: 336
<212> TYPE: DNA
<213> ORGANISM: Artificial Sequence
<220> FEATURE:
<223> OTHER INFORMATION: synthetic

<400> SEQUENCE: 157
gacatcgtga tgacccagtc tccagactcc ctggctgtgt ctctgggcga gagggccacc      60
atcaactgca gtccagcca gagtgtttta tacagctcca acaatcagaa ctacttagct      120
tggtaccagc agaaaccagg acagcctcct aagctgctca tttactgggc atctacccgg    180
gaatccgggg tccctgaccg attcagtggc agcgggtctg ggacagattt cactctcacc    240
atcaacagcc tgcaggctga agatgtggca gtttattact gtcagcaata ttatagtact    300
cctacgttcg gccaagggac caaggtggaa atcaaa                              336

<210> SEQ ID NO 158
<211> LENGTH: 112
<212> TYPE: PRT
<213> ORGANISM: Artificial Sequence
<220> FEATURE:
<223> OTHER INFORMATION: synthetic

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Gln Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Thr Phe Gly Gln Gly Thr Lys Val Glu Ile Lys
            100                 105                 110

<210> SEQ ID NO 159
<211> LENGTH: 36
<212> TYPE: DNA
<213> ORGANISM: Artificial Sequence
<220> FEATURE:
<223> OTHER INFORMATION: synthetic

<400> SEQUENCE: 159
cagagtgttt tatacagctc caacaatcag aactac                               36

<210> SEQ ID NO 160
<211> LENGTH: 12
<212> TYPE: PRT
<213> ORGANISM: Artificial Sequence
<220> FEATURE:
<223> OTHER INFORMATION: synthetic

<400> SEQUENCE: 160

Gln Ser Val Leu Tyr Ser Ser Asn Asn Gln Asn Tyr
1               5                   10

<210> SEQ ID NO 161
<211> LENGTH: 9
<212> TYPE: DNA
<213> ORGANISM: Artificial Sequence
<220> FEATURE:
<223> OTHER INFORMATION: synthetic

<400> SEQUENCE: 161 tgggcatct                                                                9

<210> SEQ ID NO 162
<211> LENGTH: 3
<212> TYPE: PRT
<213> ORGANISM: Artificial Sequence
<220> FEATURE:
<223> OTHER INFORMATION: synthetic

<400> SEQUENCE: 162

Trp Ala Ser
1

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
cagcaatatt atagtactcc tacg                                              24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gln Gln Tyr Tyr Ser Thr Pro Thr
1               5

<210> SEQ ID NO 165
<211> LENGTH: 357
<212> TYPE: DNA
<213> ORGANISM: Artificial Sequence
<220> FEATURE:
<223> OTHER INFORMATION: synthetic

<400> SEQUENCE: 165
caggtgcagc tggtggagtc tgggggaggc gtggtccagc ctggggaggtc cctgagactc      60 tcctgtgcag cctctggatt cacgttcaat acctatggca tgcactgggt ccgccaggct     120
ccagtcaagg ggctggagtg ggtggcattt atatcaaatg ataagagtaa tacattctat     180
gcagactccg tgaagggccg attcaccatc tccagagaca attccaagaa cacgctgttt     240
ctggaaatga acagcctgac agctgaggac acggctgttt attactgtgc gaaagagtcc     300
attttagcag ccctctttga ctactggggc cagggaaccc tggtcactgt ctcctca       357

<210> SEQ ID NO 166
<211> LENGTH: 119
<212> TYPE: PRT
<213> ORGANISM: Artificial Sequence
<220> FEATURE:
<223> OTHER INFORMATION: synthetic

<400> SEQUENCE: 166

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Thr Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 167
<211> LENGTH: 24
<212> TYPE: DNA
<213> ORGANISM: Artificial Sequence
<220> FEATURE:
<223> OTHER INFORMATION: synthetic

<400> SEQUENCE: 167
ggattcacgt tcaataccta tggc                                          24

<210> SEQ ID NO 168
<211> LENGTH: 8
<212> TYPE: PRT
<213> ORGANISM: Artificial Sequence
<220> FEATURE:
<223> OTHER INFORMATION: synthetic

<400> SEQUENCE: 168

Gly Phe Thr Phe Asn Thr Tyr Gly
1               5

<210> SEQ ID NO 169
<211> LENGTH: 24
<212> TYPE: DNA
<213> ORGANISM: Artificial Sequence
<220> FEATURE:
<223> OTHER INFORMATION: synthetic

<400> SEQUENCE: 169
atatcaaatg ataagagtaa taca                                          24

<210> SEQ ID NO 170
<211> LENGTH: 8
<212> TYPE: PRT
<213> ORGANISM: Artificial Sequence
<220> FEATURE:
<223> OTHER INFORMATION: synthetic

<400> SEQUENCE: 170

```
Ile Ser Asn Asp Lys Ser Asn Thr
1               5
```

<210> SEQ ID NO 171
<211> LENGTH: 36
<212> TYPE: DNA
<213> ORGANISM: Artificial Sequence
<220> FEATURE:
<223> OTHER INFORMATION: synthetic

<400> SEQUENCE: 171
gcgaaagagt ccattttagc agccctcttt gactac                                     36

<210> SEQ ID NO 172
<211> LENGTH: 12
<212> TYPE: PRT
<213> ORGANISM: Artificial Sequence
<220> FEATURE:
<223> OTHER INFORMATION: synthetic

<400> SEQUENCE: 172

```
Ala Lys Glu Ser Ile Leu Ala Ala Leu Phe Asp Tyr
1               5                   10
```

<210> SEQ ID NO 173
<211> LENGTH: 336
<212> TYPE: DNA
<213> ORGANISM: Artificial Sequence
<220> FEATURE:
<223> OTHER INFORMATION: synthetic

<400> SEQUENCE: 173
gacatcgtga tgacccagtc tccagactcc ctggctgtgt ctctgggcga gagggccacc    60
atcaactgca agtccagcca gagtgtttta tacagctcca acaataagaa ttacttagct   120
tggtaccaac agaaaccaag acagcctctt aaactactca tttactgggc atctattcgg   180
gaatccgggg tccctgaccg attcagtggc agcgggtctg ggacagattt cactctcacc   240
atcagcagcc tgcaggctga agatgtggca gtttattact gtcagcaatt ttatagtgtt   300
cccactttg gccaggggac caagctggag atcaaa                              336

<210> SEQ ID NO 174
<211> LENGTH: 112
<212> TYPE: PRT
<213> ORGANISM: Artificial Sequence
<220> FEATURE:
<223> OTHER INFORMATION: synthetic

<400> SEQUENCE: 174

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Phe Tyr Ser Val Pro Thr Phe Gly Gln Gly Thr Lys Leu Glu Ile Lys
            100                 105                 110

<210> SEQ ID NO 175
<211> LENGTH: 36
<212> TYPE: DNA
<213> ORGANISM: Artificial Sequence
<220> FEATURE:
<223> OTHER INFORMATION: synthetic

<400> SEQUENCE: 175
cagagtgttt tatacagctc caacaataag aattac                           36

<210> SEQ ID NO 176
<211> LENGTH: 12
<212> TYPE: PRT
<213> ORGANISM: Artificial Sequence
<220> FEATURE:
<223> OTHER INFORMATION: synthetic

<400> SEQUENCE: 176

Gln Ser Val Leu Tyr Ser Ser Asn Asn Lys Asn Tyr
1               5                   10

<210> SEQ ID NO 177
<211> LENGTH: 9
<212> TYPE: DNA
<213> ORGANISM: Artificial Sequence
<220> FEATURE:
<223> OTHER INFORMATION: synthetic

<400> SEQUENCE: 177 tgggcatct                                                          9

<210> SEQ ID NO 178
<211> LENGTH: 3
<212> TYPE: PRT
<213> ORGANISM: Artificial Sequence
<220> FEATURE:
<223> OTHER INFORMATION: synthetic

<400> SEQUENCE: 178

Trp Ala Ser
1

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
cagcaatttt atagtgttcc cact                                        24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gln Gln Phe Tyr Ser Val Pro Thr
1               5

<210> SEQ ID NO 181
<211> LENGTH: 357
<212> TYPE: DNA
<213> ORGANISM: Artificial Sequence
<220> FEATURE:
<223> OTHER INFORMATION: synthetic

<400> SEQUENCE: 181

```
caggtgcagc tggtggagtc tgggggaggc gtggtccagc ctgggaggtc cctgagactc      60
tcctgtgcag cctctggatt cacgtttagt acctttggca tgcactgggt ccgccaggct     120
ccagtcaagg ggctggagtg ggtggctttt atatcaaatg ataagaataa taaattctat     180
gcagactccg tgaagggccg attcaccatc tccagagaca attccaggga cacgctatat     240
ctgcaaatga acagcctgac acctgaggac acggctgttt attactgtgc gaaagagtcc     300
attttagcag ccctctttga ctactggggc cagggaaccc tggtcaccgt ctcctca       357
```

<210> SEQ ID NO 182
<211> LENGTH: 119
<212> TYPE: PRT
<213> ORGANISM: Artificial Sequence
<220> FEATURE:
<223> OTHER INFORMATION: synthetic

<400> SEQUENCE: 182

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Val Lys Gly Leu Glu Trp Val
        35                  40                  45

Ala Phe Ile Ser Asn Asp Lys Asn Asn Lys Phe Tyr Ala Asp Ser Val
    50                  55                  60

Lys Gly Arg Phe Thr Ile Ser Arg Asp Asn Ser Arg Asp Thr Leu Tyr
65                  70                  75                  80

Leu Gln Met Asn Ser Leu Thr Pro Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115
```

<210> SEQ ID NO 183
<211> LENGTH: 24
<212> TYPE: DNA
<213> ORGANISM: Artificial Sequence
<220> FEATURE:
<223> OTHER INFORMATION: synthetic

<400> SEQUENCE: 183

```
ggattcacgt ttagtacctt tggc                                              24
```

<210> SEQ ID NO 184
<211> LENGTH: 8
<212> TYPE: PRT
<213> ORGANISM: Artificial Sequence
<220> FEATURE:
<223> OTHER INFORMATION: synthetic

<400> SEQUENCE: 184

```
Gly Phe Thr Phe Ser Thr Phe Gly
1               5
```

<210> SEQ ID NO 185
<211> LENGTH: 24
<212> TYPE: DNA
<213> ORGANISM: Artificial Sequence
<220> FEATURE:
<223> OTHER INFORMATION: synthetic

<400> SEQUENCE: 185
atatcaaatg ataagaataa taaa                                          24

<210> SEQ ID NO 186
<211> LENGTH: 8
<212> TYPE: PRT
<213> ORGANISM: Artificial Sequence
<220> FEATURE:
<223> OTHER INFORMATION: synthetic

<400> SEQUENCE: 186

Ile Ser Asn Asp Lys Asn Asn Lys
1               5

<210> SEQ ID NO 187
<211> LENGTH: 36
<212> TYPE: DNA
<213> ORGANISM: Artificial Sequence
<220> FEATURE:
<223> OTHER INFORMATION: synthetic

<400> SEQUENCE: 187
gcgaaagagt ccattttagc agccctcttt gactac                             36

<210> SEQ ID NO 188
<211> LENGTH: 12
<212> TYPE: PRT
<213> ORGANISM: Artificial Sequence
<220> FEATURE:
<223> OTHER INFORMATION: synthetic

<400> SEQUENCE: 188

Ala Lys Glu Ser Ile Leu Ala Ala Leu Phe Asp Tyr
1               5                   10

<210> SEQ ID NO 189
<211> LENGTH: 336
<212> TYPE: DNA
<213> ORGANISM: Artificial Sequence
<220> FEATURE:
<223> OTHER INFORMATION: synthetic

<400> SEQUENCE: 189
gacatcgtga tgacccagtc tccagactcc ctggctgtgt ctctgggcga gagggccacc    60
atcaactgca agtccagcca gagtgtttta tacagctcca acaataaaaa ttacttagct   120
tggtaccagc agaaaccagg acagcctctt aaacttctca tttactgggc atctattcgg   180
gaatccgggg tccctgaccg attcagtggc agcgggtctg ggacagattt cactctcacc   240
atcagcagcc tgcaggctga agatgtggca gtttattact gtcagcaatt ttatactgtt   300 cccactttg gcctggggac caagctggag atcaaa                              336

<210> SEQ ID NO 190
<211> LENGTH: 112
<212> TYPE: PRT
<213> ORGANISM: Artificial Sequence
<220> FEATURE:

<223> OTHER INFORMATION: synthetic

<400> SEQUENCE: 190

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Thr Val Pro Thr Phe Gly Leu Gly Thr Lys Leu Glu Ile Lys
            100                 105                 110

<210> SEQ ID NO 191
<211> LENGTH: 36
<212> TYPE: DNA
<213> ORGANISM: Artificial Sequence
<220> FEATURE:
<223> OTHER INFORMATION: synthetic

<400> SEQUENCE: 191
cagagtgttt tatacagctc caacaataaa aattac                               36

<210> SEQ ID NO 192
<211> LENGTH: 12
<212> TYPE: PRT
<213> ORGANISM: Artificial Sequence
<220> FEATURE:
<223> OTHER INFORMATION: synthetic

<400> SEQUENCE: 192

Gln Ser Val Leu Tyr Ser Ser Asn Asn Lys Asn Tyr
1               5                   10

<210> SEQ ID NO 193
<211> LENGTH: 9
<212> TYPE: DNA
<213> ORGANISM: Artificial Sequence
<220> FEATURE:
<223> OTHER INFORMATION: synthetic

<400> SEQUENCE: 193 tgggcatct                                                              9

<210> SEQ ID NO 194
<211> LENGTH: 3
<212> TYPE: PRT
<213> ORGANISM: Artificial Sequence
<220> FEATURE:
<223> OTHER INFORMATION: synthetic

<400> SEQUENCE: 194

Trp Ala Ser
1

<210> SEQ ID NO 195
<211> LENGTH: 24
<212> TYPE: DNA

```
<213> ORGANISM: Artificial Sequence
<220> FEATURE:
<223> OTHER INFORMATION: synthetic

<400> SEQUENCE: 195
cagcaatttt atactgttcc cact                                              24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gln Gln Phe Tyr Thr Val Pro Thr
1               5

<210> SEQ ID NO 197
<211> LENGTH: 357
<212> TYPE: DNA
<213> ORGANISM: Artificial Sequence
<220> FEATURE:
<223> OTHER INFORMATION: synthetic

<400> SEQUENCE: 197
caggtgcagc tggtggagtc tgggggaggc gtggtccagc ctgggaggtc cctgagactc        60
tcctgtgtag cctctggatt caccttcagg aactatgaca tgcactgggt ccgccaggct       120
cctggcaagg ggctggaatg ggtggcagtt acatcatctg atggacttaa taaattctat       180
tcagactccg tgaagggccg attcaccatc tccagagaca attccaagaa cacgctgtct       240
ctgcaaatta ccggcctgag agctgaggac acggctgtgt attactgtgc gaaagagtcc       300
attttagcag ccctctttga ctactggggc cagggaaccc tggtcaccgt ctcctca         357

<210> SEQ ID NO 198
<211> LENGTH: 119
<212> TYPE: PRT
<213> ORGANISM: Artificial Sequence
<220> FEATURE:
<223> OTHER INFORMATION: synthetic

<400> SEQUENCE: 198

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Arg Asn Tyr
            20                  25                  30

Asp Met His Trp Val Arg Gln Ala Pro Gly Lys Gly Leu Glu Trp Val
        35                  40                  45

Ala Val Thr Ser Ser Asp Gly Leu Asn Lys Phe Tyr Ser Asp Ser Val
    50                  55                  60

Lys Gly Arg Phe Thr Ile Ser Arg Asp Asn Ser Lys Asn Thr Leu Ser
65                  70                  75                  80

Leu Gln Ile Thr Gly Leu Arg Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 199
```

<211> LENGTH: 24
<212> TYPE: DNA
<213> ORGANISM: Artificial Sequence
<220> FEATURE:
<223> OTHER INFORMATION: synthetic

<400> SEQUENCE: 199
ggattcacct tcaggaacta tgac            24

<210> SEQ ID NO 200
<211> LENGTH: 8
<212> TYPE: PRT
<213> ORGANISM: Artificial Sequence
<220> FEATURE:
<223> OTHER INFORMATION: synthetic

<400> SEQUENCE: 200

Gly Phe Thr Phe Arg Asn Tyr Asp
1               5

<210> SEQ ID NO 201
<211> LENGTH: 24
<212> TYPE: DNA
<213> ORGANISM: Artificial Sequence
<220> FEATURE:
<223> OTHER INFORMATION: synthetic

<400> SEQUENCE: 201
acatcatctg atggacttaa taaa            24

<210> SEQ ID NO 202
<211> LENGTH: 8
<212> TYPE: PRT
<213> ORGANISM: Artificial Sequence
<220> FEATURE:
<223> OTHER INFORMATION: synthetic

<400> SEQUENCE: 202

Thr Ser Ser Asp Gly Leu Asn Lys
1               5

<210> SEQ ID NO 203
<211> LENGTH: 36
<212> TYPE: DNA
<213> ORGANISM: Artificial Sequence
<220> FEATURE:
<223> OTHER INFORMATION: synthetic

<400> SEQUENCE: 203
gcgaaagagt ccattttagc agccctcttt gactac            36

<210> SEQ ID NO 204
<211> LENGTH: 12
<212> TYPE: PRT
<213> ORGANISM: Artificial Sequence
<220> FEATURE:
<223> OTHER INFORMATION: synthetic

<400> SEQUENCE: 204

Ala Lys Glu Ser Ile Leu Ala Ala Leu Phe Asp Tyr
1               5                   10

<210> SEQ ID NO 205
<211> LENGTH: 336
<212> TYPE: DNA
<213> ORGANISM: Artificial Sequence
<220> FEATURE:

<223> OTHER INFORMATION: synthetic

<400> SEQUENCE: 205

```
gacatcgtga tgacccagtc tccagactcc ctggctgtgt ctctgggcga gagggccacc    60
atcaactgca agtccagcca gagtgtttta tacagctcca acaataagaa ctacttggct   120
tggtaccagc agaaaccagg acagcctcct aagctgctct tttactgggc atctacccgg   180
gaatccgggg tccctgaccg attcagtggc agcgggtctg ggacagattt cactctcacc   240
atcagcagcc tgcaggctga agatgtggca gtttattact gtcagcaaca ttatactact   300
cccactttg gccaggggac caagctggag atcaaa                              336
```

<210> SEQ ID NO 206
<211> LENGTH: 112
<212> TYPE: PRT
<213> ORGANISM: Artificial Sequence
<220> FEATURE:
<223> OTHER INFORMATION: synthetic

<400> SEQUENCE: 206

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Thr Pro Thr Phe Gly Gln Gly Thr Lys Leu Glu Ile Lys
            100                 105                 110
```

<210> SEQ ID NO 207
<211> LENGTH: 36
<212> TYPE: DNA
<213> ORGANISM: Artificial Sequence
<220> FEATURE:
<223> OTHER INFORMATION: synthetic

<400> SEQUENCE: 207

```
cagagtgttt tatacagctc caacaataag aactac                              36
```

<210> SEQ ID NO 208
<211> LENGTH: 12
<212> TYPE: PRT
<213> ORGANISM: Artificial Sequence
<220> FEATURE:
<223> OTHER INFORMATION: synthetic

<400> SEQUENCE: 208

```
Gln Ser Val Leu Tyr Ser Ser Asn Asn Lys Asn Tyr
1               5                   10
```

<210> SEQ ID NO 209
<211> LENGTH: 9
<212> TYPE: DNA
<213> ORGANISM: Artificial Sequence
<220> FEATURE:
<223> OTHER INFORMATION: synthetic

<400> SEQUENCE: 209 tgggcatct                                                              9

<210> SEQ ID NO 210
<211> LENGTH: 3
<212> TYPE: PRT
<213> ORGANISM: Artificial Sequence
<220> FEATURE:
<223> OTHER INFORMATION: synthetic

<400> SEQUENCE: 210

Trp Ala Ser
1

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
cagcaacatt atactactcc cact                                            24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gln Gln His Tyr Thr Thr Pro Thr
1               5

<210> SEQ ID NO 213
<211> LENGTH: 357
<212> TYPE: DNA
<213> ORGANISM: Artificial Sequence
<220> FEATURE:
<223> OTHER INFORMATION: synthetic

<400> SEQUENCE: 213
caggtgcagc tggtggagtc tgggggaggc gtggtccagc ctggggaggtc cctgagactc     60 tcctgtgcag cctctggatt caccttcagt agctatggca tgcactgggt ccgccagact    120
ccgggcaagg ggctggagtg ggtggcattt atatcatatg atggaaataa taaatactat    180
gcagactccg tgaagggccg attcaccatc tccagagaca attccaagaa cacgctgttt    240
ctgcaaatga acagcctgag agctgaggac acggctgtgt attactgtgc gaaagagtcc    300
attttagcag ccctctttga ctactggggc cagggaaccc tggtcaccgt ctcctca      357

<210> SEQ ID NO 214
<211> LENGTH: 119
<212> TYPE: PRT
<213> ORGANISM: Artificial Sequence
<220> FEATURE:
<223> OTHER INFORMATION: synthetic

<400> SEQUENCE: 214

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                20                  25                  30
Gly Met His Trp Val Arg Gln Thr Pro Gly Lys Gly Leu Glu Trp Val
            35                  40                  45

Ala Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 215
<211> LENGTH: 24
<212> TYPE: DNA
<213> ORGANISM: Artificial Sequence
<220> FEATURE:
<223> OTHER INFORMATION: synthetic

<400> SEQUENCE: 215
ggattcacct tcagtagcta tggc                                         24

<210> SEQ ID NO 216
<211> LENGTH: 8
<212> TYPE: PRT
<213> ORGANISM: Artificial Sequence
<220> FEATURE:
<223> OTHER INFORMATION: synthetic

<400> SEQUENCE: 216

Gly Phe Thr Phe Ser Ser Tyr Gly
 1               5

<210> SEQ ID NO 217
<211> LENGTH: 24
<212> TYPE: DNA
<213> ORGANISM: Artificial Sequence
<220> FEATURE:
<223> OTHER INFORMATION: synthetic

<400> SEQUENCE: 217
atatcatatg atggaaataa taaa                                         24

<210> SEQ ID NO 218
<211> LENGTH: 8
<212> TYPE: PRT
<213> ORGANISM: Artificial Sequence
<220> FEATURE:
<223> OTHER INFORMATION: synthetic

<400> SEQUENCE: 218

Ile Ser Tyr Asp Gly Asn Asn Lys
 1               5

<210> SEQ ID NO 219
<211> LENGTH: 36
<212> TYPE: DNA
<213> ORGANISM: Artificial Sequence
<220> FEATURE:
<223> OTHER INFORMATION: synthetic

<400> SEQUENCE: 219
```
gcgaaagagt ccattttagc agccctcttt gactac    36

<210> SEQ ID NO 220
<211> LENGTH: 12
<212> TYPE: PRT
<213> ORGANISM: Artificial Sequence
<220> FEATURE:
<223> OTHER INFORMATION: synthetic

<400> SEQUENCE: 220

Ala Lys Glu Ser Ile Leu Ala Ala Leu Phe Asp Tyr
1               5                   10

<210> SEQ ID NO 221
<211> LENGTH: 336
<212> TYPE: DNA
<213> ORGANISM: Artificial Sequence
<220> FEATURE:
<223> OTHER INFORMATION: synthetic

<400> SEQUENCE: 221
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaacctgg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca ctttattact gtcaacaata ttataatact   300 cccactttg gccaggggac caagctggag atcaaa                              336

<210> SEQ ID NO 222
<211> LENGTH: 112
<212> TYPE: PRT
<213> ORGANISM: Artificial Sequence
<220> FEATURE:
<223> OTHER INFORMATION: synthetic

<400> SEQUENCE: 222

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Tyr Asn Thr Pro Thr Phe Gly Gln Gly Thr Lys Leu Glu Ile Lys
            100                 105                 110

<210> SEQ ID NO 223
<211> LENGTH: 36
<212> TYPE: DNA
<213> ORGANISM: Artificial Sequence
<220> FEATURE:
<223> OTHER INFORMATION: synthetic

<400> SEQUENCE: 223

```
cagagtgttt tatacagctc caacaataag aactac                                   36
```

<210> SEQ ID NO 224
<211> LENGTH: 12
<212> TYPE: PRT
<213> ORGANISM: Artificial Sequence
<220> FEATURE:
<223> OTHER INFORMATION: synthetic

<400> SEQUENCE: 224

```
Gln Ser Val Leu Tyr Ser Ser Asn Asn Lys Asn Tyr
1               5                   10
```

<210> SEQ ID NO 225
<211> LENGTH: 9
<212> TYPE: DNA
<213> ORGANISM: Artificial Sequence
<220> FEATURE:
<223> OTHER INFORMATION: synthetic

<400> SEQUENCE: 225

```
tgggcatct                                                                  9
```

<210> SEQ ID NO 226
<211> LENGTH: 3
<212> TYPE: PRT
<213> ORGANISM: Artificial Sequence
<220> FEATURE:
<223> OTHER INFORMATION: synthetic

<400> SEQUENCE: 226

```
Trp Ala Ser
1
```

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227

```
caacaatatt ataatactcc cact                                                24
```

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

```
Gln Gln Tyr Tyr Asn Thr Pro Thr
1               5
```

<210> SEQ ID NO 229
<211> LENGTH: 357
<212> TYPE: DNA
<213> ORGANISM: Artificial Sequence
<220> FEATURE:
<223> OTHER INFORMATION: synthetic

<400> SEQUENCE: 229

```
caggtgcagc tggtggagtc tgggggaggc gtggtccagc ctgggaggtc cctgagactc         60
tcctgtgcag cctctggatt caccttcagt agctatggca tgcactgggt ccgccaggct        120
```

```
ccagtcaagg ggctggagtg ggtggcattt atatcatatg atggaagtaa taaatactat      180
gcagactccg tgaagggccg attcaccatc tccagagaca attccaagaa cacgctgtat      240
ctccaaatga acagcctgac agctgaggac acggctgttt attactgtgc gaaagagtcc      300
attttagcag ccctctttga ctactggggc cagggaaccc tggtcaccgt ctcctca         357
```

<210> SEQ ID NO 230
<211> LENGTH: 119
<212> TYPE: PRT
<213> ORGANISM: Artificial Sequence
<220> FEATURE:
<223> OTHER INFORMATION: synthetic

<400> SEQUENCE: 230

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115
```

<210> SEQ ID NO 231
<211> LENGTH: 24
<212> TYPE: DNA
<213> ORGANISM: Artificial Sequence
<220> FEATURE:
<223> OTHER INFORMATION: synthetic

<400> SEQUENCE: 231

```
ggattcacct tcagtagcta tggc                                              24
```

<210> SEQ ID NO 232
<211> LENGTH: 8
<212> TYPE: PRT
<213> ORGANISM: Artificial Sequence
<220> FEATURE:
<223> OTHER INFORMATION: synthetic

<400> SEQUENCE: 232

```
Gly Phe Thr Phe Ser Ser Tyr Gly
1               5
```

<210> SEQ ID NO 233
<211> LENGTH: 24
<212> TYPE: DNA
<213> ORGANISM: Artificial Sequence
<220> FEATURE:
<223> OTHER INFORMATION: synthetic

<400> SEQUENCE: 233

```
atatcatatg atggaagtaa taaa                                              24
```

<210> SEQ ID NO 234
<211> LENGTH: 8
<212> TYPE: PRT
<213> ORGANISM: Artificial Sequence
<220> FEATURE:
<223> OTHER INFORMATION: synthetic

<400> SEQUENCE: 234

Ile Ser Tyr Asp Gly Ser Asn Lys
1               5

<210> SEQ ID NO 235
<211> LENGTH: 36
<212> TYPE: DNA
<213> ORGANISM: Artificial Sequence
<220> FEATURE:
<223> OTHER INFORMATION: synthetic

<400> SEQUENCE: 235
gcgaaagagt ccattttagc agccctcttt gactac                              36

<210> SEQ ID NO 236
<211> LENGTH: 12
<212> TYPE: PRT
<213> ORGANISM: Artificial Sequence
<220> FEATURE:
<223> OTHER INFORMATION: synthetic

<400> SEQUENCE: 236

Ala Lys Glu Ser Ile Leu Ala Ala Leu Phe Asp Tyr
1               5                   10

<210> SEQ ID NO 237
<211> LENGTH: 336
<212> TYPE: DNA
<213> ORGANISM: Artificial Sequence
<220> FEATURE:
<223> OTHER INFORMATION: synthetic

<400> SEQUENCE: 237
gacatcgtga tgacccagtc tccagactcc ctggctgtgt ctctgggcga gagggccacc     60
atcaactgca gtccagccag agtgttttta tacagttcca acaataagaa ctacttagct    120
tggtaccagc agaaaccaag acagcctcct aagctgctca tttactgggc atctattcgg    180
gaatccgggg tccctgaccg attcagtggc agcgggtctg ggacagattt cattctcacc    240
atcagcagcc tgcaggctga agatgtggca gtttattact gtcagcaatt ttatagtatt    300 cccactttg gccaggggac caagctggag atcaaa                               336

<210> SEQ ID NO 238
<211> LENGTH: 112
<212> TYPE: PRT
<213> ORGANISM: Artificial Sequence
<220> FEATURE:
<223> OTHER INFORMATION: synthetic

<400> SEQUENCE: 238

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Arg Gln
            35                  40                  45

```
Pro Pro Lys Leu Leu Ile Tyr Trp Ala Ser Ile Arg Glu Ser Gly Val
    50                  55                  60
Pro Asp Arg Phe Ser Gly Ser Gly Ser Gly Thr Asp Phe Ile Leu Thr
65                  70                  75                  80
Ile Ser Ser Leu Gln Ala Glu Asp Val Ala Val Tyr Tyr Cys Gln Gln
                85                  90                  95
Phe Tyr Ser Ile Pro Thr Phe Gly Gln Gly Thr Lys Leu Glu Ile Lys
            100                 105                 110
```

<210> SEQ ID NO 239
<211> LENGTH: 36
<212> TYPE: DNA
<213> ORGANISM: Artificial Sequence
<220> FEATURE:
<223> OTHER INFORMATION: synthetic

<400> SEQUENCE: 239
cagagtgttt tatacagttc aacaataag aactac        36

<210> SEQ ID NO 240
<211> LENGTH: 12
<212> TYPE: PRT
<213> ORGANISM: Artificial Sequence
<220> FEATURE:
<223> OTHER INFORMATION: synthetic

<400> SEQUENCE: 240

```
Gln Ser Val Leu Tyr Ser Ser Asn Asn Lys Asn Tyr
1               5                   10
```

<210> SEQ ID NO 241
<211> LENGTH: 9
<212> TYPE: DNA
<213> ORGANISM: Artificial Sequence
<220> FEATURE:
<223> OTHER INFORMATION: synthetic

<400> SEQUENCE: 241 tgggcatct        9

<210> SEQ ID NO 242
<211> LENGTH: 3
<212> TYPE: PRT
<213> ORGANISM: Artificial Sequence
<220> FEATURE:
<223> OTHER INFORMATION: synthetic

<400> SEQUENCE: 242

```
Trp Ala Ser
1
```

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
cagcaatttt atagtattcc cact        24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gln Gln Phe Tyr Ser Ile Pro Thr
1               5

<210> SEQ ID NO 245
<211> LENGTH: 357
<212> TYPE: DNA
<213> ORGANISM: Artificial Sequence
<220> FEATURE:
<223> OTHER INFORMATION: synthetic

<400> SEQUENCE: 245
caggtgcagc tggtggagtc tgggggaggc gtggtccagc ctggggaggtc cctgagactc    60 tcctgtgcag cctctggatt cacctttagt agctatggca tgcactgggt ccgccaggct   120
ccagtcaagg gctggagtg gtggcattt atatcaaatg ataaaagtaa taaatattat    180
gcagactcct tgaagggccg attcaccatc tccagagaca attccaagaa cacgctgtat   240
ctgcaaatga acagcctgac agctgaagac acggctgttt attactgtgc gaaagagtcc   300
attttagcag ccctctttga ctattggggc cagggaaccc tggtcaccgt ctcctca     357

<210> SEQ ID NO 246
<211> LENGTH: 119
<212> TYPE: PRT
<213> ORGANISM: Artificial Sequence
<220> FEATURE:
<223> OTHER INFORMATION: synthetic

<400> SEQUENCE: 246

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Lys Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 247
<211> LENGTH: 24
<212> TYPE: DNA
<213> ORGANISM: Artificial Sequence
<220> FEATURE:
<223> OTHER INFORMATION: synthetic

<400> SEQUENCE: 247
ggattcacct ttagtagcta tggc                                            24

<210> SEQ ID NO 248
<211> LENGTH: 8

```
<212> TYPE: PRT
<213> ORGANISM: Artificial Sequence
<220> FEATURE:
<223> OTHER INFORMATION: synthetic

<400> SEQUENCE: 248

Gly Phe Thr Phe Ser Ser Tyr Gly
1               5

<210> SEQ ID NO 249
<211> LENGTH: 24
<212> TYPE: DNA
<213> ORGANISM: Artificial Sequence
<220> FEATURE:
<223> OTHER INFORMATION: synthetic

<400> SEQUENCE: 249
atatcaaatg ataaaagtaa taaa                                          24

<210> SEQ ID NO 250
<211> LENGTH: 8
<212> TYPE: PRT
<213> ORGANISM: Artificial Sequence
<220> FEATURE:
<223> OTHER INFORMATION: synthetic

<400> SEQUENCE: 250

Ile Ser Asn Asp Lys Ser Asn Lys
1               5

<210> SEQ ID NO 251
<211> LENGTH: 36
<212> TYPE: DNA
<213> ORGANISM: Artificial Sequence
<220> FEATURE:
<223> OTHER INFORMATION: synthetic

<400> SEQUENCE: 251
gcgaaagagt ccattttagc agccctcttt gactat                             36

<210> SEQ ID NO 252
<211> LENGTH: 12
<212> TYPE: PRT
<213> ORGANISM: Artificial Sequence
<220> FEATURE:
<223> OTHER INFORMATION: synthetic

<400> SEQUENCE: 252

Ala Lys Glu Ser Ile Leu Ala Ala Leu Phe Asp Tyr
1               5                   10

<210> SEQ ID NO 253
<211> LENGTH: 336
<212> TYPE: DNA
<213> ORGANISM: Artificial Sequence
<220> FEATURE:
<223> OTHER INFORMATION: synthetic

<400> SEQUENCE: 253
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccaag acagcctcct aagctactca tttactgggc atctattcgg   180
gaatccgggg tccctgaccg attcagtggc agcgggtctg ggacagattt cactctcacc   240
atcagcagcc tgcaggctga agatgtggca gtttattact gtcaacaatt ttatagtgtt   300
``` cccactttg gccaggggac caagctggag atcaaa        336

<210> SEQ ID NO 254
<211> LENGTH: 112
<212> TYPE: PRT
<213> ORGANISM: Artificial Sequence
<220> FEATURE:
<223> OTHER INFORMATION: synthetic

<400> SEQUENCE: 254

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Arg Gln
        35                  40                  45
Pro Pro Lys Leu Leu Ile Tyr Trp Ala Ser Ile Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Phe Tyr Ser Val Pro Thr Phe Gly Gln Gly Thr Lys Leu Glu Ile Lys
            100                 105                 110

<210> SEQ ID NO 255
<211> LENGTH: 36
<212> TYPE: DNA
<213> ORGANISM: Artificial Sequence
<220> FEATURE:
<223> OTHER INFORMATION: synthetic

<400> SEQUENCE: 255
cagagtgttt tatacagctc caacaataag aactac        36

<210> SEQ ID NO 256
<211> LENGTH: 12
<212> TYPE: PRT
<213> ORGANISM: Artificial Sequence
<220> FEATURE:
<223> OTHER INFORMATION: synthetic

<400> SEQUENCE: 256

Gln Ser Val Leu Tyr Ser Ser Asn Asn Lys Asn Tyr
1               5                   10

<210> SEQ ID NO 257
<211> LENGTH: 9
<212> TYPE: DNA
<213> ORGANISM: Artificial Sequence
<220> FEATURE:
<223> OTHER INFORMATION: synthetic

<400> SEQUENCE: 257 tgggcatct        9

<210> SEQ ID NO 258
<211> LENGTH: 3
<212> TYPE: PRT
<213> ORGANISM: Artificial Sequence
<220> FEATURE:
<223> OTHER INFORMATION: synthetic

<400> SEQUENCE: 258

Trp Ala Ser
1

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259
caacaatttt atagtgttcc cact                                          24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gln Gln Phe Tyr Ser Val Pro Thr
1               5

<210> SEQ ID NO 261
<211> LENGTH: 357
<212> TYPE: DNA
<213> ORGANISM: Artificial Sequence
<220> FEATURE:
<223> OTHER INFORMATION: synthetic

<400> SEQUENCE: 261
caggtgcagc tggtggagtc tgggggaggc gtggtccagc ctgggaggtc cctgagactc     60
tcctgtgcag cctctggatt caccttcagt agctatggca tgcactgggt ccgccaggct    120
ccagtcaagg gctggagtg gtggcattt atatcatttg atggaagtaa taaatactat    180
acagactccg tgaagggccg attcaccatc tccagagaca attccaagaa cacgctgtat    240
ctccaaatga acagcctgac agctgaggac acggctattt attactgtgc gaaagagtcc    300
attttagcag ccctctttga ctactggggc cagggaaccc tggtcactgt ctcctca      357

<210> SEQ ID NO 262
<211> LENGTH: 119
<212> TYPE: PRT
<213> ORGANISM: Artificial Sequence
<220> FEATURE:
<223> OTHER INFORMATION: synthetic

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Phe Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Ile Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 263
<211> LENGTH: 24
<212> TYPE: DNA
<213> ORGANISM: Artificial Sequence
<220> FEATURE:
<223> OTHER INFORMATION: synthetic

<400> SEQUENCE: 263
ggattcacct tcagtagcta tggc                                          24

<210> SEQ ID NO 264
<211> LENGTH: 8
<212> TYPE: PRT
<213> ORGANISM: Artificial Sequence
<220> FEATURE:
<223> OTHER INFORMATION: synthetic

<400> SEQUENCE: 264

Gly Phe Thr Phe Ser Ser Tyr Gly
1               5

<210> SEQ ID NO 265
<211> LENGTH: 24
<212> TYPE: DNA
<213> ORGANISM: Artificial Sequence
<220> FEATURE:
<223> OTHER INFORMATION: synthetic

<400> SEQUENCE: 265
atatcatttg atggaagtaa taaa                                          24

<210> SEQ ID NO 266
<211> LENGTH: 8
<212> TYPE: PRT
<213> ORGANISM: Artificial Sequence
<220> FEATURE:
<223> OTHER INFORMATION: synthetic

<400> SEQUENCE: 266

Ile Ser Phe Asp Gly Ser Asn Lys
1               5

<210> SEQ ID NO 267
<211> LENGTH: 36
<212> TYPE: DNA
<213> ORGANISM: Artificial Sequence
<220> FEATURE:
<223> OTHER INFORMATION: synthetic

<400> SEQUENCE: 267
gcgaaagagt ccattttagc agccctcttt gactac                             36

<210> SEQ ID NO 268
<211> LENGTH: 12
<212> TYPE: PRT
<213> ORGANISM: Artificial Sequence
<220> FEATURE:
<223> OTHER INFORMATION: synthetic

<400> SEQUENCE: 268

Ala Lys Glu Ser Ile Leu Ala Ala Leu Phe Asp Tyr
1               5                   10

<210> SEQ ID NO 269
<211> LENGTH: 336
<212> TYPE: DNA
<213> ORGANISM: Artificial Sequence
<220> FEATURE:
<223> OTHER INFORMATION: synthetic

<400> SEQUENCE: 269

```
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccaag acagcctcct aacctgctca tttactgggc atctattcgg   180
gaatccgggg tccctgaccg attcagtggc agcgggtctg ggacagattt cactctcacc   240
atcagcagcc tgcaggctga agatgtggca ttttattact gtcagcaatt ttatagtatt   300
cccactttg gccaggggac caagctggag atcaaa                              336
```

<210> SEQ ID NO 270
<211> LENGTH: 112
<212> TYPE: PRT
<213> ORGANISM: Artificial Sequence
<220> FEATURE:
<223> OTHER INFORMATION: synthetic

<400> SEQUENCE: 270

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Pro Asn Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Phe Tyr Tyr Cys Gln Gln
                85                  90                  95

Phe Tyr Ser Ile Pro Thr Phe Gly Gln Gly Thr Lys Leu Glu Ile Lys
            100                 105                 110

<210> SEQ ID NO 271
<211> LENGTH: 36
<212> TYPE: DNA
<213> ORGANISM: Artificial Sequence
<220> FEATURE:
<223> OTHER INFORMATION: synthetic

<400> SEQUENCE: 271

```
cagagtgttt tatacagctc caacaataag aactac                              36
```

<210> SEQ ID NO 272
<211> LENGTH: 12
<212> TYPE: PRT
<213> ORGANISM: Artificial Sequence
<220> FEATURE:
<223> OTHER INFORMATION: synthetic

<400> SEQUENCE: 272

Gln Ser Val Leu Tyr Ser Ser Asn Asn Lys Asn Tyr

<210> SEQ ID NO 273
<211> LENGTH: 9
<212> TYPE: DNA
<213> ORGANISM: Artificial Sequence
<220> FEATURE:
<223> OTHER INFORMATION: synthetic

<400> SEQUENCE: 273 tgggcatct                                                                 9

<210> SEQ ID NO 274
<211> LENGTH: 3
<212> TYPE: PRT
<213> ORGANISM: Artificial Sequence
<220> FEATURE:
<223> OTHER INFORMATION: synthetic

<400> SEQUENCE: 274

Trp Ala Ser
1

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
cagcaatttt atagtattcc cact                                               24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gln Gln Phe Tyr Ser Ile Pro Thr
1               5

<210> SEQ ID NO 277
<211> LENGTH: 357
<212> TYPE: DNA
<213> ORGANISM: Artificial Sequence
<220> FEATURE:
<223> OTHER INFORMATION: synthetic

<400> SEQUENCE: 277
caggtgcagc tggtggagtc tgggggaggc gtggtccagc ctggagggtc cctgagactc        60
tcctgtgcag cctctggatt cacctttagg acctatggca tgcactgggt ccgccaggct       120
ccagtcaagg ggctggagtg ggtggcattt atatcaaagg atggaagtga taaatactat       180
gtagactccg tgaagggccg attcaccatc tccagagaca attccaagaa cacgctgttt       240
ctgcaaatga acagcctgac agctgaggac acggctgttt attattgtgc gaaagagtcc       300
attttagcag ccctctttga ctactggggc cagggaaccc tggtcactgt ctcctca         357

<210> SEQ ID NO 278
<211> LENGTH: 119
<212> TYPE: PRT
<213> ORGANISM: Artificial Sequence
<220> FEATURE:
<223> OTHER INFORMATION: synthetic

<400> SEQUENCE: 278

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Val Lys Gly Leu Glu Trp Val
        35                  40                  45

Ala Phe Ile Ser Lys Asp Gly Ser Asp Lys Tyr Tyr Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Tyr Trp Gly Gln Gly
            100                 105                 110

Thr Leu Val Thr Val Ser Ser
        115

<210> SEQ ID NO 279
<211> LENGTH: 24
<212> TYPE: DNA
<213> ORGANISM: Artificial Sequence
<220> FEATURE:
<223> OTHER INFORMATION: synthetic

<400> SEQUENCE: 279
ggattcacct ttaggaccta tggc                                        24

<210> SEQ ID NO 280
<211> LENGTH: 8
<212> TYPE: PRT
<213> ORGANISM: Artificial Sequence
<220> FEATURE:
<223> OTHER INFORMATION: synthetic

<400> SEQUENCE: 280

Gly Phe Thr Phe Arg Thr Tyr Gly
1               5

<210> SEQ ID NO 281
<211> LENGTH: 24
<212> TYPE: DNA
<213> ORGANISM: Artificial Sequence
<220> FEATURE:
<223> OTHER INFORMATION: synthetic

<400> SEQUENCE: 281
atatcaaagg atggaagtga taaa                                        24

<210> SEQ ID NO 282
<211> LENGTH: 8
<212> TYPE: PRT
<213> ORGANISM: Artificial Sequence
<220> FEATURE:
<223> OTHER INFORMATION: synthetic

<400> SEQUENCE: 282

Ile Ser Lys Asp Gly Ser Asp Lys
1               5

<210> SEQ ID NO 283
<211> LENGTH: 36
<212> TYPE: DNA
<213> ORGANISM: Artificial Sequence
<220> FEATURE:
<223> OTHER INFORMATION: synthetic

<400> SEQUENCE: 283
gcgaaagagt ccattttagc agccctcttt gactac                                 36

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

Ala Lys Glu Ser Ile Leu Ala Ala Leu Phe Asp Tyr
1               5                   10

<210> SEQ ID NO 285
<211> LENGTH: 336
<212> TYPE: DNA
<213> ORGANISM: Artificial Sequence
<220> FEATURE:
<223> OTHER INFORMATION: synthetic

<400> SEQUENCE: 285
gacatcgtga tgacccagtc tccagactcc ctggctgtgt ctctgggcga gagggccacc        60
atcaactgca agtccagcca gagtgtttta tacagctcca acaataagaa ctacttagct       120
tggtaccagc agaaaccaag acagcctcct aaactcctca tttactgggc atctaatcgg       180
gaatccgggg tccctgaccg attcagtggc agcgggtctg ggacagattt cactctcacc       240
atcagcagcc tgcaggctga agatgtggca gtttattact gtcagcaatt ttatagtgtt       300 cccactttg gccaggggac caagctggag atcaaa                                  336

<210> SEQ ID NO 286
<211> LENGTH: 112
<212> TYPE: PRT
<213> ORGANISM: Artificial Sequence
<220> FEATURE:
<223> OTHER INFORMATION: synthetic

<400> SEQUENCE: 286

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Thr Phe Gly Gln Gly Thr Lys Leu Glu Ile Lys
            100                 105                 110

<210> SEQ ID NO 287
<211> LENGTH: 36
<212> TYPE: DNA
<213> ORGANISM: Artificial Sequence
<220> FEATURE:
<223> OTHER INFORMATION: synthetic

<400> SEQUENCE: 287
cagagtgttt tatacagctc caacaataag aactac                        36

<210> SEQ ID NO 288
<211> LENGTH: 12
<212> TYPE: PRT
<213> ORGANISM: Artificial Sequence
<220> FEATURE:
<223> OTHER INFORMATION: synthetic

<400> SEQUENCE: 288

Gln Ser Val Leu Tyr Ser Ser Asn Asn Lys Asn Tyr
1               5                   10

<210> SEQ ID NO 289
<211> LENGTH: 9
<212> TYPE: DNA
<213> ORGANISM: Artificial Sequence
<220> FEATURE:
<223> OTHER INFORMATION: synthetic

<400> SEQUENCE: 289 tgggcatct                                                      9

<210> SEQ ID NO 290
<211> LENGTH: 3
<212> TYPE: PRT
<213> ORGANISM: Artificial Sequence
<220> FEATURE:
<223> OTHER INFORMATION: synthetic

<400> SEQUENCE: 290

Trp Ala Ser
1

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
cagcaatttt atagtgttcc cact                                     24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gln Gln Phe Tyr Ser Val Pro Thr
1               5

<210> SEQ ID NO 293
<211> LENGTH: 357
<212> TYPE: DNA
<213> ORGANISM: Artificial Sequence
<220> FEATURE:
<223> OTHER INFORMATION: synthetic

<400> SEQUENCE: 293
caggtgcagc tggtggagtc tgggggaggc gtggtccagc ctgggaggtc cctgagactc    60
tcctgtgcag cctctggatt cacctttagt agctatggca tgcactgggt ccgccaggct   120
ccagtcaagg ggctggagtg ggtggcattt atatcaaatg ataaaagtaa taaatactat   180
gcagactccg tgaagggccg attcaccatc tccagagaca attccaagaa cacgctgtat   240
ctgcaaatga acagcctgac agctgaggac acggctgttt attactgtgc gaaagagtcc   300
attttagcag ccctctttga ctcctggggc cagggaaccc tggtcaccgt ctcctca     357

<210> SEQ ID NO 294
<211> LENGTH: 119
<212> TYPE: PRT
<213> ORGANISM: Artificial Sequence
<220> FEATURE:
<223> OTHER INFORMATION: synthetic

<400> SEQUENCE: 294

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Val Lys Gly Leu Glu Trp Val
        35                  40                  45

Ala Phe Ile Ser Asn Asp Lys Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Glu Ser Ile Leu Ala Ala Leu Phe Asp Ser Trp Gly Gln Gly
            100                 105                 110

Thr Leu Val Thr Val Ser Ser
        115

<210> SEQ ID NO 295
<211> LENGTH: 24
<212> TYPE: DNA
<213> ORGANISM: Artificial Sequence
<220> FEATURE:
<223> OTHER INFORMATION: synthetic

<400> SEQUENCE: 295
ggattcacct ttagtagcta tggc                                           24

<210> SEQ ID NO 296
<211> LENGTH: 8
<212> TYPE: PRT
<213> ORGANISM: Artificial Sequence
<220> FEATURE:
<223> OTHER INFORMATION: synthetic

<400> SEQUENCE: 296

Gly Phe Thr Phe Ser Ser Tyr Gly
1               5

<210> SEQ ID NO 297
<211> LENGTH: 24

<210> SEQ ID NO 297
<211> LENGTH: (not shown)
<212> TYPE: DNA
<213> ORGANISM: Artificial Sequence
<220> FEATURE:
<223> OTHER INFORMATION: synthetic

<400> SEQUENCE: 297
atatcaaatg ataaaagtaa taaa                                           24

<210> SEQ ID NO 298
<211> LENGTH: 8
<212> TYPE: PRT
<213> ORGANISM: Artificial Sequence
<220> FEATURE:
<223> OTHER INFORMATION: synthetic

<400> SEQUENCE: 298

Ile Ser Asn Asp Lys Ser Asn Lys
1               5

<210> SEQ ID NO 299
<211> LENGTH: 36
<212> TYPE: DNA
<213> ORGANISM: Artificial Sequence
<220> FEATURE:
<223> OTHER INFORMATION: synthetic

<400> SEQUENCE: 299
gcgaaagagt ccatttagc agccctcttt gactcc                               36

<210> SEQ ID NO 300
<211> LENGTH: 12
<212> TYPE: PRT
<213> ORGANISM: Artificial Sequence
<220> FEATURE:
<223> OTHER INFORMATION: synthetic

<400> SEQUENCE: 300

Ala Lys Glu Ser Ile Leu Ala Ala Leu Phe Asp Ser
1               5                   10

<210> SEQ ID NO 301
<211> LENGTH: 336
<212> TYPE: DNA
<213> ORGANISM: Artificial Sequence
<220> FEATURE:
<223> OTHER INFORMATION: synthetic

<400> SEQUENCE: 301
gacatcgtga tgacccagtc tccagactcc ctggctgtgt ctctgggcga gagggccacc     60
atcaactgca gtccagcca gagtgtttta tacagctcca acaataagaa ctacttagct    120
tggtaccagc agaaaccaag acagcctcct aagctgctca tttactgggc atctattcgg    180
gaatccgggg tccctgaccg attcagtggc agcgggtctg ggcagattt cactctcacc    240 atcagcagcc tgcaggctgc agatgtggca gtttattact gtcagcaatt ttatagtgtt    300 cccactttg gccaggggac caagctggag atcaaa                              336

<210> SEQ ID NO 302
<211> LENGTH: 112
<212> TYPE: PRT
<213> ORGANISM: Artificial Sequence
<220> FEATURE:
<223> OTHER INFORMATION: synthetic

<400> SEQUENCE: 302

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Arg Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Ala Asp Phe Thr Leu Thr
65                  70                  75                  80

Ile Ser Ser Leu Gln Ala Ala Asp Val Ala Val Tyr Tyr Cys Gln Gln
                85                  90                  95

Phe Tyr Ser Val Pro Thr Phe Gly Gln Gly Thr Lys Leu Glu Ile Lys
            100                 105                 110
```

<210> SEQ ID NO 303
<211> LENGTH: 36
<212> TYPE: DNA
<213> ORGANISM: Artificial Sequence
<220> FEATURE:
<223> OTHER INFORMATION: synthetic

<400> SEQUENCE: 303
cagagtgttt tatacagctc caacaataag aactac        36

<210> SEQ ID NO 304
<211> LENGTH: 12
<212> TYPE: PRT
<213> ORGANISM: Artificial Sequence
<220> FEATURE:
<223> OTHER INFORMATION: synthetic

<400> SEQUENCE: 304

```
Gln Ser Val Leu Tyr Ser Ser Asn Asn Lys Asn Tyr
1               5                   10
```

<210> SEQ ID NO 305
<211> LENGTH: 9
<212> TYPE: DNA
<213> ORGANISM: Artificial Sequence
<220> FEATURE:
<223> OTHER INFORMATION: synthetic

<400> SEQUENCE: 305 tgggcatct        9

<210> SEQ ID NO 306
<211> LENGTH: 3
<212> TYPE: PRT
<213> ORGANISM: Artificial Sequence
<220> FEATURE:
<223> OTHER INFORMATION: synthetic

<400> SEQUENCE: 306

```
Trp Ala Ser
1
```

<210> SEQ ID NO 307
<211> LENGTH: 24
<212> TYPE: DNA
<213> ORGANISM: Artificial Sequence
<220> FEATURE:
<223> OTHER INFORMATION: synthetic

```
<400> SEQUENCE: 307
cagcaatttt atagtgttcc cact                                              24

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

Gln Gln Phe Tyr Ser Val Pro Thr
1               5
```